US011591634B1

(12) United States Patent
van Opijnen et al.

(10) Patent No.: US 11,591,634 B1
(45) Date of Patent: Feb. 28, 2023

(54) FORECASTING BACTERIAL SURVIVAL-SUCCESS AND ADAPTIVE EVOLUTION THROUGH MULTIOMICS STRESS-RESPONSE MAPPING AND MACHINE LEARNING

(71) Applicant: Trustees of Boston College, Chestnut Hill, MA (US)

(72) Inventors: Tim van Opijnen, Somerville, MA (US); Zeyu Zhu, Boston, MA (US); Defne Surujon, Brighton, MA (US)

(73) Assignee: The Trustees of Boston College, Chesnut Hill (MA)

( * ) Notice: Subject to any disclaimer, the term of this patent is extended or adjusted under 35 U.S.C. 154(b) by 427 days.

(21) Appl. No.: 16/839,389

(22) Filed: Apr. 3, 2020

Related U.S. Application Data

(60) Provisional application No. 62/828,833, filed on Apr. 3, 2019.

(51) Int. Cl.
*G06F 17/18* (2006.01)
*C12Q 1/18* (2006.01)
*G16B 20/00* (2019.01)

(52) U.S. Cl.
CPC ............... *C12Q 1/18* (2013.01); *G06F 17/18* (2013.01); *G16B 20/00* (2019.02)

(58) Field of Classification Search
CPC ....................................................... G06F 17/18
See application file for complete search history.

(56) References Cited

U.S. PATENT DOCUMENTS

| | | | | |
|---|---|---|---|---|
| 6,287,765 B1* | 9/2001 | Cubicciotti | ............ | C07H 21/00 536/23.1 |
| 9,886,559 B1* | 2/2018 | McNair | ................ | G16H 50/20 |
| 2006/0136184 A1* | 6/2006 | Gustafsson | ............ | G16B 20/20 703/11 |
| 2007/0094166 A1* | 4/2007 | Addison | ................. | G06N 3/12 706/13 |
| 2008/0060357 A1* | 3/2008 | Zimron | ................... | F01K 23/04 60/671 |
| 2015/0134315 A1* | 5/2015 | Sarmiento | .............. | G16B 15/00 703/11 |
| 2017/0220734 A1* | 8/2017 | Colavin | ................. | G16B 40/20 |
| 2018/0320163 A1* | 11/2018 | Koonin | ................ | C12N 15/111 |
| 2020/0372972 A1* | 11/2020 | Kim | ...................... | G16B 20/00 |
| 2021/0183513 A1* | 6/2021 | Chen | ...................... | G06N 3/126 |
| 2021/0371926 A1* | 12/2021 | Zhang | .................. | C12Q 1/6858 |

* cited by examiner

*Primary Examiner* — Eliyah S. Harper
(74) *Attorney, Agent, or Firm* — Lei Fang, Esq.; Smith Tempel Blaha LLC

(57) ABSTRACT

The present disclosure provides a novel integrated entropy-based method that combines genome-wide profiling and network analyses for diagnostic and prognostic applications. The present disclosure further provides the integration of multiomics datasets, network analyses and machine learning that enable predictions on diagnosing infectious diseases and predicting the probability that they will escape treatment/the host immune system and/or become antibiotic resistant. The present disclosure provides a primary gateway towards the development of highly accurate infectious disease prognostics.

20 Claims, 41 Drawing Sheets

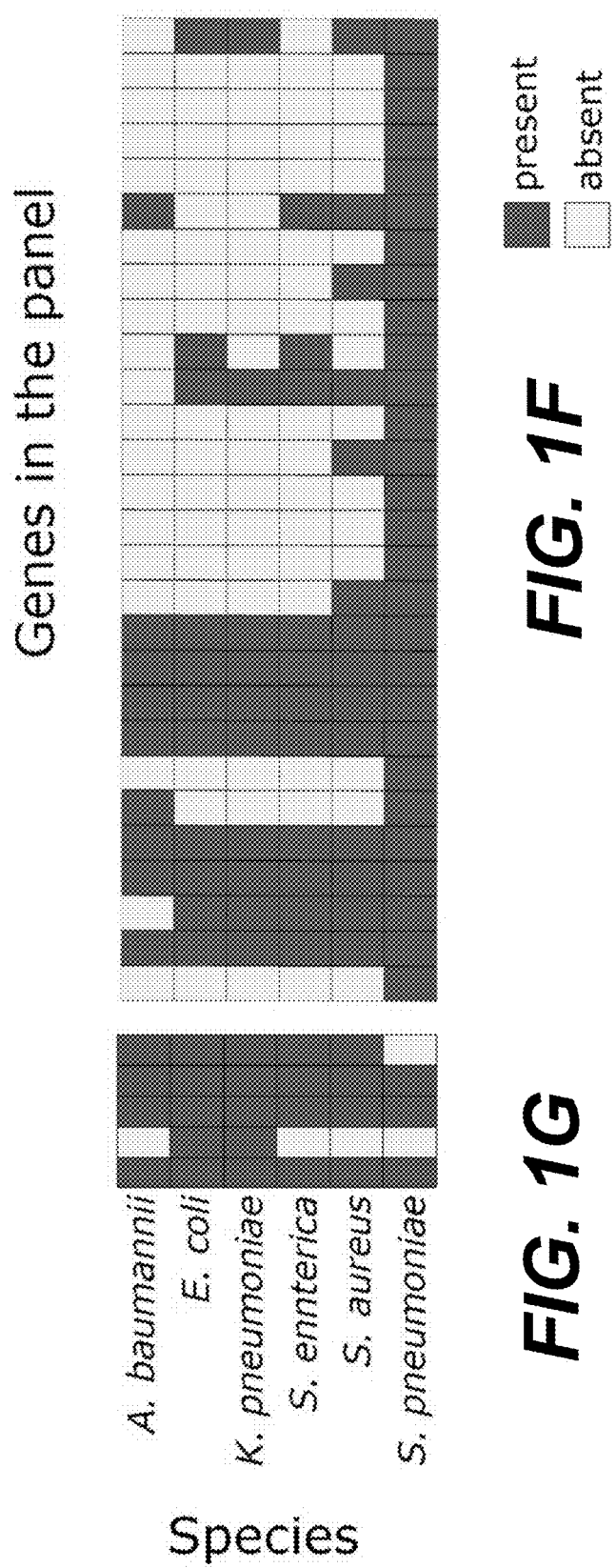

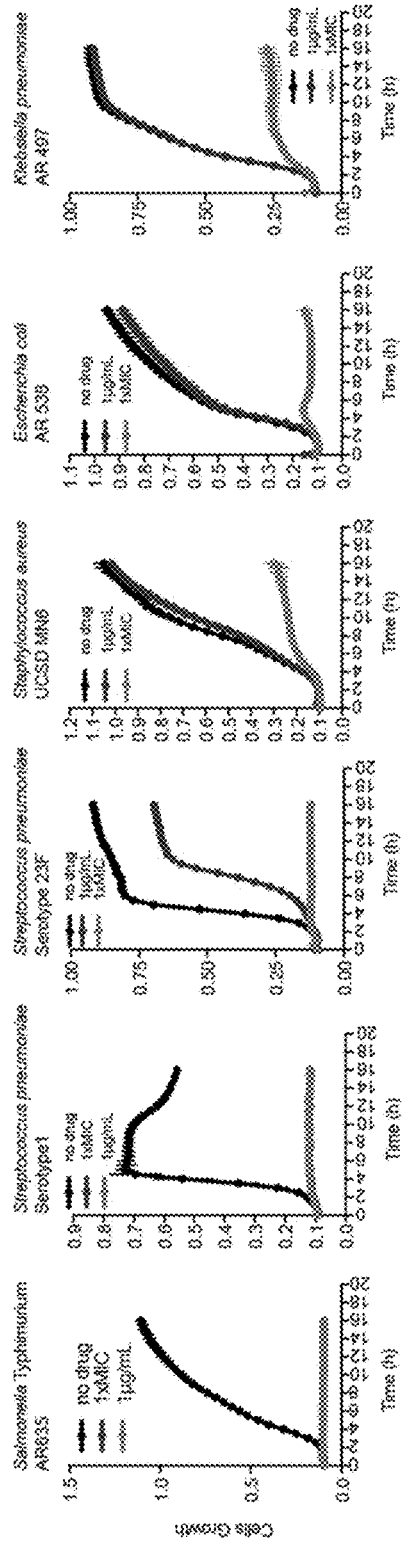
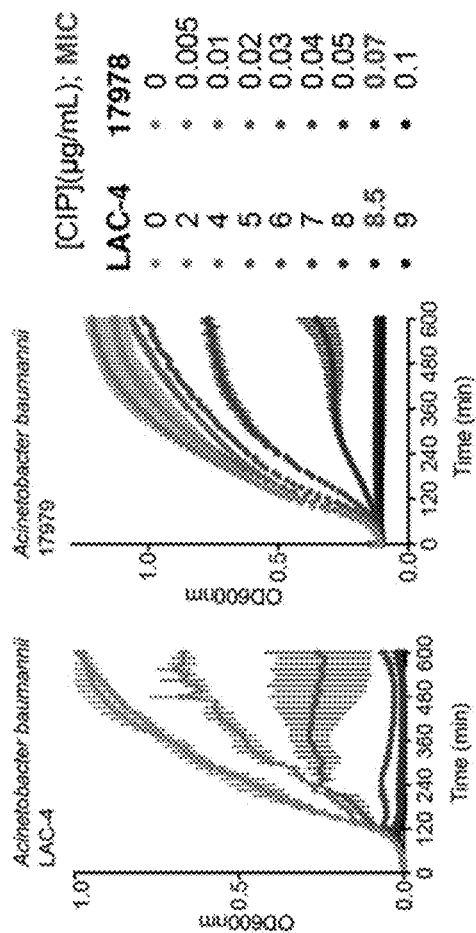
FIG. 6G
FIG. 6H

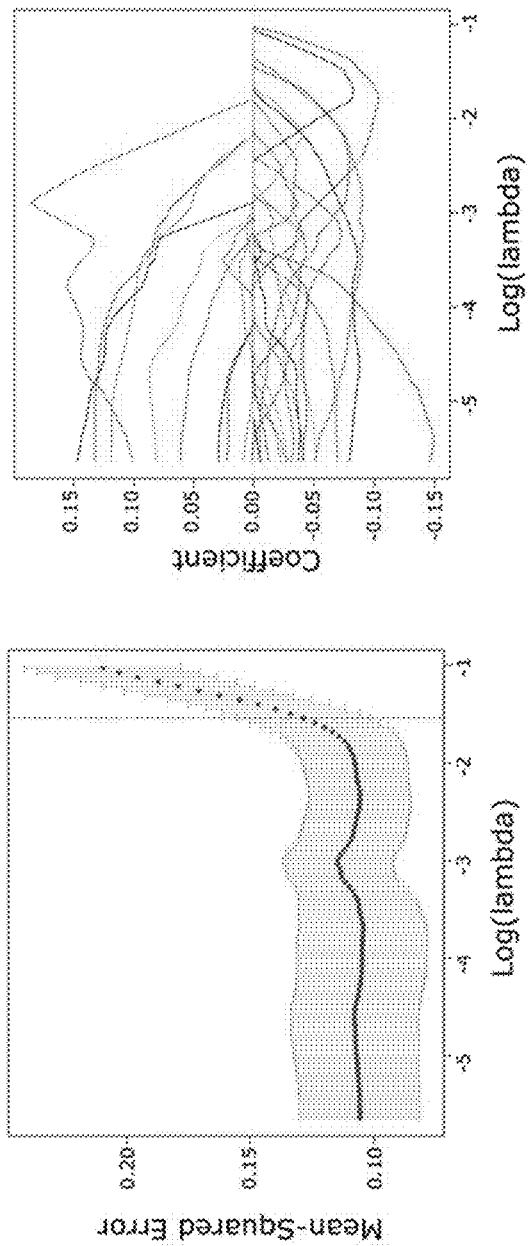
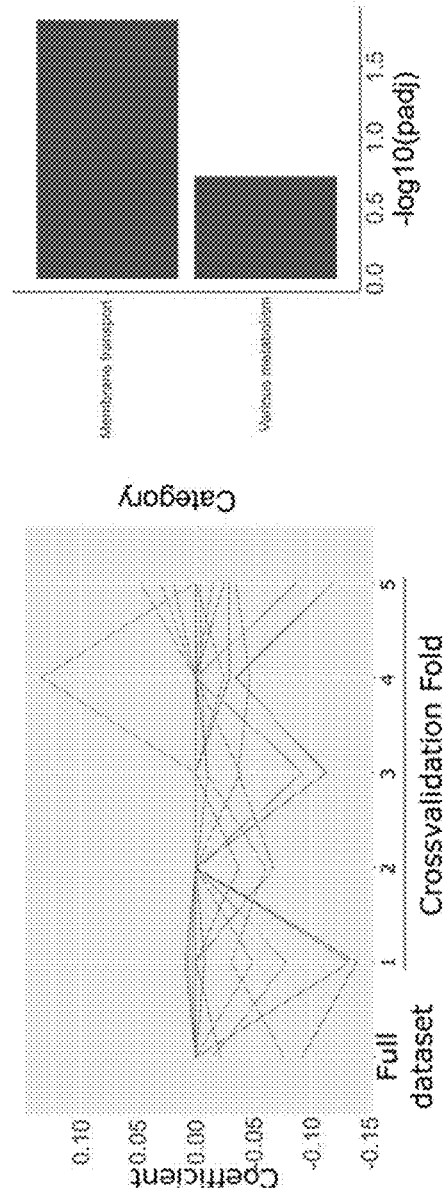
FIG. 8A
FIG. 8B
FIG. 8C
FIG. 8D

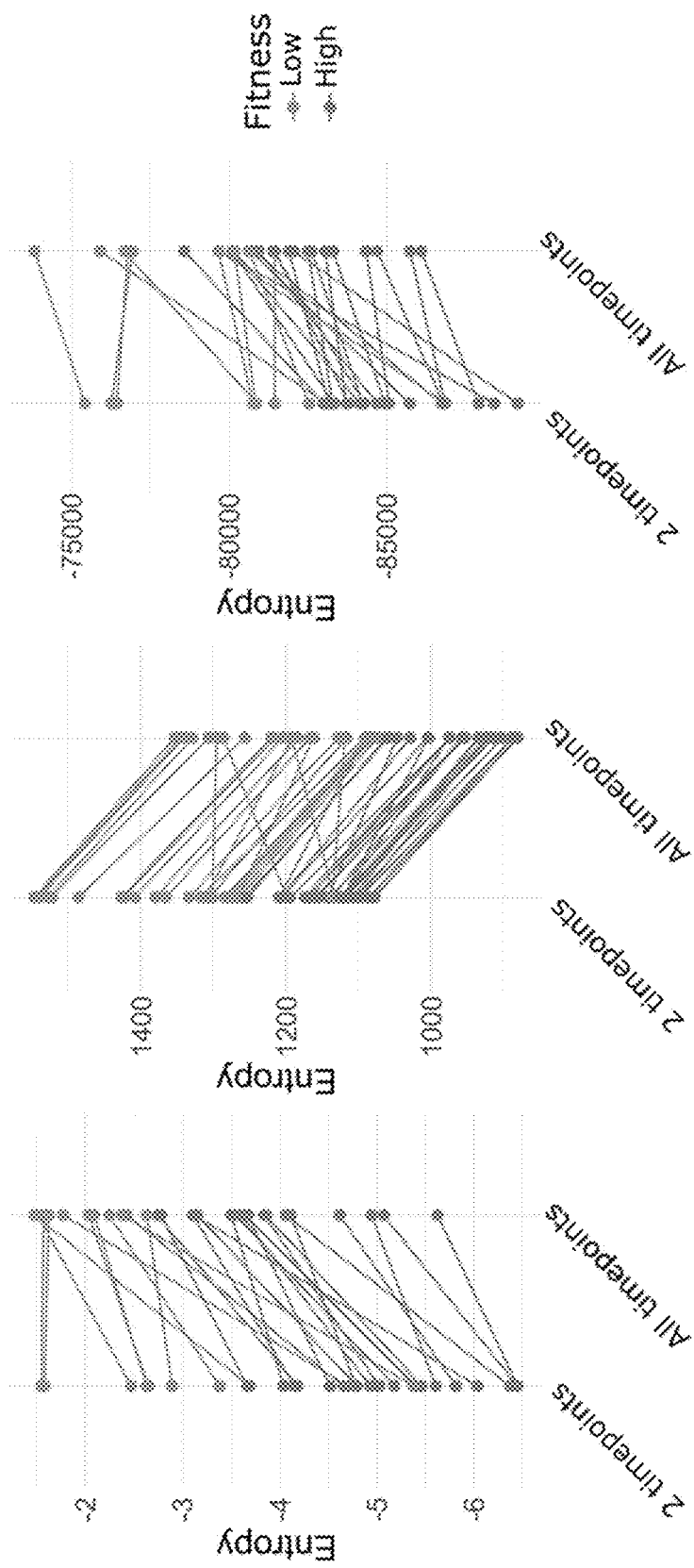

FORECASTING BACTERIAL SURVIVAL-SUCCESS AND ADAPTIVE EVOLUTION THROUGH MULTIOMICS STRESS-RESPONSE MAPPING AND MACHINE LEARNING

CROSS-REFERENCE FOR RELATED APPLICATION

This Application claims the benefit of U.S. Provisional Application No. 62/828,833, filed on Apr. 3, 2019, which is incorporated herein by reference in its entirety.

STATEMENT OF GOVERNMENT SUPPORT

The current technology was developed using funds supplied by the National Institutes of Health (NIH) under grant No. RO1 A1110724 and grant No. U01 A1124302. Accordingly, the U.S. Government has certain rights to this invention.

FIELD OF THE INVENTION

The present invention is directed to a novel integrated species-independent fitness prediction method based on entropy for diagnostic and prognostic applications, particularly for diagnostic and prognostic tests for infectious disease.

BACKGROUND OF THE INVENTION

It is generally assumed that in order to overcome a stress, bacteria activate a response such as the stringent response under nutrient deprivation[1-3] or the SOS response in the presence of DNA damage[4,5]. Measuring the activation of a specific response, or genes associated with this response, can thereby function as an indicator of what type of stress is occurring in a bacterium. For instance, lexA, encoding a master regulator of the SOS response in Escherichia coli and Salmonella[6,7], is upregulated in response to fluoroquinolones, indicative of the DNA damage resulting from this class of antibiotics'. Moreover, genes implicated in a stress response can help construct statistical models for predicting growth/fitness outcomes under that stress. For instance, gene-panels have been assembled from transcriptomic data to predict whether a bacterium can successfully grow in the presence of specific antibiotics[8-12]. This type of prediction of growth under antibiotic conditions can lead to point-of-care diagnostics that guide decisions on antibiotic prescription[13].

While methods that are based on a known stress-response or a gene-panel can be valuable in determining a bacterium's sensitivity to a stress, these methods have limited applicability: they only work for small sets of strains, species or environments. For instance, responses such as the stringent or SOS response are only well characterized in a small number of species, genes in a gene-panel may not be present in other strains or species, and responses are not necessarily regulated in the same manner in different strains or species[14,15]. This means that every time such an approach is applied to a new strain, species or condition, a new gene-panel needs to be assembled and validated, which requires the collection of large amounts of data for model training. In contrast, a universal stress response signature would allow for the development of a predictive model that would work for multiple species and conditions, without relying on collecting new data for different settings. While certain organisms may elicit a "general stress response", i.e. regulatory changes coordinated by the same mechanism in response to different types of stress, this general response has not been defined for many species, and it is still not clear to what extent the downstream transcriptional changes triggered under different stress factors overlap[16]. Until this point, there is no generally agreed upon stress response signature that performs as a fitness predictor, with equal or better performance than the gene-panel approaches.

One possible key ingredient in building a universal predictor is to base a prediction not on specific genes, but rather on a bacterium's global response to stress. A global, genome-wide stress response can be captured on at least two organizational levels; RNA-Seq captures transcriptional changes, while transposon-insertion sequencing (Tn-Seq) characterizes the phenotypic importance of genes, i.e. a gene's contribution to fitness in a specific environment[17-22]. It was previously shown that when an organism is challenged with an evolutionarily familiar stress (i.e. one that has been experienced for many generations), it triggers a subtle response, whereas the response becomes more chaotic when the bacterium responds to a relatively unfamiliar stress, for instance antibiotics[17]. This suggests that the degree to which a bacterium is adapted to a specific stress may be predicted from the global response it elicits. It is possible to observe genome-wide differences between stress-susceptible and stress-resistant bacteria in data from previously published transcriptomic studies that mostly focus on gene-panel approaches. Specifically, in these data it can be observed that the number of differentially expressed genes, and the magnitude of changes in expression seem to be more dramatic in stress-susceptible strains than stress-resistant ones[8-12,23]. Therefore, if these are indeed characteristic differences between responses coming from stress-sensitive and stress-resistant bacteria, and these differences can be appropriately quantified, an opportunity would arise to define a universal method that can predict fitness for multiple species and conditions.

SUMMARY OF THE INVENTION

The need for improved diagnostic tests for infectious diseases is tremendous. For instance, respiratory infections are one of the most common reasons for physician visits and account for a large proportion of antibacterial use. Additionally, the prescribed drugs are often ineffective (e.g. antibiotics prescribed against viral infections) or unnecessary (e.g. the infection would have resolved by itself). While there is a growing field of rapid diagnostic tests to identify the infectious agent, assays that identify the state of the infection and can predict whether the infection is being cleared or is transitioning to a different niche and/or progressing towards disease are lacking. Such predictive diagnostics would, enable the ability to provide personalized prescriptions and limit the overuse of antibacterial agents, which is one of the most vexing issues facing modern medicine.

Accordingly, the present disclosure provides a novel integrated approach that combines genome-wide profiling and network analyses which enables predictions for diagnostic and/or prognostic outcomes, for instance, on bacterial short-term survival. In certain embodiments, the present disclosure provides entropy-based prediction on whether an infection is being cleared or is progressing towards disease and would need (additional) treatment. Moreover, the present disclosure provides an integration of multiomics datasets, network analyses and machine learning which enables predictions on bacterial long-term survival. In certain embodiments, the present disclosure provides multiomics datasets, network analyses and machine learning which allows for accurate predictions of adaptive mutations that would help the bacterium escape the host immune system and/or antimicrobial treatment. These approaches offer a primary gateway towards the development of highly accurate infectious disease prognostics.

In certain embodiments, the present disclosure provides that a substantial transcriptomic dataset for the bacterial pathogen *Streptococcus pneumoniae* was generated and analyzed. To validate this dataset, existing gene-panel approaches were replicated and scrutinized as a point-of-comparison. The present disclosure provides that bacterial fitness under antibiotic or nutrient stress can be predicted by expression profiles from small gene-panels, while a separate panel can predict an antibiotic's mechanism of action. The existing approaches have limitations that gene-panels are sensitive to model parameters and the data being trained on are limited to strains and species that share the same genes. With the goal to develop a general approach, it is observed that global transcriptional disorder seems to be a common stress feature in bacteria. It turns out that increasing disorder stems from an increasing loss of dependencies among genes (e.g. regulatory interactions). These dependencies manifest as correlations in gene expression patterns, and by accounting for these dependencies, the statistical definition of entropy can be used to accurately quantify the amount of disorder in the system.

The present disclosure provides entropy-based modeling and/or prediction for diagnostic and prognostic applications. In certain embodiments, the present disclosure provides a prediction on what the best treatment option is and if treatment is really necessary. The present disclosure further provides a prediction and/or determination on what drug should be used in case of treatment, what the probability is that resistance would emerge if a drug is applied, and what the probability is that the bacterium would escape the immune system/treatment and progress towards disease.

The present disclosure provides an approach that can be used to make predictions on infection progression in a patient. In certain embodiments, the present disclosure provides that a sample from a patient is collected, RNA expression analyses on that entire sample are performed on the bacterium and on the host response simultaneously. The combined entropy level of the patient-response and that of the bacterium gives an indication whether the patient is successfully controlling the infection (and doesn't need [additional] treatment), or whether the infection is 'winning' and the patient needs treatment, or additional treatment.

In certain embodiments, the present disclosure provides the entropy-based approach as for Antibiotic Susceptibility Test (AST), comprising the following steps: a) collecting a bacterium from a patient carrying any bacterium of interes, b) exposing the collected bacterium to a tested antibiotic at a suitable concentration for about 90 minutes, c) collecting RNA from the bacterium after it is exposed to the tested antibiotic and performing RNA expression analyses, d) performing entropy calculation from a presented model for survival probability and an actual level of antibiotic sensitivity, and e) providing recommendation on optimal treatment with the tested antibiotics in view of the survival probability abd the actual level of antibiotic sensitivity.

In certain embodiments, the present disclosure provides that when entropy was calculated using time-series RNA-Seq data and dependencies amongst genes were accounted for, stress-sensitive strains have higher entropy than stress-insensitive ones. This enables fitness predictions using a simple decision rule, where if entropy is either above or below a threshold, fitness is respectively low or high. Importantly, this entropy-based method achieves better performance in predicting fitness outcomes compared to existing gene-panel approaches. In order to simplify the approach, the present disclosure provides that entropy can be calculated using a single time-point and does not necessarily require time-series data to achieve high accuracy.

To highlight the universality of entropy, in addition to evaluating performance on a previously unseen test set, validation experiments were performed for 7 Gram-negative and -positive pathogenic species, and the approach was applied to multiple published datasets. Moreover, the present disclosure provides that transcriptional entropy is correlated with the level of antibiotic sensitivity, enabling MIC predictions.

Therefore, the present disclosure provides a large new experimental dataset, and a novel species-independent fitness prediction method based on entropy. By carefully defining entropy, the present disclosure provides that entropy does not simply capture large changes in expression, but instead builds upon a very intuitive notion of disorder and enables predictions on bacterial fitness. The present disclosure provides the gene-panel based methods as a baseline for comparison, but that the entropy-based methods of the present disclosure perform better, and are robust to parameter tuning, and can accommodate different amounts of data to enable fitness predictions. Most importantly, unlike gene-panels, the entropy-based predictions of the present disclosure generalize to previously unseen settings, and to multiple pathogenic bacteria.

BRIEF DESCRIPTION OF THE DRAWINGS

Many aspects of the present disclosure can be better understood with reference to the following drawings. The components in the drawings are not necessarily to scale, emphasis instead being placed upon clearly illustrating the principles of the present disclosure. Moreover, in the drawings, like reference numerals designate corresponding parts throughout the several views.

FIGS. 1A-1G. Gene panel-based fitness predictions of *S. pneumoniae* under antibiotic and nutrient stress. FIG. 1A. Project setup and overview. Wildtype and adapted strains of *S. pneumoniae* are exposed to 16 different antibiotics, belonging to 4 different classes, and their fitness outcomes in each condition is determined by growth curves. Temporal RNA-Seq data is used to train models that predict the MOA of an antibiotic, and the fitness outcome of a strain using gene-panel approaches. The concept of entropy is developed expanding predictions to MIC and fitness for other strains and species in the presence of antibiotics and in non-antibiotic conditions. CWSI (cell wall synthesis inhibitors): AMX—amoxicillin, CEF—cefepime, CFT—ceftriaxone, IMI—imipenem, PEN—penicillin, VNC—vancomycin; DSI (DNA synthesis inhibitors): CIP—ciprofloxacin, COT—cotrimoxazole, LVX—levofloxacin, MOX—moxifloxacin, RSI (RNA synthesis inhibitor): RIF—rifampicin; PSI (protein synthesis inhibitors): KAN—kanamycin. LIN—linezolid, TET—tetracycline, TOB—tobramycin; DAP—daptomycin (a membrane disruptor). FIG. 1B. A gene panel for fitness prediction is generated by a regularized logistic regression model fit on 231 *S. pneumoniae* RNA-Seq profiles collected from antibiotic exposure (strains T4 and 19F) or strain D39-essential nutrient depletion conditions in stress-sensitive and stress-insensitive strains. The value of lambda (dashed line, 0.0428) was selected to be the largest at which crossvalidation error (mean squared error) is within 1 standard deviation of the minimum mean squared error (which corresponds to lambda=0.0097), resulting in 28 genes in the fitness prediction gene panel. The points and error bars represent mean ±standard deviation of error across 5 crossvalidation folds. FIG. 1C. Prediction performance of the fitness gene panel is shown as confusion matrices for the training (top) and test (bottom) datasets. The gene-panel generates 10 and 4 false positives, and an overall accuracy of 0.93 and 0.77 in the training and test data sets respectively. FIG. 1D. Coefficients of individual features (i.e. genes) are plotted for the model trained on the full dataset, and 5 crossvalidation training folds, where 20% of the data is omitted during model fitting. The gene panel is highly affected by training data, indicated by many genes having nonzero coefficients on some folds, but not others. Only 5 out of the 28 genes in the fitness gene-panel have nonzero coefficients, and thus are maintained as predictors in the regression model, across all folds. FIG. 1E. Each gene's coefficient is plotted as an individual line, against varying values of lambda. The gene panel is highly affected by regularization strength (lambda), indicated by the nonmonotonic increase or decrease in the coefficient in each gene. In fact, there are many genes that have nonzero coefficients only for a small range of lambda. Dashed line depicts the automatically selected value of lambda as in FIG. 1B. FIG. 1F. The presence and absence of each of the 28 genes in the *S. pneumoniae* fitness panel is highly variable across 5 Gram-positive and Gram-negative species. FIG. 1G, An *E. coli* ciprofloxacin sensitivity panel, which was generated in reference 8, also suffers from a lack of conservation across the same group of species. Gene numbers are omitted for clarity but can be retrieved in Table 5.

FIG. 2A. Principal component analysis (PCA) on differential expression datasets from sensitive *S. pneumoniae* strains T4 and 19F grown in the presence of 16 different antibiotics at 1xMIC depicts antibiotic responses as temporal transcriptional trajectories. Each line describes the trajectory of one of the strains in the presence of a CWSI (AMX, CEF, CFT, IMI, PEN, VNC), DSI (CIP, COT, LVX, MOX) PSI (KAN, LIN, TET, TOB) or RSI (RIF). Trajectories for each strain are largely grouped based on their MOA and grouped-trajectories become more distinct over time. The size of each data point increases with the time of antibiotic exposure; each trajectory is split into 6 timepoints, e.g. for an experiment that spans 120' each point indicates a 20' increment. Abbreviations are as in FIGS. 1A-1G. FIG. 2B. In order to quantify the separation of the PCA trajectories by an antibiotic's MOA, pairwise distances between PCA trajectories were computed. Pairs of transcriptional trajectories obtained using drugs within the same MOA tend to have smaller distances than pairs obtained using drugs with different MOA's. k-means clustering of the trajectory distances groups the trajectories mostly by MOA, although some PSI and CWSI trajectories are grouped with DSI ones. The top and bottom bars above the heatmap show the k-means clustering result, and the real MOA of each trajectory respectively, which have 64% agreement. FIG. 2C. Confusion matrices indicating the performance of the gene-panel that predicts MOA. This panel was generated using a multi-class regression model (See Table 1 for the training and test set split, and Methods for details on parameter tuning) and consists of 34 genes. The gene-panel correctly predicts the MOA on all training set data and only misclassifies a single experiment on the previously unseen test dataset, showing the different MOA's being easily distinguishable with simple gene-based methods.

FIG. 3A. Depiction of the transcriptomic response of wildtype T4 and VNC-adapted T4 in response to 1xMIC-wt of Vancomycin. Differential expression of each gene over time is represented as a line. The temporal response of the wildtype strain shows an escalating response over time, with increasing and fluctuating transcriptional changes. In contrast the adapted strain's response is very much contained and only small changes in expression occur. The response of the wildtype thus seems to be much more disordered than the adapted-response and has higher entropy. FIG. 3B. Entropy captures disorder in a transcriptome and not simply high-magnitude changes. The top panel shows 3 hypothetical scenarios, where differential expression (DE) of four individual genes are tracked over time. In the top panel in scenarios 1 and 2, the individual genes are dependent on each other and follow similar transcriptional trajectories. These genes thus have some sort of regulatory interaction, for instance because they are in a single operon. In scenario 2, the individual genes' expression patterns have differences in magnitude and direction, but all genes still have similar overall expression trajectories that co-vary. In scenario 3, dependencies are largely absent and the overall changes in DE seem much more disordered. In the bottom panel: The magnitude changes (quantified as the sum of absolute DE), and entropy for the 3 scenarios are compared. While the largest changes in magnitude are in scenario 1, both scenario 1 and 2 have relatively low entropy, due to expression patterns of individual genes being ordered and highly dependent on each other. In scenario 3 overall DE is highly similar to the other two scenarios, but the magnitude changes have lost much of their dependency and have become disordered, resulting in high entropy. FIG. 3C. Selection of regularization parameter p 5-fold crossvalidation was used to determine the best choice of p Error (1-accuracy) is reported as the mean ±standard deviation across the 5 folds. The value of p that minimizes the mean crossvalidation error is determined to be 1.5 (red dashed line). FIG. 3D. Performance of temporal entropy-based fitness prediction is shown as receiver-operator characteristic (ROC) curves plotting the sensitivity (i.e. true positive rate) against the false positive rate across a range of thresholds for training (black) and test datasets. The area under the ROC (AUROC) curve shows how well the predictor can separate high and low fitness. The AUROC is 0.89 and 0.94 for the training and test set respectively. FIG. 3E. Performance of temporal entropy-based fitness prediction is shown as Precision-Recall (PR) curves plotting precision (proportion of predicted high-fitness cases that are truly high-fitness) against recall (proportion of true high-fitness cases that are predicted as high-fitness) across a range of thresholds for training (black) and test datasets. The area under the PR curve (AUPRC) shows how well the predictor can detect high fitness cases. The AUPRC is 0.88 and 0.98 for the training and test set respectively. FIG. 3F. Entropy of all experiments in the training (top panel) and test (bottom panel) sets. Each experiment is represented as an individual bar, colored according to the experimentally determined real fitness outcome. Bars above the entropy threshold (Entropy=1066.25) are predicted to be low fitness and bars below the threshold are predicted to be high fitness. Both training and test sets score very well with an accuracy of 0.97 and 0.84 respectively.

FIG. 4A. Genome-wide differential expression (indicated as log2FoldChange Antibiotic/NDC (no drug control)) shows significantly wider distributions in antibiotic-sensitive strains (wtTIGR4 and wt19F) compared to antibiotic-adapted strains in the presence of vancomycin (a cell wall synthesis inhibitor; CWSI) and rifampicin (an RNA synthesis inhibitor; RSI), respectively in a Kolmogorov-Smirnov test. *: $0.001<p<0.05$; : $0.0001<p<0.001$, *: $p<0.0001$. FIG. 4B. Entropy for a single time point is defined as the log-transformed variance of the distribution of differential expression across genes for a specific timepoint. FIG. 4C. Single time point entropy is calculated from differential expression of all genes in experiments in the training (left panels) and test (right panels) datasets at each time point and plotted against time post-stress exposure (i.e. in the presence of antibiotics—AMX, CEF, CFT, CIP, COT, DAP, IMI, KAN, LIN, LVX, MOX, PEN, RIF, TET, TOB, VNC, or in the absence of nutrients—Glycine-GLY, Uracil-URA, Valine-VAL). Dashed line indicates the entropy threshold (2.08) for the single-timepoint entropy predictions of fitness. The performance of the single time-point entropy-based fitness prediction (applied to all timepoints, ranging from 10' to 240') is shown as receiver-operator characteristic (ROC, FIG. 4D.) and Precision-Recall (PR, FIG. 4E.) curves. The area under the ROC curve is 0.79 and 0.88 for training and test sets respectively. The area under the PR curve is 0.77 and 0.96 for training and test sets respectively. FIG. 4F. Confusion matrix of single time-point entropy-based fitness prediction of the training (top panel) and test (bottom panel) datasets, highlights a good performance, but shows that there are a relatively large number of false positives. FIG. 4G. Entropy values of individual experiments in the training (top) and test (bottom) sets, separated by time. Left and right panels show early (≤45 minutes) and late (>45 minutes) timepoints respectively. It turns out that most false positive predictions in panel FIG. 4F come from early timepoints due to a lack in transcriptional changes within the first 45' after antibiotic exposure. In contrast, antibiotic exposure longer than 45' (late timepoints) leads to a clear separation of high and low fitness and high accuracy in training and test data sets.

FIG. 5A. Six strains representing 5 species are ranked from low to high ciprofloxacin minimal inhibitory concentrations ($MIC_{CIP}$) tested by growth curve assays (see also FIGS. 6A-6H). The multi-species CIP RNA-Seq is performed at two CIP concentrations: 1) μg/mL for all 6 strains corresponding to 2 low fitness outcomes (dark gray squares) and 4 high fitness outcomes (light gray squares); 2) $MIC_{CIP}$ for strains that are insensitive to 1 μg/mL of CIP, i.e. S. pneumoniae serotype 23F, S. aureus UCSD Mn6, E. coli AR538, and K. pneumoniae AR497, corresponding to 4 additional low fitness outcomes. The number of genes that change in expression upon exposure to 1 μg/mL CIP (|log2FoldChange|>1 and p-adj<0.05) as well as their change in magnitude is inversely correlated to their CIP sensitivity (FIG. 5B) and their entropy (FIG. 5C). Additionally, strains with $MIC_{CIP}$ higher than 1 μg/mL revert to triggering a large number of differential expression genes (FIG. 5B) and a high entropy (FIG. 5C) at their respective $1xMIC_{CIP}$. FIG. 5D. Using a linear regression model (black line; error band: 95% CI), MIC's are predicted for A. baumannii strains ATCC 17978 and LAC-4 based on their entropy at 1 μg/mL of ciprofloxacin. The predicted and measured MIC for the two strains are highly accurate indicating that entropy can be used as a quantitative predictor. See FIG. 6H for MIC determination for A. baumannii ATCC17978 and LAC-4. FIG. 5E. Further validation of the generalizability of the single time-point entropy approach on expression data from reference 11. The universal entropy threshold of 2.08 trained on our S. pneumoniae data, was successfully used to predict fitness outcomes of susceptible and resistant strains from 3 species in the presence of 3 different antibiotics from reference 8. Importantly, six of the species-antibiotic combinations (GEN-A.b/E.c/K.p and MER-A.b/E.c/K.p) were not present in our datasets, which highlights the universality and generalizability of the entropy based approach. GEN: gentamicin, MER: meropenem. FIG. 5F. Entropy calculated from transcriptional profiles of 193 M. tuberculosis transcription factor over-expression (TFOE) strains from reference 35 separates strains with a >30% fitness defect upon TFOE induction from strains with a fitness advantage or <30% fitness defect upon induction. At the threshold of 0.71, fitness outcomes are correctly predicted at an accuracy of 0.78.

FIGS. 6A-6H. High and low fitness outcomes under antibiotic exposure and single nutrient depletion. FIG. 6A-6E. Growth curves of stress-sensitive S. pneumoniae T4 and 19F strains and antibiotic- or nutrient-adapted strains (labeled as aT4, a19F and aD39). Error bars: standard error of at least three biological replicates. FIG. 6A shows results for experimental conditions CWSI. FIG. 6B shows results for experimental conditions DSI. FIG. 6C shows results for experimental conditions PSI. FIG. 6D shows results for experimental conditions RSI and Membrane disruptor. FIG. 6E shows results for experimental conditions Nutrient depletion. FIG. 6F. Number of generations of adapted populations. Detailed information on minimum inhibitory concentrations is listed in Table 2. FIG. 6G. Growth curves of S. Typhimurium, S. pneumoniae serotypes 1 and 23F strains, S. aureus, E. coli and K. pneumoniae under 1 μg/mL and strain-specific minimum inhibitory concentration (1xMIC) of ciprofloxacin. FIG. 6H. Growth curves of ciprofloxacin MIC determination for A. baumannii strains LAC-4 and ATCC 17978.

FIG. 7A. Heatmaps show the differential expression (log2FoldChange) of each gene in the panel in each of the 19 stress conditions. Each row is a gene in the panel, and each column is a different experiment (experimental timepoints are separate columns). Top: Training set data, Bottom: Test set data. The top bar above the heatmap shows the observed fitness outcome (light gray: low fitness, dark gray: high fitness). The middle and bottom bars above the heatmaps indicate the MOA and identity of the stress respectively. Dendrograms on the top and side of the heatmaps show hierarchical clustering of the columns and rows respectively. FIG. 7B. Balanced accuracy of the regression model is similar for training and test sets at different values of lambda. For lambda <0.05, both train and test set accuracies are >0.85, despite the models selecting different sets of genes (FIG. 1E). FIG. 7C. Receiver-operator characteristic (ROC) curve for the fitness gene-panel. The area under the curve is 0.99 and 0.75 for the training and test sets respectively. FIG. 7D. Precision-Recall (PR) curve for the fitness gene-panel. The area under the curve is 0.99 and 0.31 for the training and test sets respectively. FIG. 7E. No functional category is enriched in the fitness gene-panel. For each category present in the gene-panel, a hypergeometric test was performed, and the resulting p-value is adjusted for false discoveries (padj). No category had padj<0.01.

FIGS. 8A-8L. Gene-panels that predict fitness for specific MOA's are also sensitive to input data, lambda and show no enrichment. (FIGS. 8A-8D) CWSI-specific panel. (FIGS. 8E-8H) DSI-specific panel. (FIGS. 8I-8L) PSI-specific panel. FIGS. 8A, 8E, and 8I show the crossvalidation analysis that determine the value of lambda (as in FIG. 1B). The selected lambda is shown as the dashed line. FIGS. 8B, 8F, and 8J show the coefficients of each gene changing depending on lambda. FIGS. 8C, 8G, and 8K show the coefficients of each gene changing with different input data used. Full dataset: coefficients obtained when the regression model is trained on all available training data for a specific MOA. Crossvalidation fold: coefficients obtained when the model is trained on 80% of the available training data. FIGS. 8D, 8H, and 8L show enrichment analysis of each gene-panel predicting fitness specific to CWSI, DSI, PSI respectively (similar to FIG. 7E). There are no functional categories with padj<0.01.

FIG. 9A. Crossvalidation analysis was applied to determine the best value of lambda on the multi-class regression model that predicts MOA. Unlike the 2-class models, error is evaluated as multinomial deviance. Otherwise, lambda is determined the same way as in FIG. 1B. FIG. 9B. Coefficients of each gene for each class (i.e. MOA, shown as separate sub-panels) change monotonically as lambda is decreased. This is indicative of the genes being more consistent than the gene-panels that predict fitness (FIG. 1E and FIGS. 8B, 8F & 8J). FIG. 9C. Coefficients of each gene, for each class (sub-panels) are affected by input data. Analysis similar to that done in FIG. 1D and FIGS. 8C, 8G & 8K. FIG. 9D. Heatmaps show differential expression (log2FoldChange) of each gene in the MOA gene-panel (rows) in each experimental condition (columns). The bars directly above the heatmaps show the MOA and the antibiotic. Top panel: training set. Bottom panel: test set. Dendrograms above heatmaps show hierarchical clustering of the experiments. FIG. 9E. Functional category enrichment analysis was done similarly to FIG. 7E. There are no categories with padj<0.01.

FIGS. 12A-12C. Entropy is affected by the number of timepoints used. For each of the temporal models, corresponding to $\rho=\infty$ (FIG. 12A), $\rho=1.5$ (Fig, 12B), and $\rho=0$ (FIG. 12C), entropy was computed from the same 2 timepoints (30 and 120 minutes), or alternatively all timepoints available (which can be up to 11 timepoints). The same experiment is connected by a line. For all 3 variants of temporal entropy, the change in the direction when using all timepoints is consistent across experiments.

DETAILED DESCRIPTION OF THE INVENTION

Figure 1A:
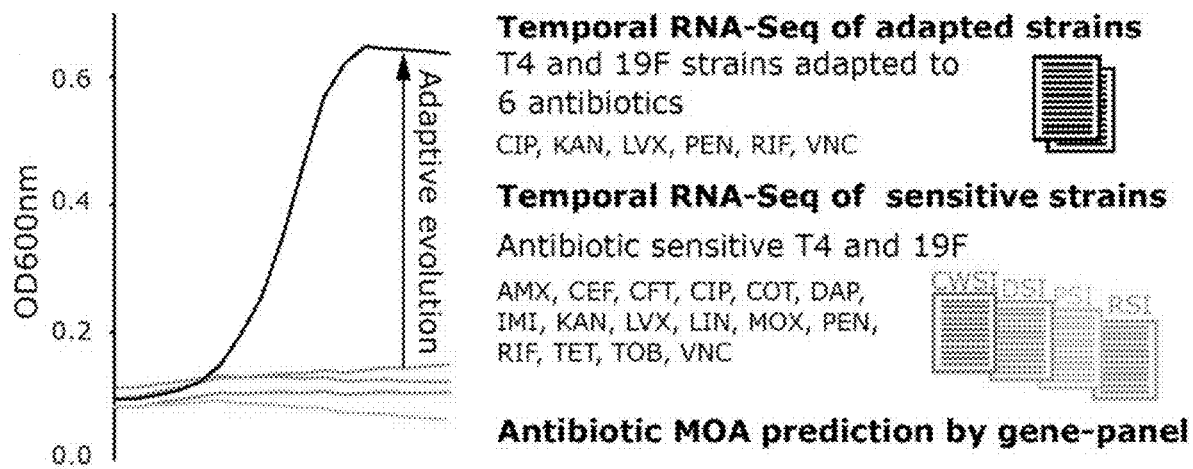
Figure 1A:
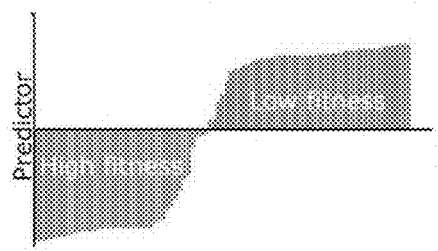

Many modifications and other embodiments disclosed herein will come to mind to one skilled in the art to which the disclosed compositions and methods pertain having the benefit of the teachings presented in the foregoing descriptions and the associated drawings. Therefore, it is to be understood that the disclosures are not to be limited to the specific embodiments disclosed and that modifications and other embodiments are intended to be included within the scope of the appended claims. The skilled artisan will recognize many variants and adaptations of the aspects described herein. These variants and adaptations are intended to be included in the teachings of this disclosure and to be encompassed by the claims herein.

Although specific terms are employed herein, they are used in a generic and descriptive sense only and not for purposes of limitation.

As will be apparent to those of skill in the art upon reading this disclosure, each of the individual embodiments described and illustrated herein has discrete components and features which may be readily separated from or combined with the features of any of the other several embodiments without departing from the scope or spirit of the present disclosure.

Any recited method can be carried out in the order of events recited or in any other order that is logically possible. That is, unless otherwise expressly stated, it is in no way intended that any method or aspect set forth herein be construed as requiring that its steps be performed in a specific order. Accordingly, where a method claim does not specifically state in the claims or descriptions that the steps are to be limited to a specific order, it is no way intended that an order be inferred, in any respect. This holds for any possible non-express basis for interpretation, including matters of logic with respect to arrangement of steps or operational flow, plain meaning derived from grammatical organization or punctuation, or the number or type of aspects described in the specification.

All publications mentioned herein are incorporated herein by reference to disclose and describe the methods and/or materials in connection with which the publications are cited. The publications discussed herein are provided solely for their disclosure prior to the filing date of the present application. Nothing herein is to be construed as an admission that the present invention is not entitled to antedate such publication by virtue of prior invention. Further, the dates of publication provided herein can be different from the actual publication dates, which can require independent confirmation.

While aspects of the present disclosure can be described and claimed in a particular statutory class, such as the system statutory class, this is for convenience only and one of skill in the art will understand that each aspect of the present disclosure can be described and claimed in any statutory class.

It is also to be understood that the terminology used herein is for the purpose of describing particular aspects only and is not intended to be limiting. Unless defined otherwise, all technical and scientific terms used herein have the same meaning as commonly understood by one of ordinary skill in the art to which the disclosed compositions and methods belong. It will be further understood that terms, such as those defined in commonly used dictionaries, should be interpreted as having a meaning that is consistent with their meaning in the context of the specification and relevant art and should not be interpreted in an idealized or overly formal sense unless expressly defined herein.

Prior to describing the various aspects of the present disclosure, the following definitions are provided and should be used unless otherwise indicated. Additional terms may be defined elsewhere in the present disclosure.

A. Definitions

As used herein, "comprising" is to be interpreted as specifying the presence of the stated features, integers, steps, or components as referred to, but does not preclude the presence or addition of one or more features, integers, steps, or components, or groups thereof. Moreover, each of the terms "by", "comprising," "comprises", "comprised of," "including," "includes," "included," "involving," "involves," "involved," and "such as" are used in their open, non-limiting sense and may be used interchangeably. Further, the term "comprising" is intended to include examples and aspects encompassed by the terms "consisting essentially of" and "consisting of." Similarly, the term "consisting essentially of" is intended to include examples encompassed by the term "consisting of.

As used herein, nomenclature for compounds, including organic compounds, can be given using common names, IUPAC, IUBMB, or CAS recommendations for nomenclature. When one or more stereochemical features are present, Cahn-Ingold-Prelog rules for stereochemistry can be employed to designate stereochemical priority, E/Z specification, and the like. One of skill in the art can readily ascertain the structure of a compound if given a name, either by systemic reduction of the compound structure using naming conventions, or by commercially available software, such as CHEMDRAW™ (Cambridgesoft Corporation, U.S.A.).

As used in the specification and the appended claims, the singular forms "a," "an" and "the" include plural referents unless the context clearly dictates otherwise. Thus, for example, reference to "a dendrite," "an antibody," or "a biosensor," includes, but is not limited to, two or more such dendrites, antibodies, biosensors, and the like, including a plurality of such dendrites, antibodies, biosensors, and the like.

It should be noted that ratios, concentrations, amounts, and other numerical data can be expressed herein in a range format. It will be further understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed. Ranges can be expressed herein as from "about" one particular value, and/or to "about" another particular value. Similarly, when values are expressed as approximations, by use of the antecedent "about," it will be understood that the particular value forms a further aspect. For example, if the value "about 10" is disclosed, then "10" is also disclosed.

When a range is expressed, a further aspect includes from the one particular value and/or to the other particular value. For example, where the stated range includes one or both of the limits, ranges excluding either or both of those included limits are also included in the disclosure, e.g. the phrase "x to y" includes the range from 'x' to 'y' as well as the range greater than 'x' and less than 'y'. The range can also be expressed as an upper limit, e.g. 'about x, y, z, or less' and should be interpreted to include the specific ranges of 'about x', 'about y', and 'about z' as well as the ranges of 'less than x', less than y', and 'less than z'. Likewise, the phrase 'about x, y, z, or greater' should be interpreted to include the specific ranges of 'about x', 'about y', and 'about z' as well as the ranges of 'greater than x', greater than y', and 'greater than z'. In addition, the phrase "about 'x' to 'y'", where 'x' and 'y' are numerical values, includes "about 'x' to about 'y'".

It is to be understood that such a range format is used for convenience and brevity, and thus, should be interpreted in a flexible manner to include not only the numerical values explicitly recited as the limits of the range, but also to include all the individual numerical values or sub-ranges encompassed within that range as if each numerical value and sub-range is explicitly recited. To illustrate, a numerical range of "about 0.1% to 5%" should be interpreted to include not only the explicitly recited values of about 0.1% to about 5%, but also include individual values (e.g., about 1%, about 2%, about 3%, and about 4%) and the sub-ranges (e.g., about 0.5% to about 1.1%; about 5% to about 2.4%; about 0.5% to about 3.2%, and about 0.5% to about 4.4%, and other possible sub-ranges) within the indicated range.

As used herein, the terms "about," "approximate," "at or about," and "substantially" mean that the amount or value in question can be the exact value or a value that provides equivalent results or effects as recited in the claims or taught herein. That is, it is understood that amounts, sizes, formulations, parameters, and other quantities and characteristics are not and need not be exact, but may be approximate and/or larger or smaller, as desired, reflecting tolerances, conversion factors, rounding off, measurement error and the like, and other factors known to those of skill in the art such that equivalent results or effects are obtained. In some circumstances, the value that provides equivalent results or effects cannot be reasonably determined. In such cases, it is generally understood, as used herein, that "about" and "at or about" mean the nominal value indicated ±10% variation unless otherwise indicated or inferred. In general, an amount, size, formulation, parameter or other quantity or characteristic is "about," "approximate," or "at or about" whether or not expressly stated to be such. It is understood that where "about," "approximate," or "at or about" is used before a quantitative value, the parameter also includes the specific quantitative value itself, unless specifically stated otherwise.

As used herein, the term "effective amount" refers to an amount that is sufficient to achieve the desired modification of a physical property of the composition or material. For example, an "effective amount" of an anbitody refers to an amount that is sufficient to achieve the desired improvement or effect modulated by indicated component, material, compound or protein, e.g. achieving the desired level of binding with an analyte bound by the antibody. The specific level in terms of concentration or amount as an effective amount will depend upon a variety of factors avidity of the antibody, target analyte, desired level of assay sensitivity and the like.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including matters of logic with respect to arrangement of steps or operational flow; plain meaning derived from grammatical organization or punctuation; and the number or type of embodiments described in the specification.

While specific elements and steps are discussed in connection to one another, it is understood that any element and/or steps provided herein is contemplated as being combinable with any other elements and/or steps regardless of explicit provision of the same while still being within the scope provided herein.

It will be understood that certain features and subcombinations are of utility and may be employed without reference to other features and subcombinations. This is contemplated by and is within the scope of the claims.

Since many possible aspects may be made without departing from the scope thereof, it is to be understood that all matter herein set forth or shown in the accompanying drawings and detailed description is to be interpreted as illustrative and not in a limiting sense.

It is also to be understood that the terminology used herein is for the purpose of describing particular aspects only and is not intended to be limiting. The skilled artisan will recognize many variants and adaptations of the aspects described herein. These variants and adaptations are intended to be included in the teachings of this disclosure and to be encompassed by the claims herein.

The present disclosure provides a novel integrated entropy-based approach for diagnostic and prognostic applications. Genes implicated in bacterial stress responses have been used for predicting bacterial growth outcome under antibiotic treatment, with the objective to develop novel diagnostic methods. Current approaches are specific to a species or antibiotic, limiting their application in new settings. It is unclear if methods can be developed that predict bacterial fitness independent of strain, species or type of stress. The present disclosure provides a substantial RNA-Seq and experimental evolution dataset for 9 strains and species, under 16 antibiotic and several non-antibiotic stress conditions, and provides a predictive approach that is generalizable. As a point of comparison to previous work, gene-panel-based methods were first implemented and tested how accurately they can predict antibiotic mechanism of action, as well as the fitness outcome of the bacterial pathogen Streptococcus pneumoniae in the presence of antibiotics or under nutrient depletion. Although these methods do well when evaluated on data obtained for a specific species, factors including limited gene homology restrict their application to other species. In contrast, a novel generalizable method was developed around the observation that global transcriptional disorder seems to be a common stress response in bacteria with low fitness. This disorder was quantified using entropy, which is a specific measure of randomness, and it was found that in low fitness cases increasing entropy and transcriptional disorder results from a loss of regulatory dependencies. Using entropy as a single feature, the present disclosure provides that fitness and antibiotic sensitivity (i.e. minimum inhibitory concentration) predictions can be made that generalize well beyond training data. Furthermore, entropy-based predictions were validated in severn (7) species under antibiotic and non-antibiotic conditions. By demonstrating the feasibility of universal predictions of bacterial fitness, this work establishes the fundamentals for potentially new approaches in infectious disease diagnostics.

Figure 3A:
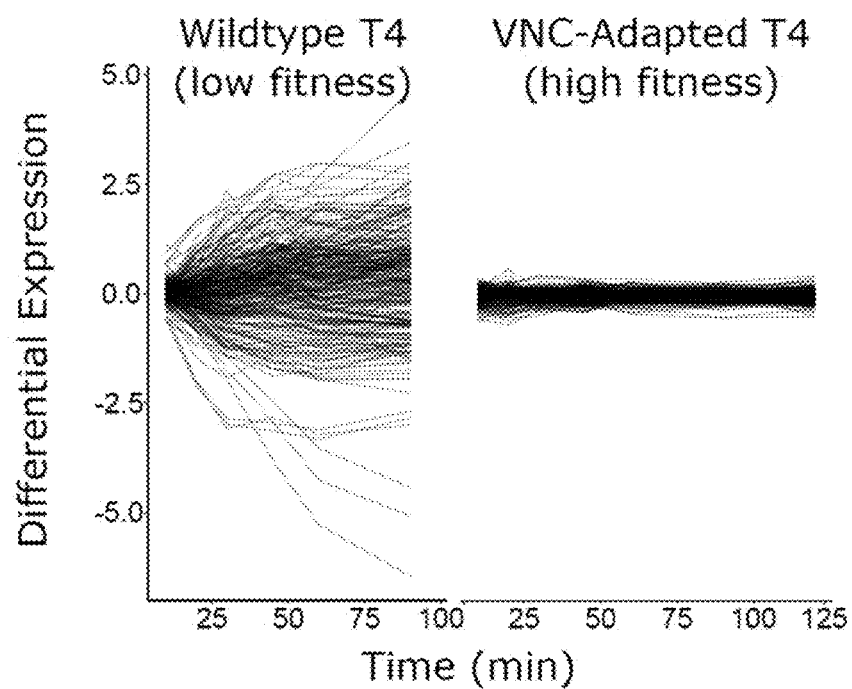
FIGS. 3A-3F. Transcriptomic disorder can be quantified by entropy, which predicts fitness.
Figure 3B:
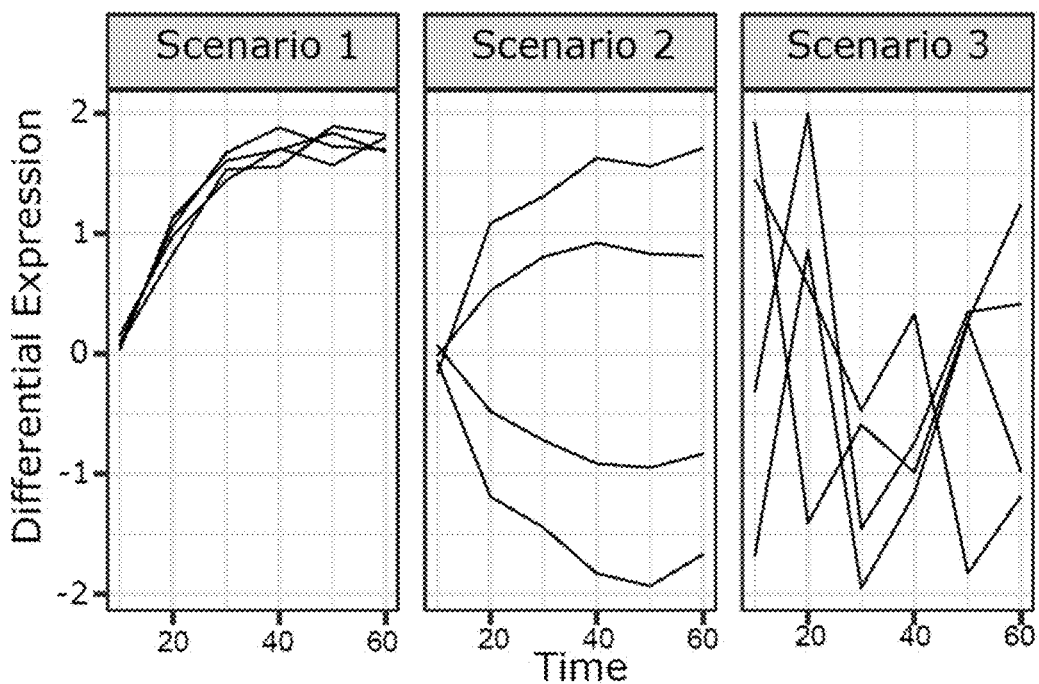
Figure 3C:
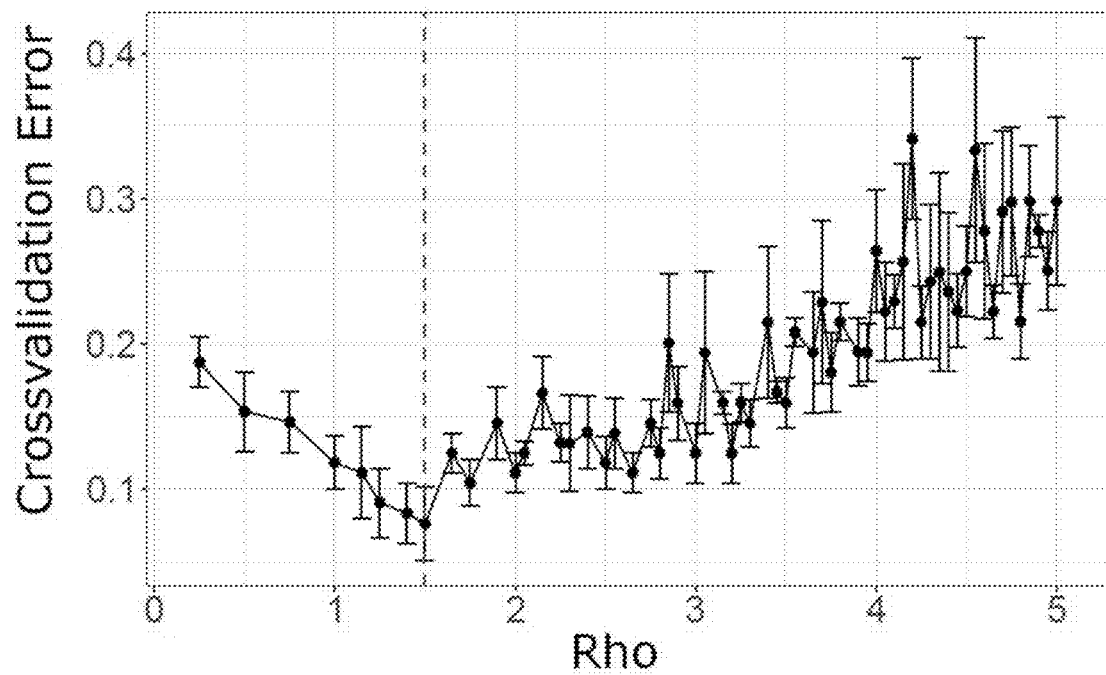

In certain embodiments, a major goal of this invention is to determine if there is a quantifiable feature that can accurately predict bacterial fitness in an environment, independent of strain, species or the type of stress. To be generalizable, the selected feature needs to be common across species and environments. By generating a large experimental dataset and analyzing published ones, the present disclosure provides that such a feature exists, namely transcriptomic entropy, which quantifies the level of transcriptional disorder while a bacterium is responding to the environment. It is important to realize that entropy is not simply a measure of large magnitude changes in the transcriptome. Instead, entropy takes into account condition-specific transcriptional dependencies among genes and quantifies the amount of independent changes. The underlying assumption is that gene expression patterns lose underlying dependencies and become more stochastic with increasing amounts of stress. The difference between simple measures of magnitude changes and more controlled measures of entropy is illustrated in FIG. 3B. The present disclosure provides that entropy is a flexible, and generalizable predictor of bacterial fitness in a variety of different environments, it can be used with time-course data or single-timepoint data and can even be used to predict the MIC of an antibiotic.

In certain embodiments, the presen disclosure provides current gene-panel based approaches for two reasons: 1) to search for a gene-panel that would capture a general stress-response (if it exists), and thus would represent a set of genes and associated regulatory changes coordinated by the same mechanisms in response to different types of stress. The existence of such a general response has been mostly connected to the manner in which rpoS responds to stress in E. coli and a small number of other species. However, it is largely unclear which genes respond downstream of rpoS, whether this response is accompanied by stress-specific responses, to what extent these transcriptional changes overlap across species and in response to different types of stress[16]. Moreover, if such a general stress response exists widely across species, it is unclear whether there is any predictive information to be extracted from it. Importantly, it was unable to identify such a gene-panel within the dataset generated for S. pneumoniae and other species, as well as in the published datasets explored; 2) As a point of comparison for the entropy-based approach. This comparison highlights that an entropy-based approach yields better performance than a gene-panel based approach (Table 8) and has at least 3 additional advantages over existing gene-panel approaches: a) It is independent of specific genes, whereas gene-panels focus entirely on specific genes. This might lead researchers to interpret genes present in a particular panel as those most relevant to the stress response. However, caution should be taken in the interpretation of these gene panels, because it turns out that the genes that appear in these panels are strongly influenced by model parameters ($\lambda$) and input data (FIGS. 1A-1G). b) An entropy-based method has few (at most 2) parameters, and therefore does not risk overfitting (unlike gene-based approaches, where there is at least one parameter per each transcriptionally measured gene). c) The entropy method generalizes across different antibiotic and non-antibiotic conditions, and across different species. This is not the case for gene-panel based methods, which can only make predictions on the same conditions as the data they were trained on (i.e. one model is predictive for a specific species and a specific antibiotic). And even though a gene-panel may only use expression of a limited number of genes to predict fitness and may therefore seem to be relatively easy to implement in a clinical setting, each new antibiotic-species combination requires the collection of an entirely new training dataset. This makes gene-panel approaches costly. Although the present disclosure focuses mainly on accuracy of fitness predictions, there are additional biological insights to be gleaned from the data presented. For instance, the inverse covariance matrix from Equation 1 represents a network that reveals regulatory interactions among genes. The covariance network inference using graphical-lasso regularization presented here is an improvement upon other methods (e.g. WGCNA[41]).

By demonstrating the feasibility of predictions of fitness outcomes and antibiotic sensitivity, several possibilities of integrating entropy-based predictions in a clinical diagnostic setting are envisioned. Currently, AST is often performed using culture-based methods. These methods may take days and even weeks for slow-growing species such as M. tuberculosis[42], delaying diagnosis and treatment in clinical settings. Therefore, it is desirable to be able to predict the fitness outcome of such slow-growing species as early as possible, for instance using RNA expression data. Another potential application of the entropy-based fitness predictions is monitoring an active infection in vivo. Performing transcriptome profiling and predicting the fitness of the infectious agent directly in its host environment allow for monitoring of disease progression and determining if and when treatment is necessary. Simultaneously profiling the pathogen and the host using dual RNA-Seq[43,44], and predicting the fitness of both is also valuable in assessing the state and progression of an infection.

Admittedly, direct implementation of RNA-Seq in diagnostic tests might not (yet) be practical, as RNA-Seq experiments still remain relatively expensive, labor-intensive and time-consuming. With the advent of real-time sequencing technologies, such as Nanopore, the speed of data collection may soon be improved significantly. Additionally, a transcriptome can be sub sampled by monitoring conserved genes across species. In this scenario, transcriptional entropy can be obtained via more economical gene expression technologies, such as NanoString nCounter[45] or the Luminex platform[46]. The present disclosure provides a novel approach that uses entropy to predicting fitness independently of gene-identity, gene-function, and type of stress. This approach can be applied as a fundamental building block for generalizable predictors of fitness and MICs for Gram-positive and negative species alike, and thereby possibly improve clinical decision-making.

Now having described the aspects of the present disclosure, in general, the following Examples describe some additional aspects of the present disclosure. While aspects of the present disclosure are described in connection with the following examples and the corresponding text and figures, there is no intent to limit aspects of the present disclosure to this description. On the contrary, the intent is to cover all alternatives, modifications, and equivalents included within the spirit and scope of the present disclosure.

B. EXAMPLES

The following examples are put forth so as to provide those of ordinary skill in the art with a complete disclosure and description of how the compounds, compositions, articles, devices and/or methods claimed herein are made and evaluated, and are intended to be purely exemplary of the disclosure and are not intended to limit the scope of what the inventors regard as their disclosure. Efforts have been made to ensure accuracy with respect to numbers (e.g., amounts, temperature, etc.), but some errors and deviations should be accounted for. Unless indicated otherwise, parts are parts by weight, temperature is in ° C. or is at ambient temperature, and pressure is at or near atmospheric.

The following examples are provided to illustrate embodiments of the present invention but are by no means intended to limit its scope.

The examples described herein will be understood by one of ordinary skill in the art as exemplary protocols. One of ordinary skill in the art will be able to modify the below procedures appropriately and as necessary.

Example 1

Gene-panel based methods can make fitness predictions across different antibiotics but are sensitive to input data and model parameters, and fail to generalize to previously unseen species Previously, the expression levels of specific genes have been used to predict susceptibility of a specific species under a specific antibiotic stress[8,11,23]. In contrast, the goal here is to identify a general predictor of fitness (presence or absence of growth) that does not only work for a specific stress or species, but instead extends to as many previously unseen settings (i.e. species and conditions) as possible. In line with existing approaches, a gene-panel that predicts fitness are generated. This panel, when trained on expression data coming from multiple stress conditions, can predict bacterial fitness for any condition (rather than a specific condition). Importantly, it is also able to assess, for the first time, how sensitive such models are to input data and model parameters. Below it first shows that gene-panel models indeed are highly sensitive to these factors and thereby have limited generalizability. Subsequently, an alternative approach is developed using entropy, that is generalizable, robust, and condition-agnostic (i.e. applicable to many conditions).

To test whether a gene-panel model can be trained that predicts fitness for many different conditions, a large RNA-Seq dataset was generated for the human pathogen Streptococcus pneumoniae. To produce transcriptomic response profiles from multiple stress conditions, S. pneumoniae strains TIGR4 (T4) and Taiwan-19F (19F) were grown in the presence or absence of 1× the minimum inhibitory concentration (MIC) of 16 antibiotics representing 4 mechanisms of action (MOA). These include cell wall synthesis inhibitors (CWSI), DNA synthesis inhibitors (DSI), protein synthesis inhibitors (PSI) and RNA synthesis inhibitors ((RSI); FIG. 1A, Tables 1 & 2). Each strain was exposed to each antibiotic for 2 to 4 hours and cells were harvested for RNA-Seq at various time points. As T4 and 19F are susceptible to most antibiotics used, the transcriptional profiles in the presence of antibiotics mostly represent cases of low fitness (FIG. 1A, sensitive strain, 1×MIC$_{WT}$). In order to find patterns that differentiate fitness outcomes, adapted strains were generated with increased fitness in the presence of antibiotics by serial passaging wildtype T4 and 19F in the presence of increasing amounts of antibiotics. Four independent adapted populations for each strain were selected on individual antibiotics. These adapted strains could grow in the presence of antibiotic at 1.5xMIC of the wildtype strain, albeit with a small growth defect (FIGS. 6A-6E & 6F). In parallel, RNA-Seq was performed on S. pneumoniae strains D39 and T4 in a chemically defined medium, and media from which either uracil, Glycine or L-Valine was removed, which are essential for D39 but not T4. This enabled the potential identification of a common stress signature that is shared between antibiotic exposure and nutrient deprivation, and across multiple strains. Lastly, D39 was adapted to grow in the absence of each individual nutrient, after which RNA-Seq was repeated for adapted clones (Table 1 lists all 24 strains, 67 populations and 267 RNA-Seq experiments).

Transcriptome data was separated into a training set for parameter fitting, and a test set. The test set includes a completely different set of antibiotic conditions, to enable proper evaluation of model performance on previously unseen data (Table 1). A condition-agnostic predictor of fitness was developed by fitting a regression model on the training set, which includes high and low fitness outcomes from 5 antibiotics (representing 4 MOAs), 3 nutrient depletion conditions, and from 3 S. pneumoniae strain backgrounds. Lasso-regularization was used in order to limit the number of features, thereby lowering the risk of overfitting the model (there are over 1500 genes in common for the 3 strains, therefore there are as many potential features that could be used)[25]. In order to avoid any bias in the selection of features, the regularization strength ($\lambda$) was automatically determined using crossvalidation analysis on the training data (FIG. 1B)[25,26]. The resulting model (which contains 28 genes and an intercept, Table 3) has an accuracy of 0.93 and 0.77 on the training and the unseen test set respectively (FIG. 1C & FIGS. 7A-7E, full performance statistics are in Table 8).

Figure 1B:
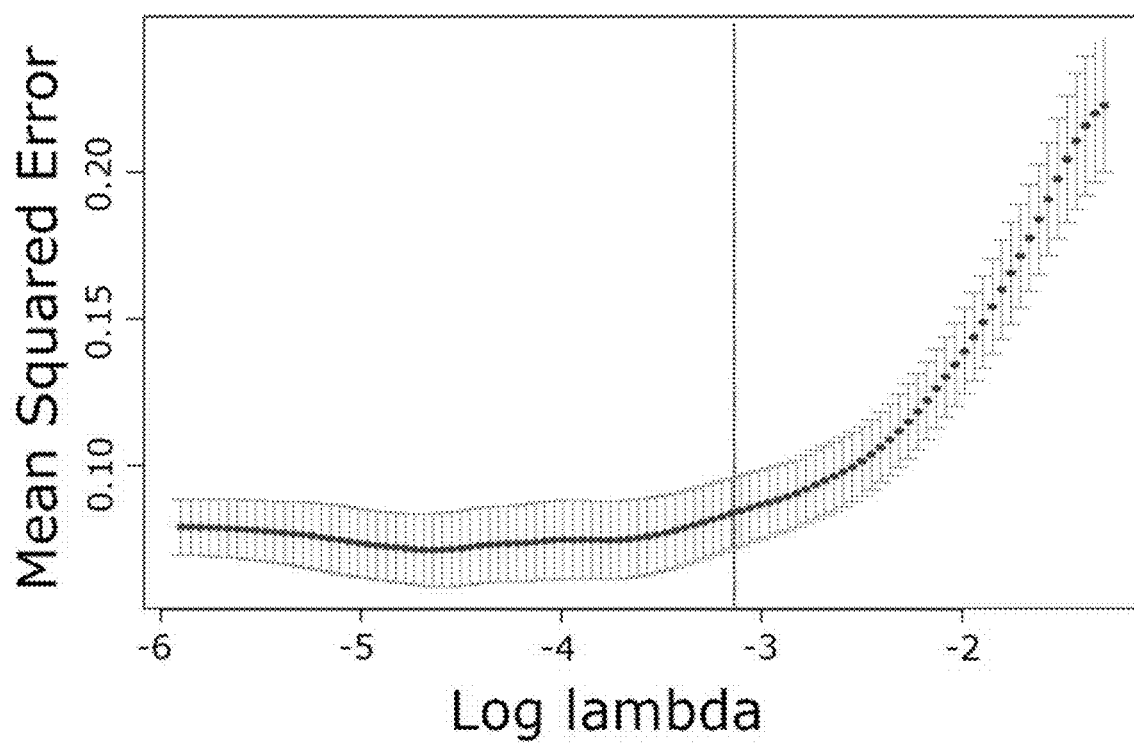
Figure 1C:
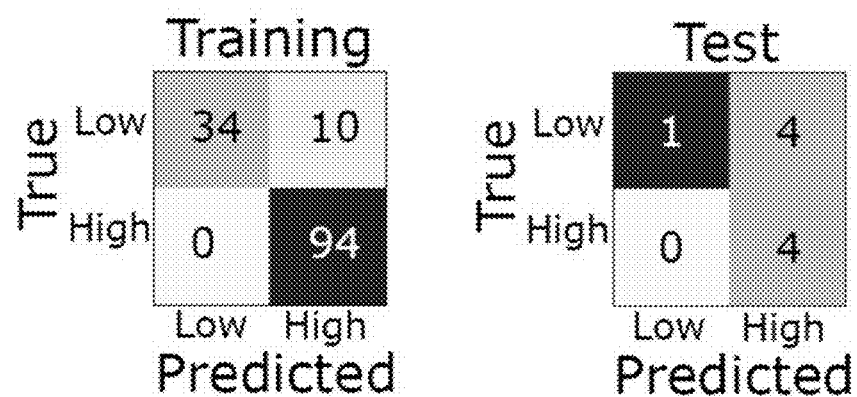
Figure 1D:
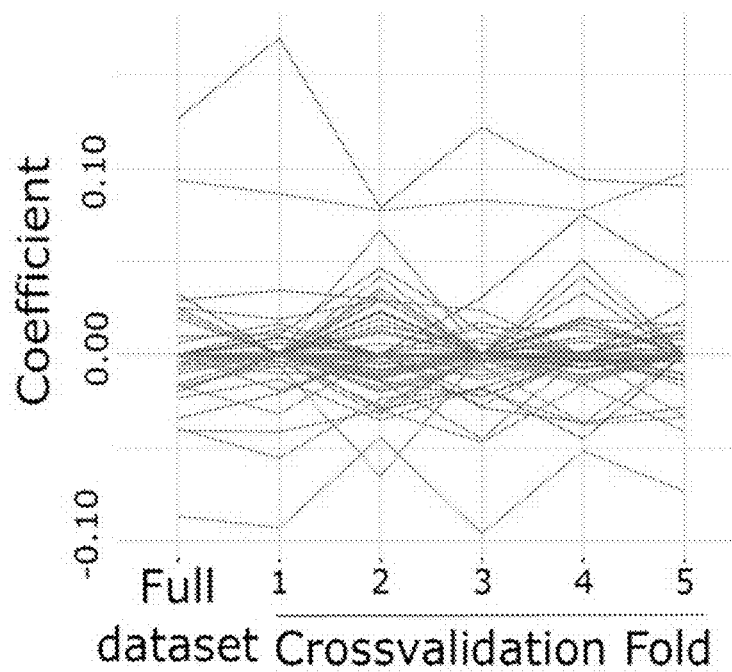
Figure 1E:
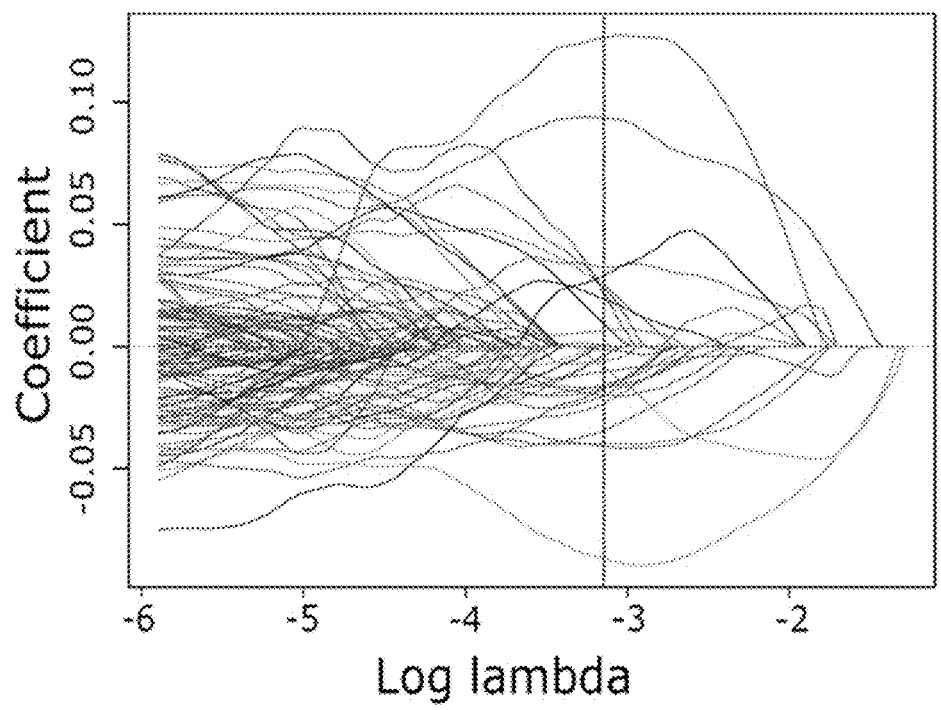
Figure 7A:
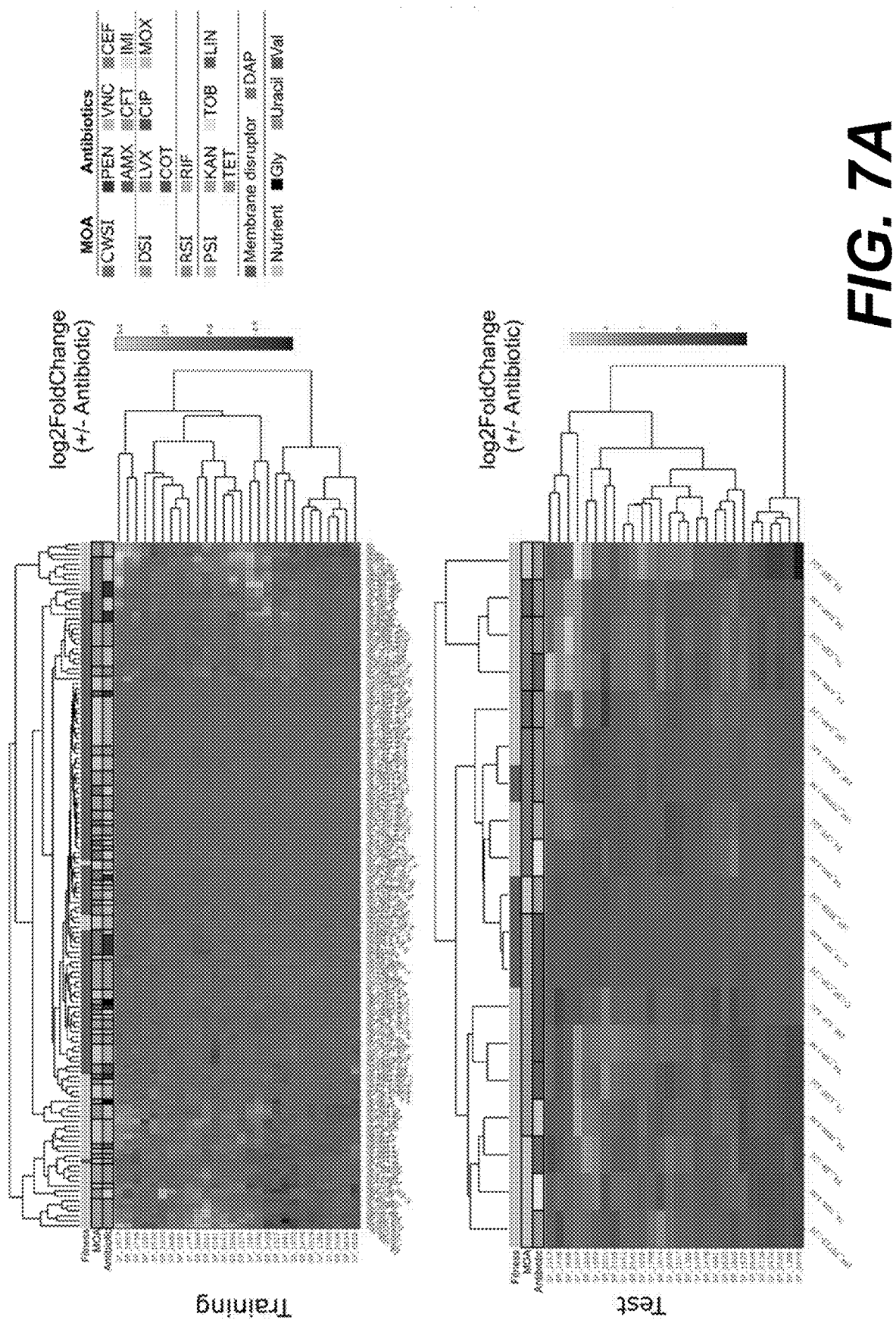
FIGS. 7A-7E. Performance and functional enrichment of the gene-panel that predicts fitness.
Figure 7B:
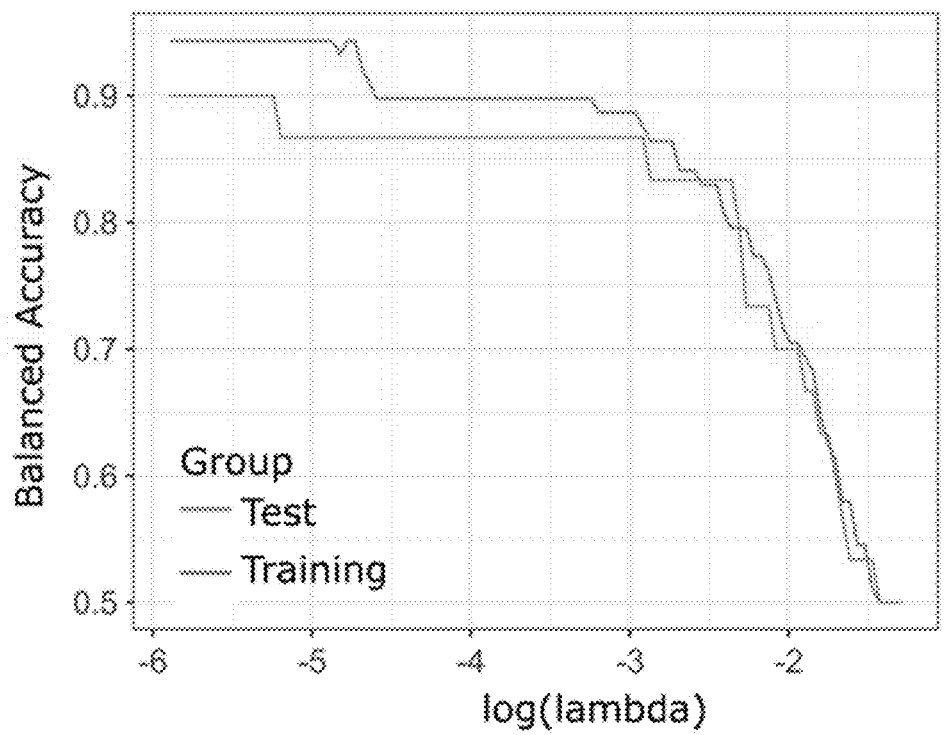
Figure 7C:
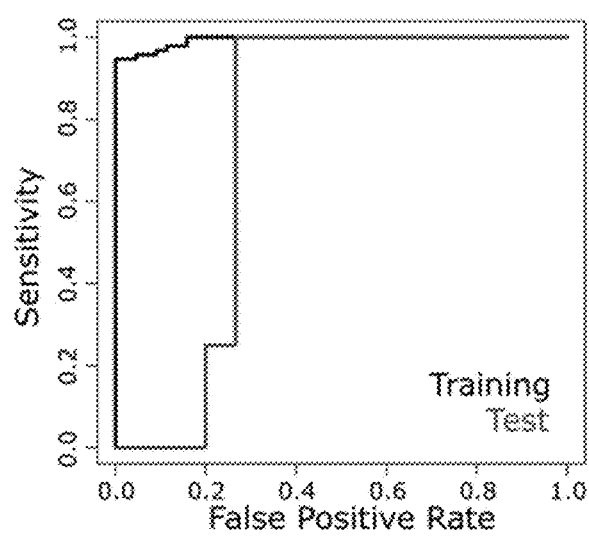
Figure 7D:
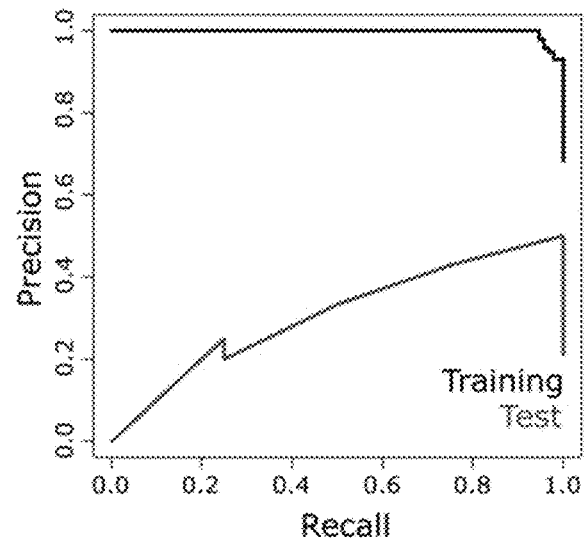
Figure 7E:
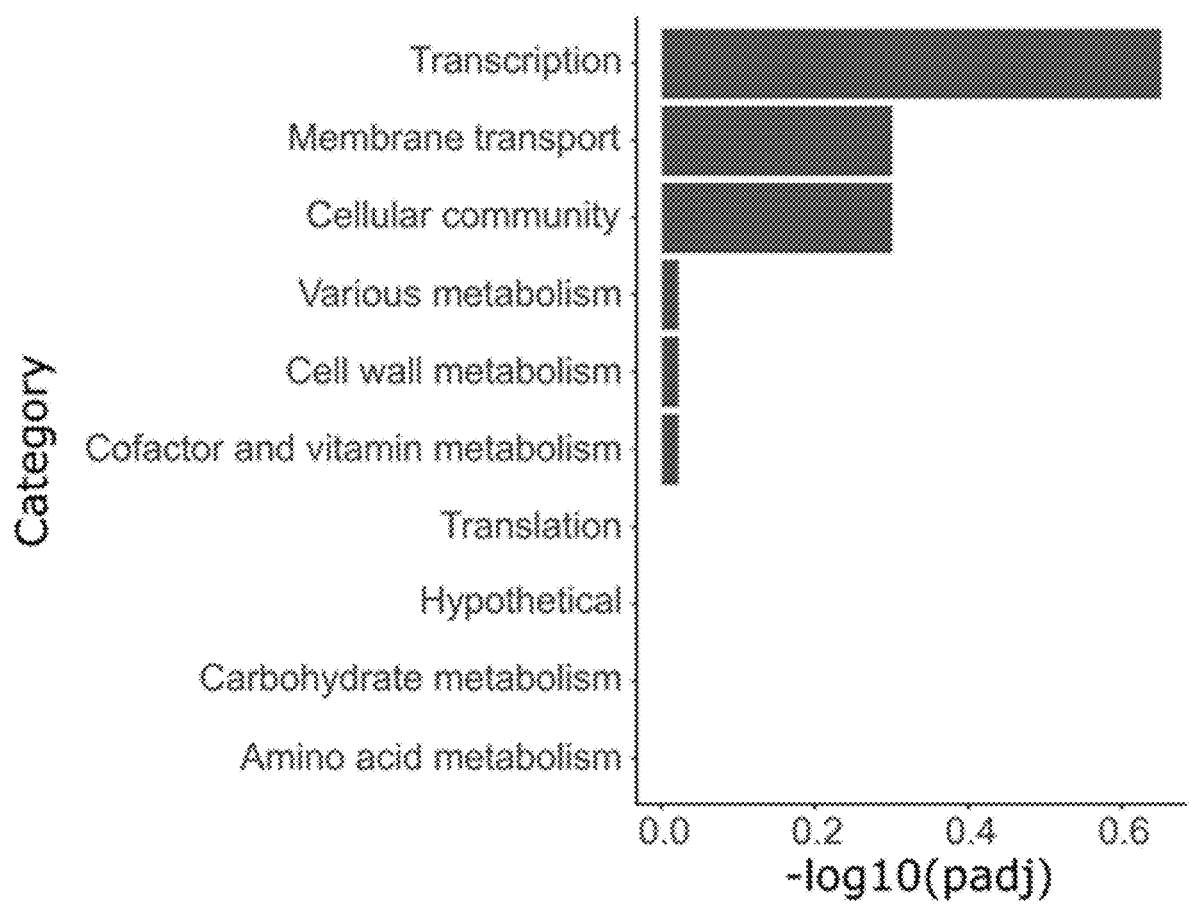
Figure 8F:
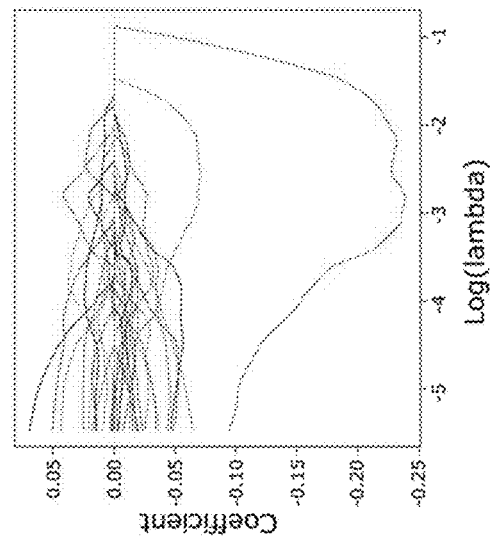
Figure 8H:
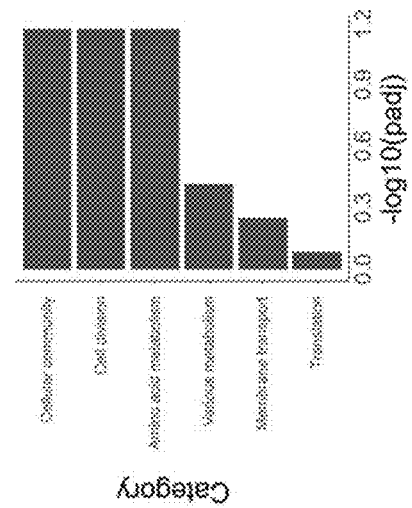
Figure 8E:
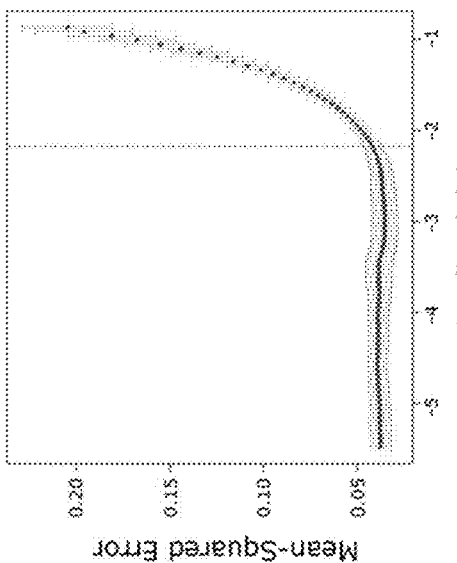
Figure 8G:
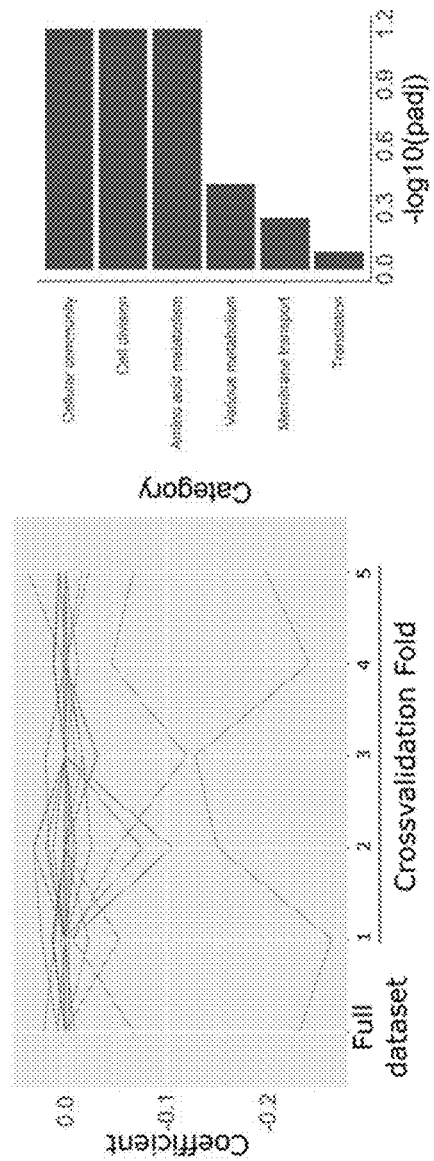
Figure 8J:
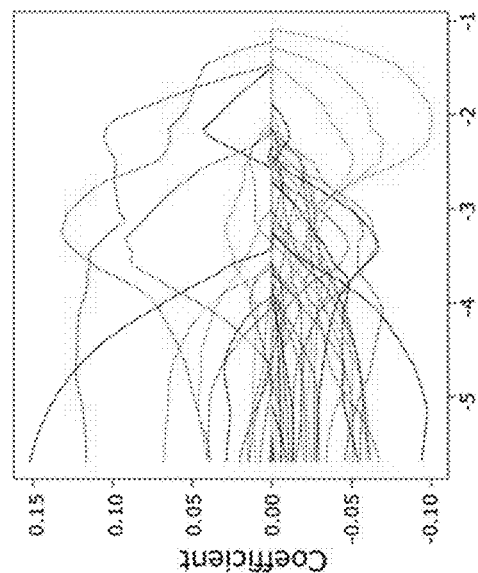
Figure 8I:
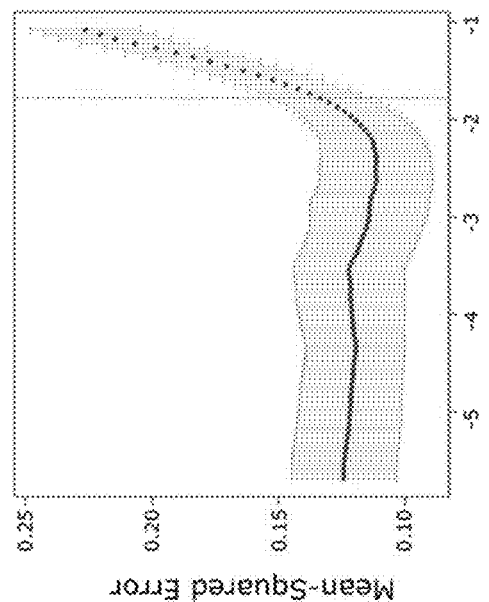
Figure 8L:
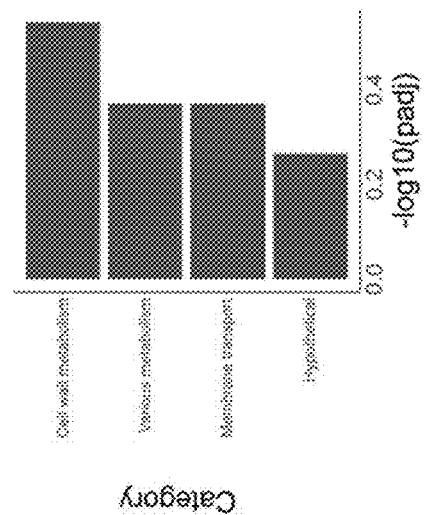
Figure 8K:
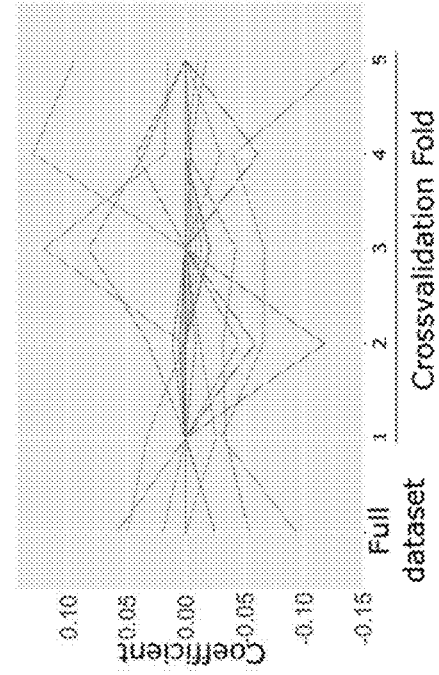

Fitness predictions that rely on the expression of specific genes are potentially influenced by the data used during training[23]. A model robust to input data would recover mostly the same features (i.e. genes) when small subsets of input are omitted during parameter fitting. In order to test the sensitivity of the regression model to input data, the same type of regression model was trained on 5 different subsets of the training dataset, each time omitting a different 20% of the data. The features included and their coefficients varied greatly in these experiments (FIG. 1D), with only 5 out of 28 genes in the model common to all iterations of model fitting. To assess sensitivity of the gene-panel to the regularization strength (i.e. $\lambda$), the same model was trained using different values for $\lambda$. While the coefficients of individual genes vary drastically (FIG. 1E), the performance at different values of $\lambda$ remains similar (FIG. 1B & FIG. 7B). This indicates that there are genes that contain similar information for classification purposes and are interchangeable. This means that the gene-panel approach is sensitive not only to input data, but also to model parameters. This work is the first to demonstrate how much gene-panels can be affected by both of these factors. An implication of this sensitivity is that the genes in a gene-panel that are selected in an automatic fashion can be influenced by how the model is trained. Therefore, interpreting these genes as the determinant biological factors for fitness can be problematic. Furthermore, enrichment analysis reveals there are no significantly enriched functional categories in this gene-panel (FIG. 7E). This suggests that a gene-panel is not a suitable approach for developing a condition-agnostic model, since no specific common response to different stresses can be detected that separates low fitness cases from high fitness ones.

While a condition-agnostic gene-panel is sensitive to input data and model parameter $\lambda$, it remains to be seen whether condition-specific models suffer from the same issue as well. For three MOA's for which the data were generated for multiple antibiotics (CWSI, DSI, and PSI), regularized regression models were trained (Table 4), and the models' sensitivities to input data and $\lambda$ were evaluated. In all 3 cases, the models change with input and $\lambda$, and show no enrichment for specific functional categories (FIGS. 8A-8L). In contrast, some published gene-panels[11] have shown functional enrichment. However, this is likely because the published gene-panels have been developed for single antibiotics. Therefore, the genes in those panels are highly selective for the species-specific response that is triggered in a particular stress. In contrast, in this work, predictors that differentiate high and low fitness cases for multiple stresses were identified. The fact that there is no enrichment on the gene-panels is suggestive of a lack of a general response, characterized by a set of specific genes, that gets triggered under many different circumstances.

Besides a lack of functional enrichment, neither the MOA-specific nor the condition-agnostic gene-panels developed here include genes that are known direct-targets of the antibiotics used. Moreover, in addition to being sensitive to input data and regularization strength, the condition-agnostic fitness gene-panel is limited in its applicability to other species, as genes in this panel lack homologs in other Gram-positive as well as Gram-negative species (FIG. 1F, Table 5). In fact, this homology problem is a limitation of previously published gene-panels as well (FIG. 1G, Table 5). Gene-panel based models therefore not only require re-training for each new condition, but also when they are to be implemented for a new species. This shows that gene-panel approaches in general not only need to be applied and interpreted with caution, but there is also no good evidence to expect that they can be turned into a generalizable fitness predictor that is both species and condition-agnostic.

Example 2

Figure 2A:
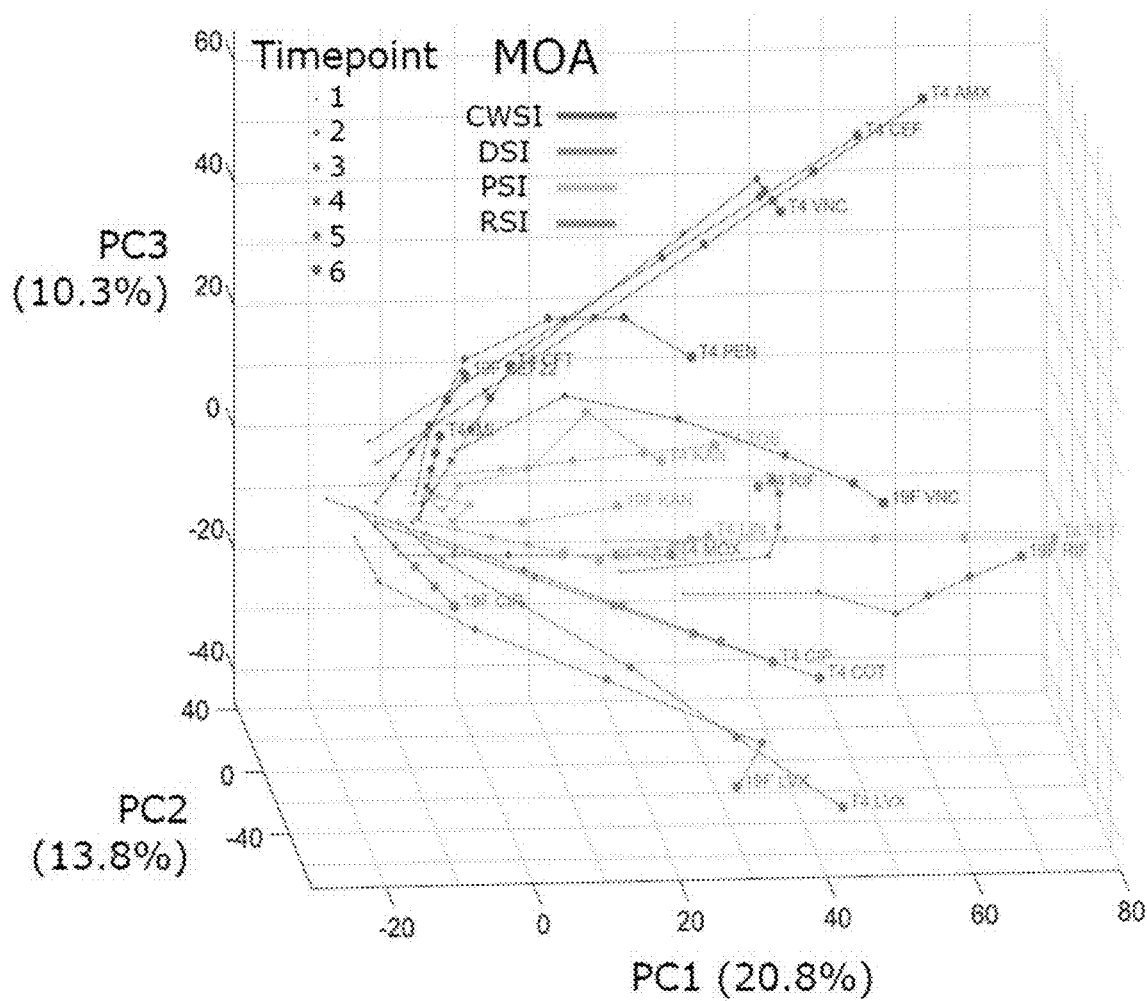
FIGS. 2A-2C. Transcriptional responses separate antibiotics with different mechanisms of action.
Figure 2B:
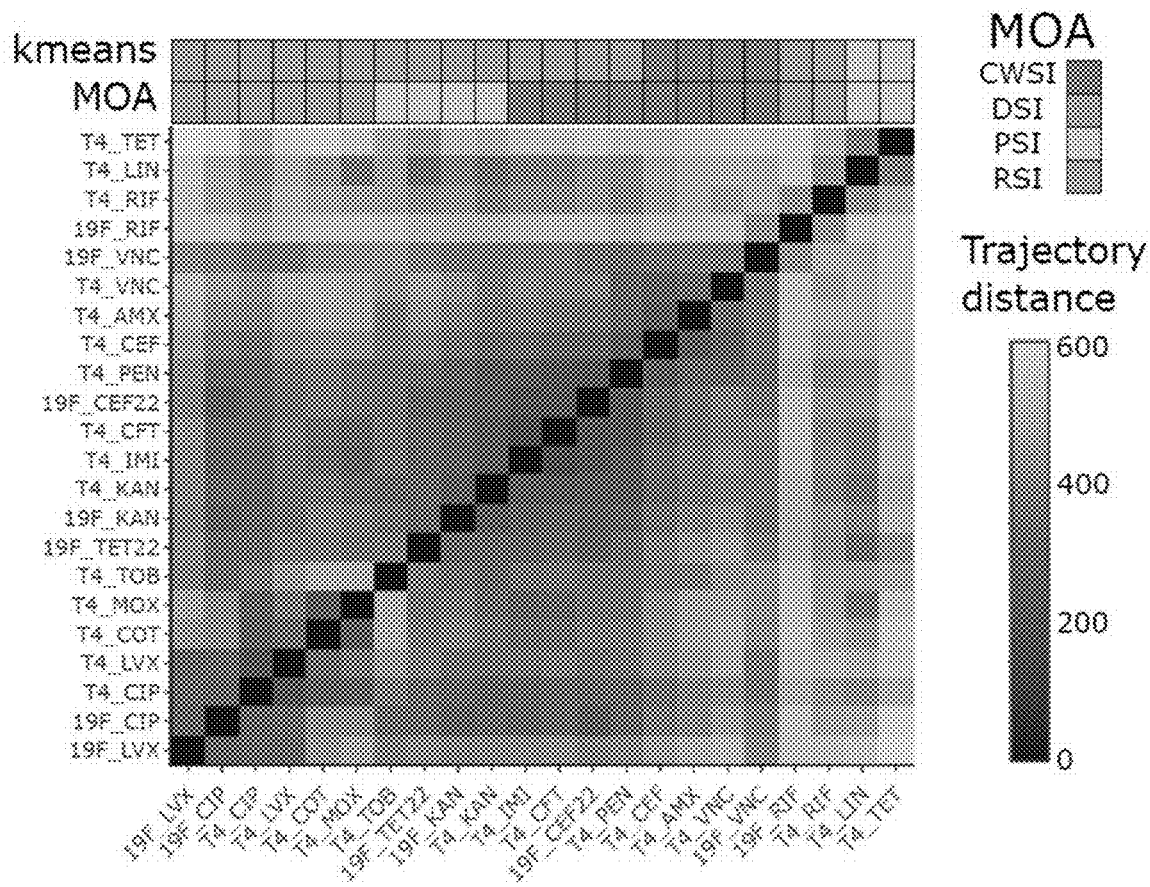

Building a universal predictor for fitness based on transcriptional responses is challenging because antibiotics trigger distinct responses based on their mechanisms of action One of the reasons why it may be non-trivial to produce a condition-agnostic model is because the different conditions (i.e. MOA's of different antibiotics) trigger such distinct responses that it is unlikely to identify a common signature among them. To determine whether responses from different antibiotics that fall under the same MOA cluster together, principal component analysis (PCA) was performed on the complete differential expression dataset. Each experiment is presented as one trajectory, connecting individual timepoints within that experiment (FIG. 2A). K-means clustering of all experiments' trajectories showed that transcriptional responses to drugs within the same MOA tend to follow similar trajectories over time (FIGS. 2A & 2B).

Figure 2C:
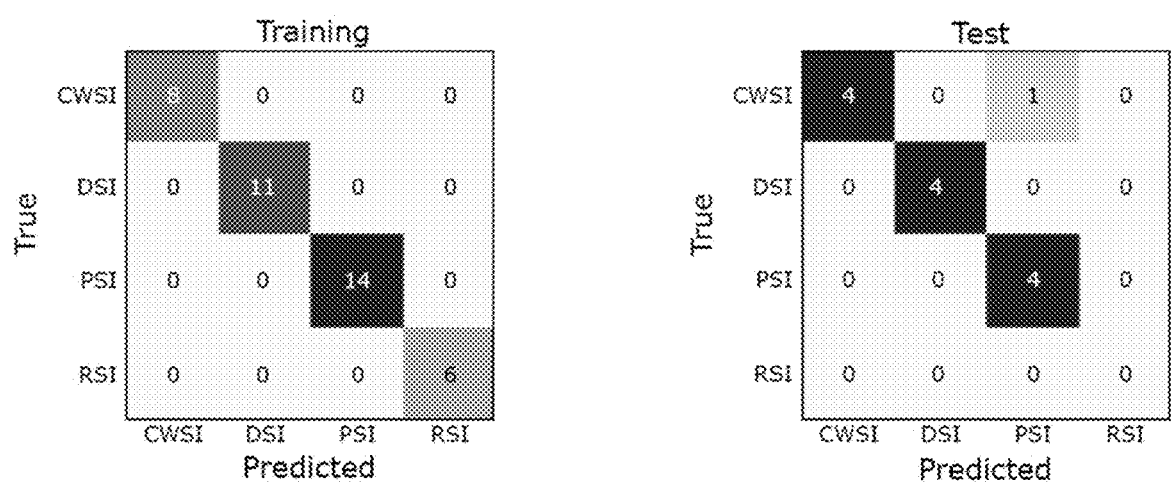
Figure 9A:
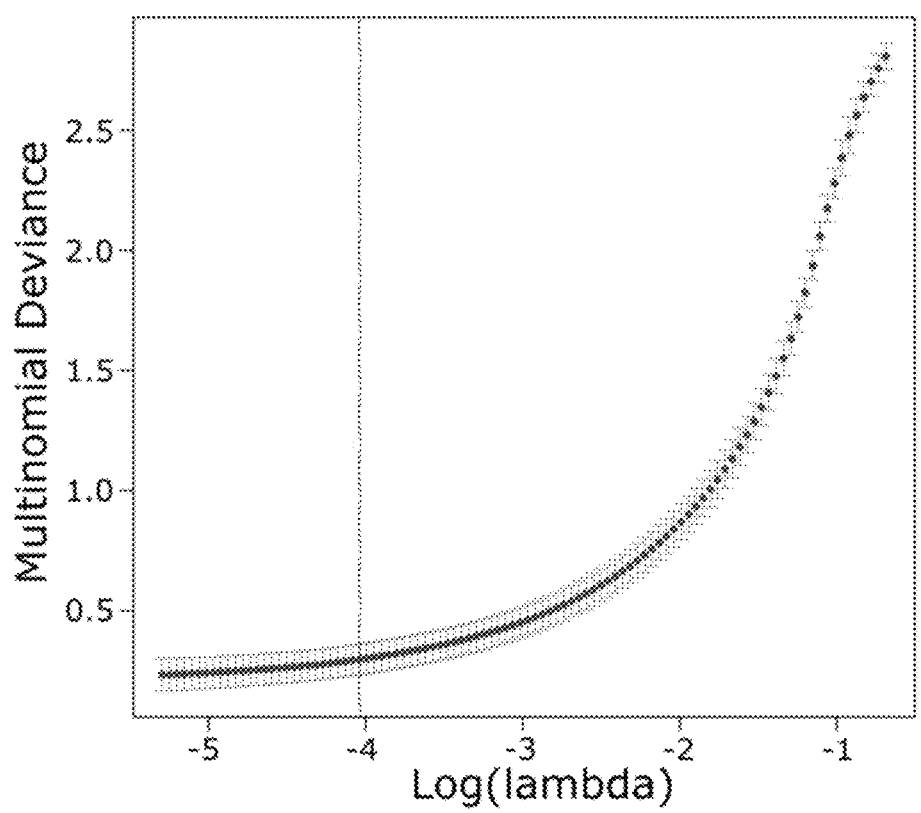
FIGS. 9A-9E. Performance of the gene-panel that predicts MOA.
Figure 9B:
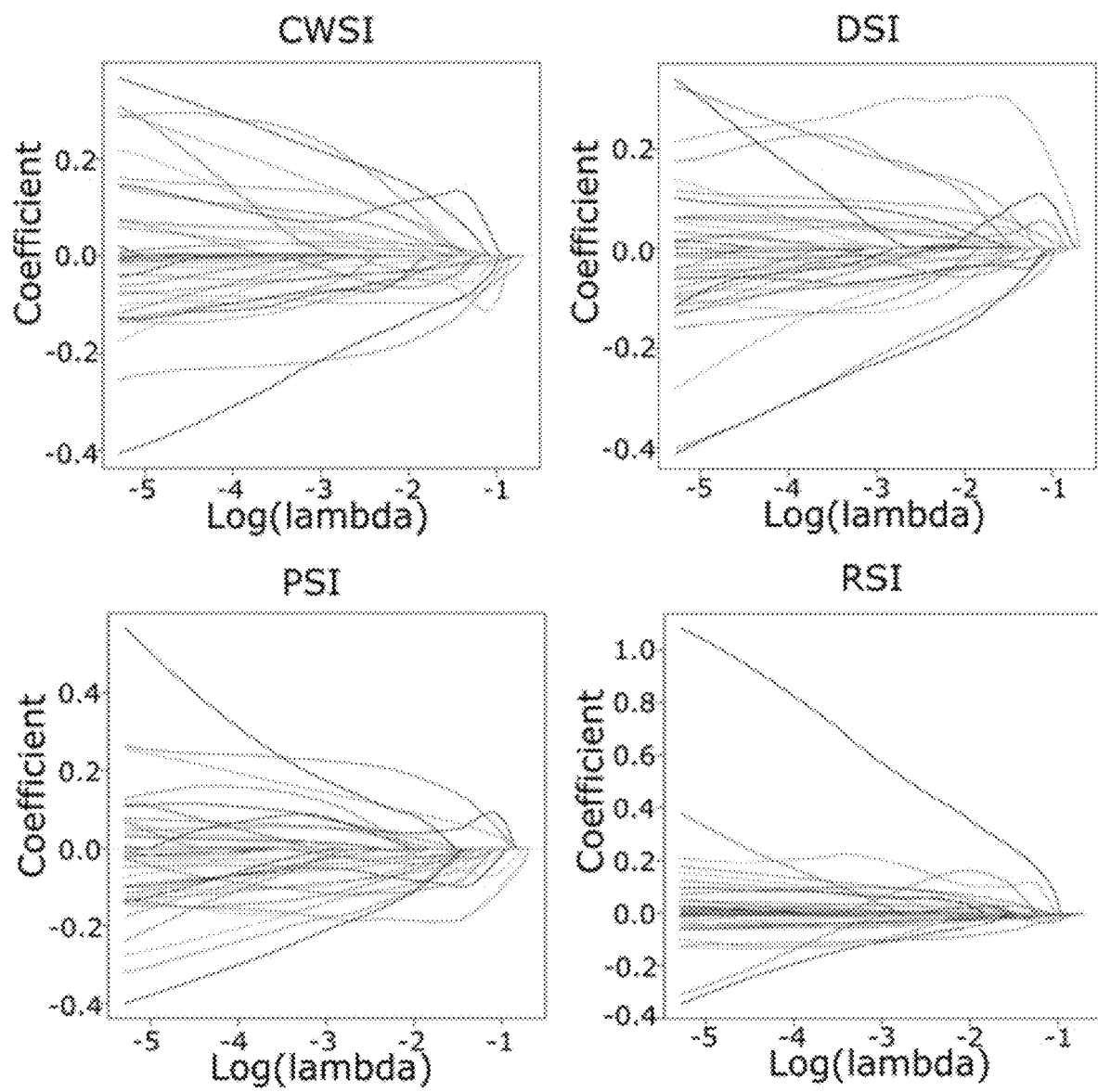
Figure 9C:
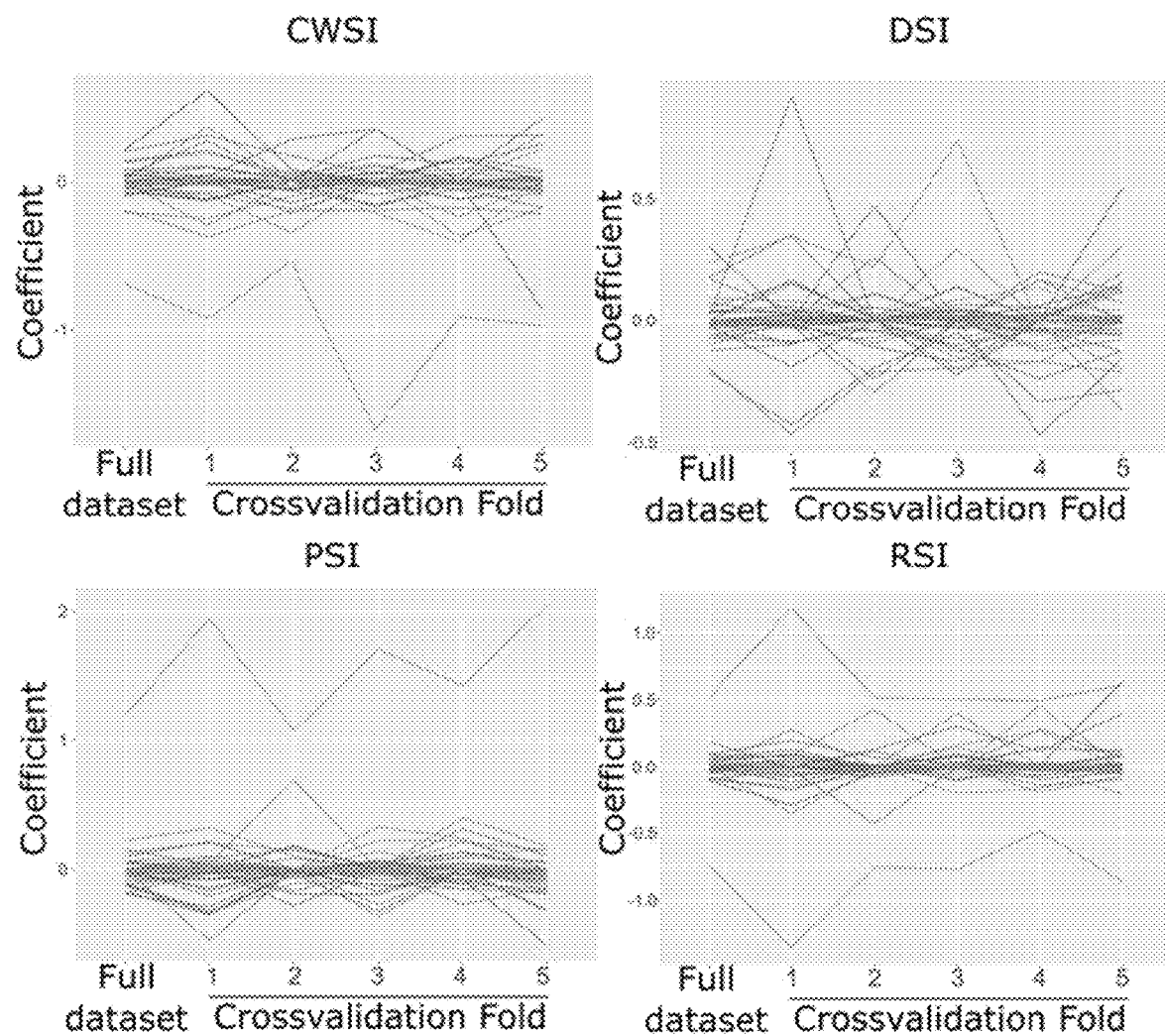
Figure 9D:
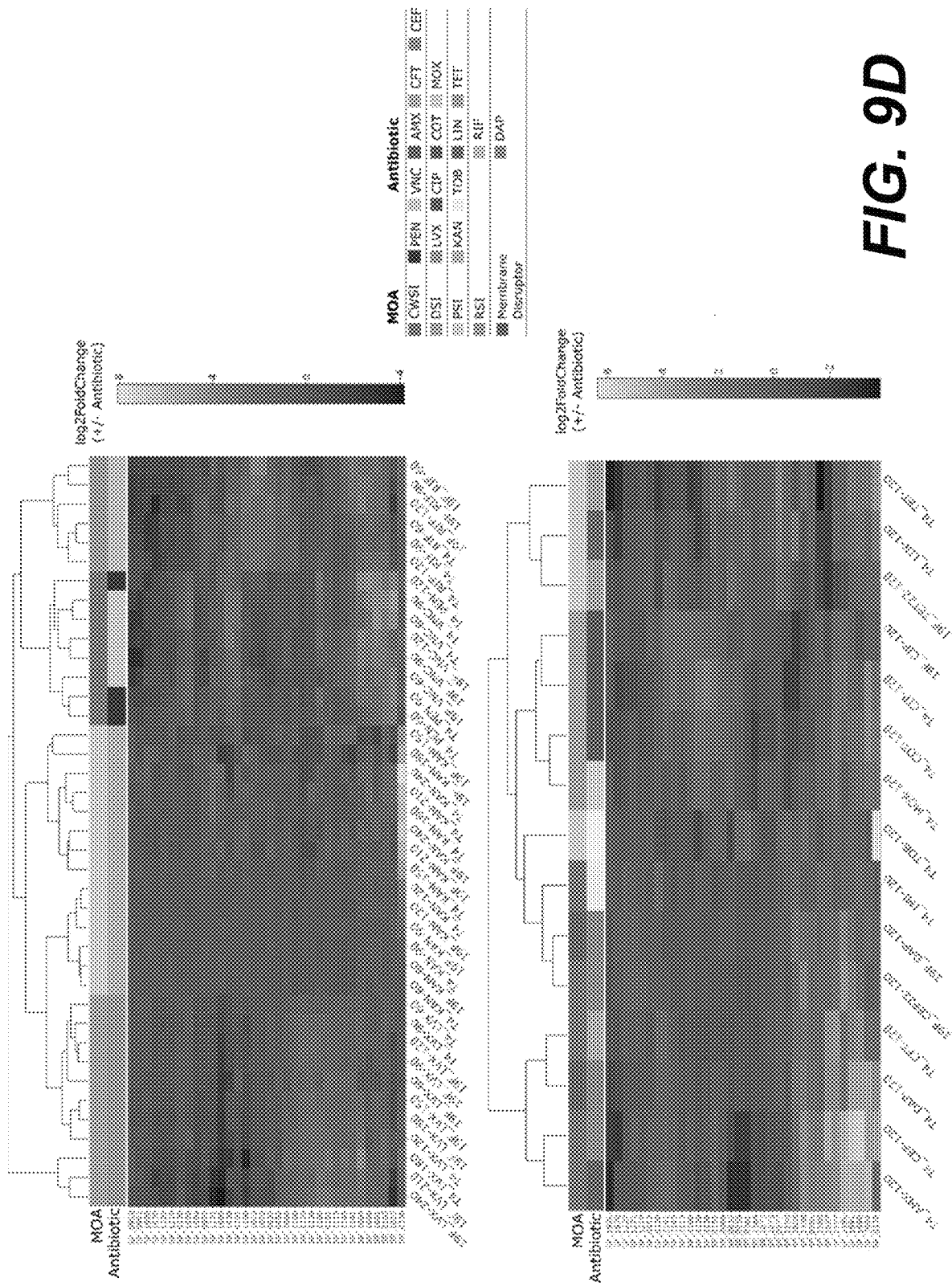
Figure 9E:
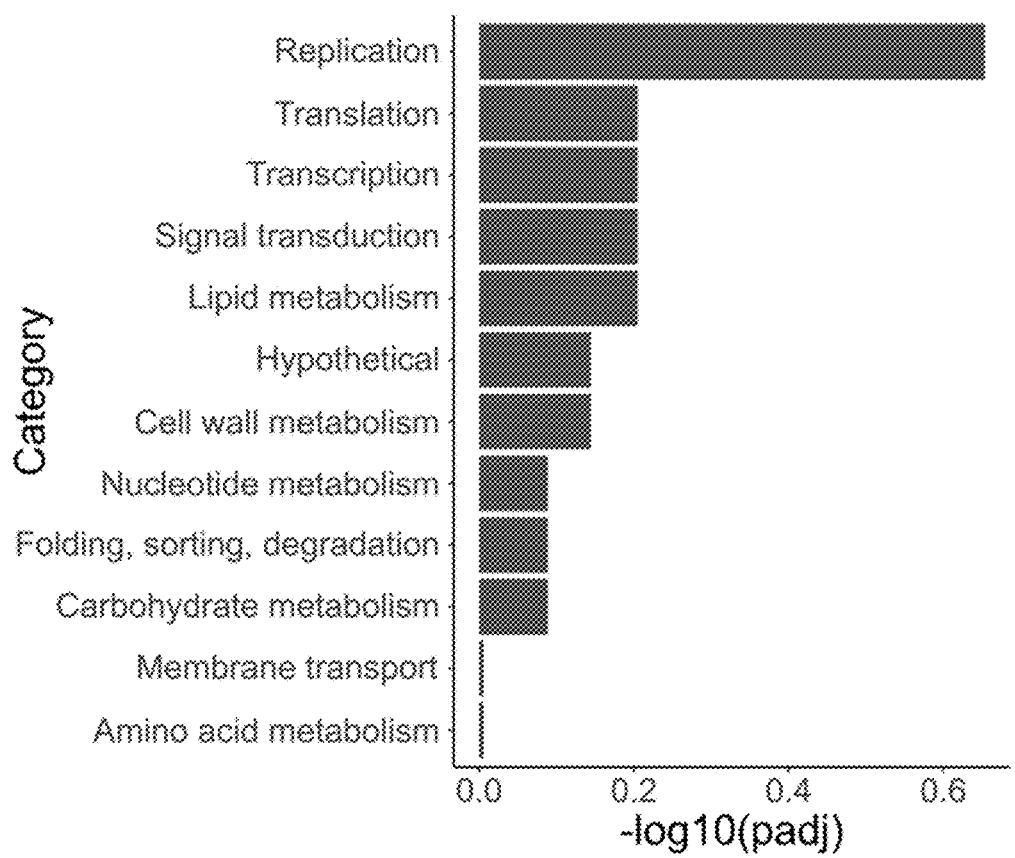

To further analyze whether different MOA's trigger different responses, a multi-class logistic regression model was fit on the training dataset and evaluated on the test set. If a simple classifier can successfully distinguish between different MOA's, this would imply that there are discriminating signals specific to each MOA. Similar to the fitness prediction, the regularization parameter was selected via a principled automatic procedure (without making any arbitrary decisions) to avoid overfitting. (FIG. 9A). This simple regression model is able to classify MOA's with an accuracy of 1 on the training set, and with only a single misclassification in the test set (FIG. 2C & FIG. 9D). Similar to the fitness panel, enrichment analysis of the 34 genes in this MOA panel reveals no significantly enriched functional categories (FIG. 9E). While some of the genes in the panel are relevant to the action of specific antibiotics, it is not immediately evident how each individual gene is relevant for the classification. For instance, DNA gyrase A (SP_1219) appears in the MOA panel (Table 6) and is a direct target of fluoroquinolones LVX and CIP, belonging to the class DSI. However, it is downregulated to a higher extent under both RSI compared to DSI stress, and thus does not have much discriminating power on its own (FIG. 9D). Compared to the fitness prediction panel, the features in the MOA panel are more robust to parameter tuning (FIG. 9B), and to input data (FIG. 9C). This suggests that MOA prediction is an easier task than fitness prediction using existing gene-panel approaches. Previous studies have demonstrated it is possible to train a classifier that predicts MOA from whole transcriptome data[27,28]. However, the gene panel presented in this section is the first model that predicts MOA based on a few genes. This model could therefore be implemented to classify the MOA of novel antimicrobials, without having to profile the entire transcriptome.

Example 3

Figure 10:
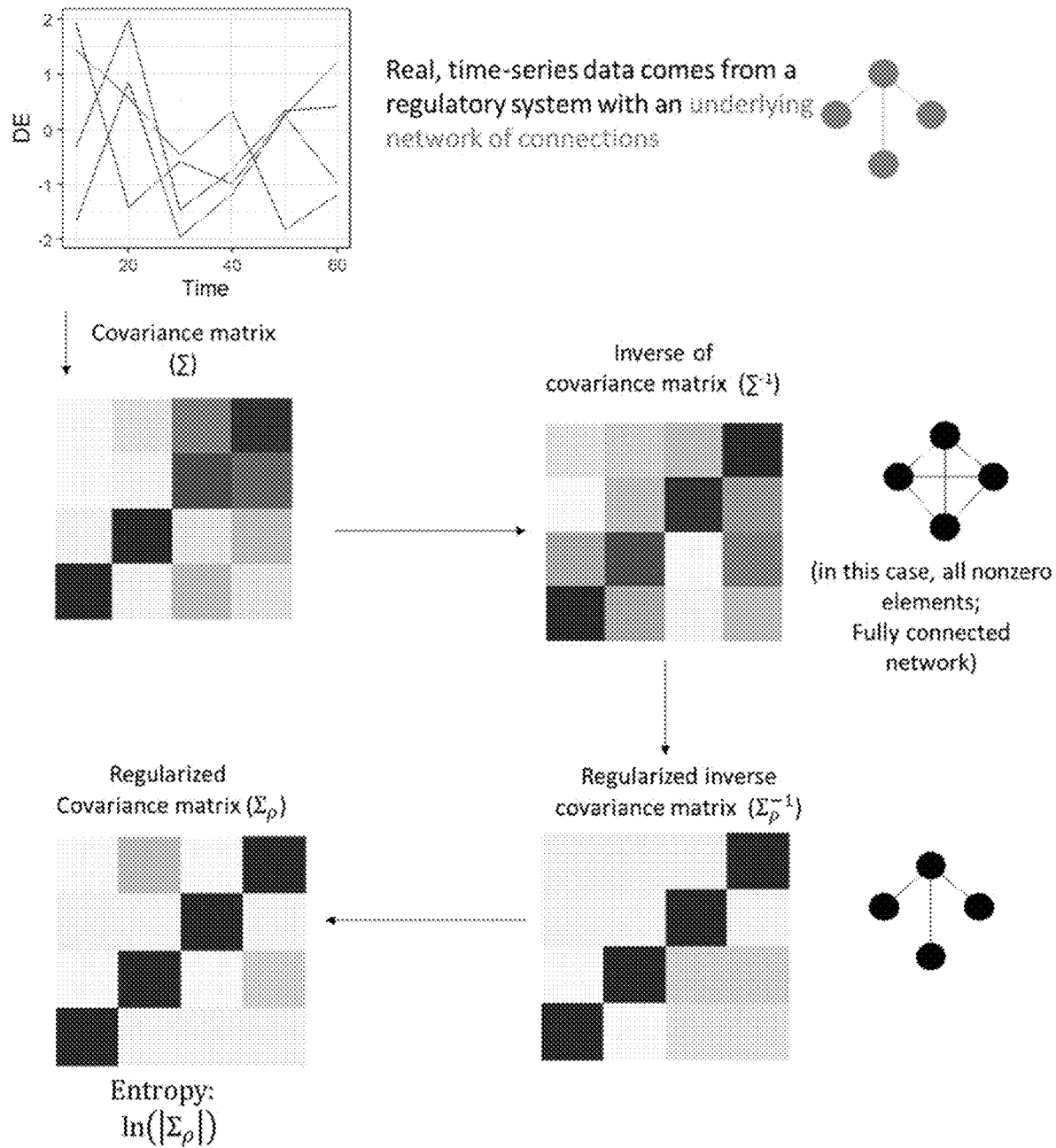
FIG. 10. Schematic demonstrating how entropy is computed from time-series DE data. The observable DE patterns are assumed to be influenced by condition-specific networks of interactions among genes. These interactions are unknown but can be inferred from the covariances among genes. Entropy quantifies disorder on a transcriptome, taking into account these interactions. In order to achieve this, the covariance matrix ($\Sigma$) across genes was first computed, and its inverse ($\Sigma^{-1}$) was taken. The support of this inverse covariance matrix yields a dense network, which is the "uncorrected" version of the real coexpression network. Since the real network is assumed to be sparse, graphical lasso was applied to retrieve a sparse network $\Sigma_\rho^{-1}$, and the resulting matrix ($\Sigma_\rho$) was inverted. Entropy is defined as the logarithm of the determinant of this matrix.

Reimagining statistical entropy as a measurement of transcriptional disorder leads to a flexible fitness predictor While the practical application of the MOA model may be useful, the main goal of this example is to build a versatile toolbox for fitness predictions that does not have many parameters to tune, does not rely on specific genes, and therefore possibly has improved generalizability compared to gene-panel models. To accomplish this, the following observation that we made in the data presented in this work, as well as in previously published studies[11,12,23,29] were focused on: bacteria with low-fitness in a given condition trigger larger, and seemingly more chaotic gene expression changes than those with high fitness (FIGS. 3A & 3B). Since these characteristics can be observed for many different stress-types and species, it could possibly be turned into a generalizable predictor of fitness if appropriately captured. Importantly, these types of patterns in the data evoke statistical entropy, which captures the amount of disorder in a system (FIG. 3B & FIG. 10). This example provides that with increasing amounts of stress (i.e. when the fitness of the bacterium is lowered), the bacterium experiences increasing amounts of dysregulation, resulting in a loss of dependencies in expression among genes. A loss of such dependencies results in more and more genes changing in expression independently (and perhaps seemingly randomly), resulting in an increase in entropy. Based on this idea, quantify the amount of disorder in a transcriptomic response by computing entropy was aimed. To predict fitness, a simple decision rule was then used on a single feature, which avoids overfitting, where entropy higher than a threshold t predicts low fitness, and entropy lower than t predicts high fitness.

To calculate entropy on a transcriptomic dataset with multiple timepoints, the classical statistical concept of entropy (H) is redefined as follows:

$$H = ln(|\Sigma \rho|) \quad (1)$$

Where $\Sigma$ is the empirical covariance matrix ($\Sigma_{ij}$ is the empirical covariance of $gene_i$ and $gene_j$ computed from the time series data), and $|\Sigma|$ denotes the determinant of $\Sigma$[30-33]. $\Sigma_{92}$ is a graphical-lasso regularized $\Sigma$, where $\rho$ denotes the regularization strength.

Entropy is computed from experiments with multiple timepoints as follows. 1) The temporal differential expression (DE) data is used to compute a gene-gene empirical covariance matrix $\Sigma$. 2) Graphical lasso[34] is applied to $\Sigma$ to obtain a regularized inverse of this covariance matrix ($\Sigma_\rho^{-1}$). The matrix $\Sigma_\rho^{-1}$ represents a network of dependencies of the regulatory interactions of the genes. 3) The inverse of this matrix ($\Sigma_\rho$) can then be used in Equation 1 to compute entropy (FIG. 10).

It is important to note that, with the described approach, a high entropy response reflects large changes in magnitude in the transcriptome that come from independently responding genes. This means that large changes in magnitude can still result in low entropy, when changes in expression are synchronized among genes (FIG. 3B). Synchronization thus comes from dependencies between genes, for instance due to regulatory interactions, which can vary based on the condition. Here, it is assumed that there is a sparse network of such dependencies (i.e. regulatory interactions), which are specifically determined for each experimental condition. These regulatory interactions for each experiment are inferred by computing a covariance matrix $\Sigma$ from temporal DE data. The inverse of this covariance matrix ($\Sigma^{-1}$) is interpretable as the (condition-specific) regulatory interaction network, where gene pairs have a zero value on $\Sigma^{-1}$ when their expression patterns are not directly dependent on each other. Like most biological networks, the condition-specific regulatory interaction network is expected to be sparse[35-37]. However, raw values on $\Sigma^{-1}$, empirically measured using RNA-Seq data, are mostly non-zero, resulting in a dense network, potentially due to noise in data collection. Regularization is thereby applied on $\Sigma^{-1}$ to estimate a de-noised, sparse network of interactions $\Sigma_\rho$, more likely to represent real, biologically relevant regulatory dependencies.

Figure 3D:
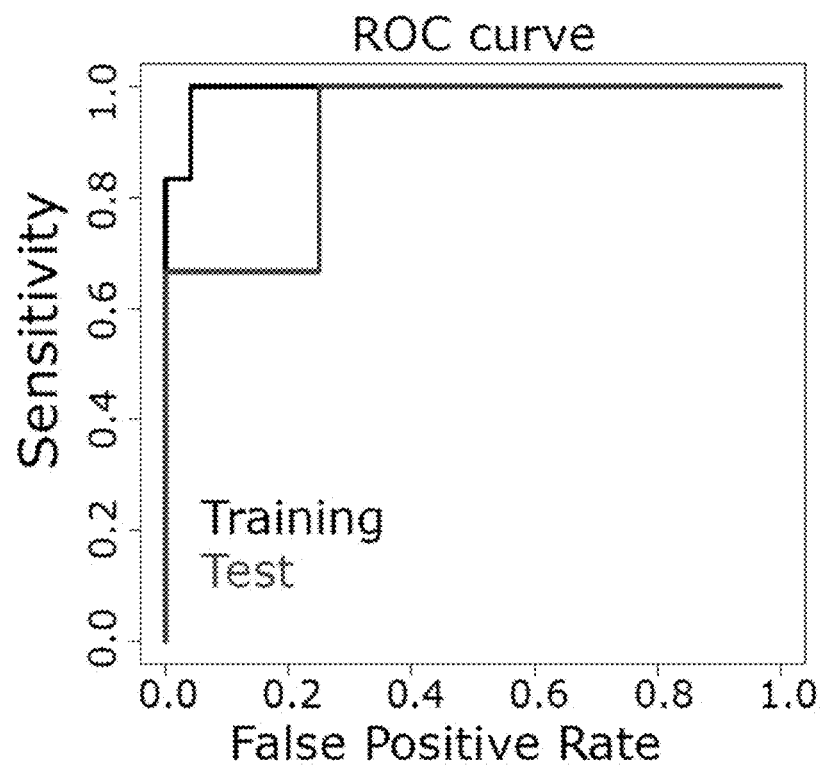
Figure 3E:
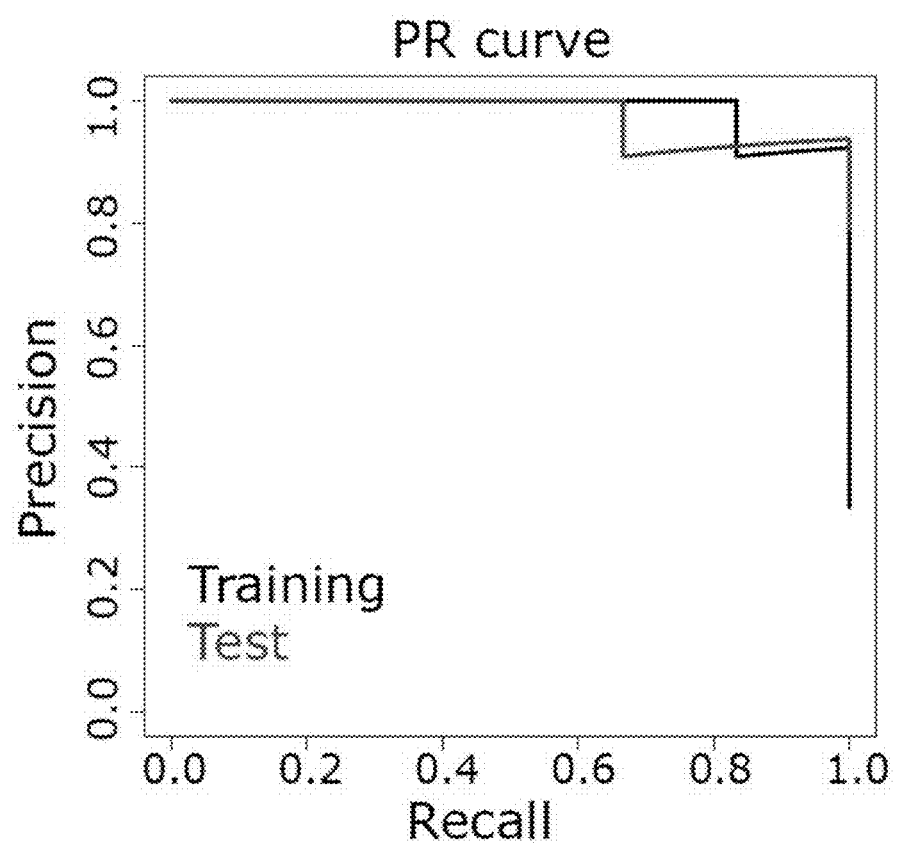
Figure 3F:
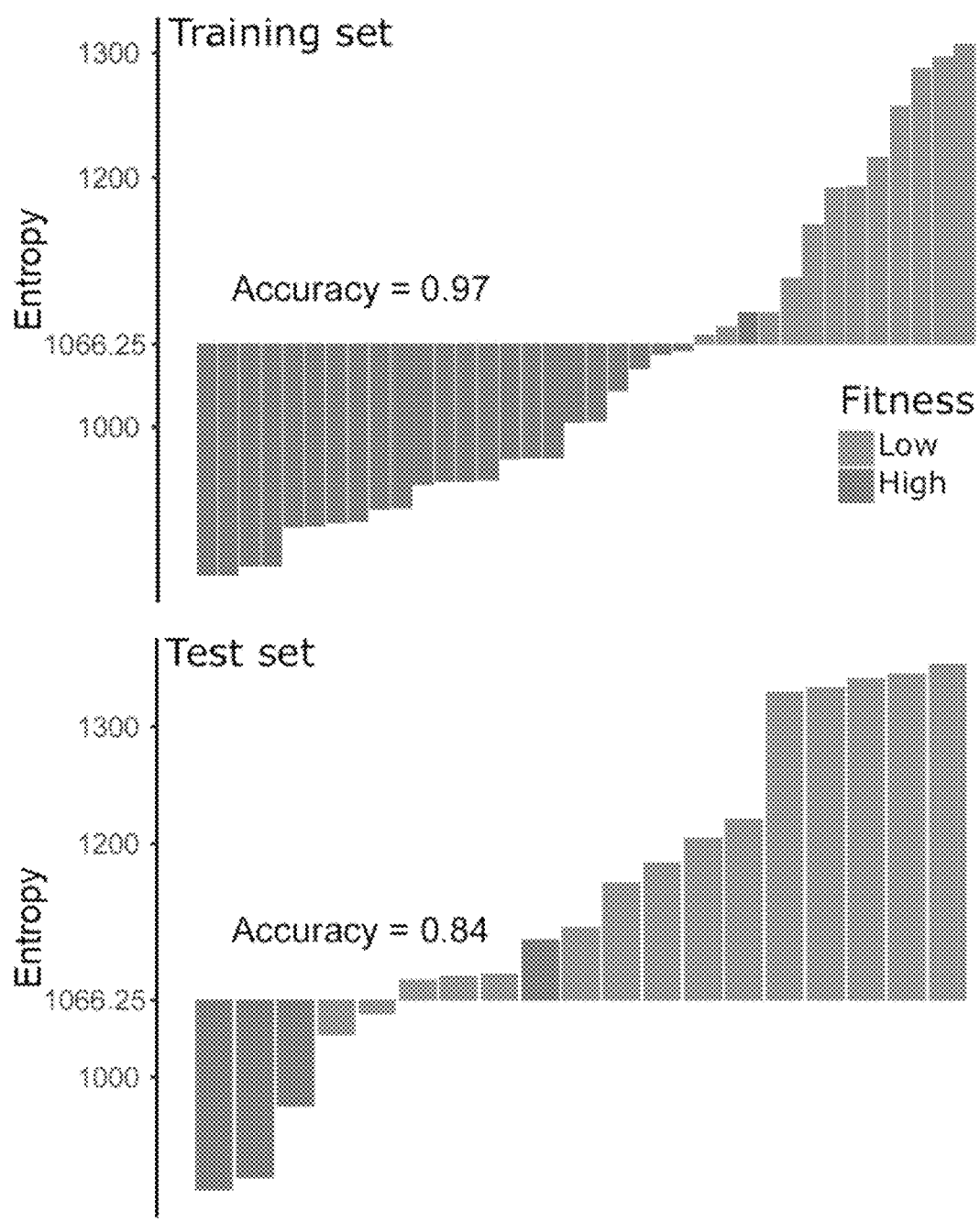
Figure 11A:
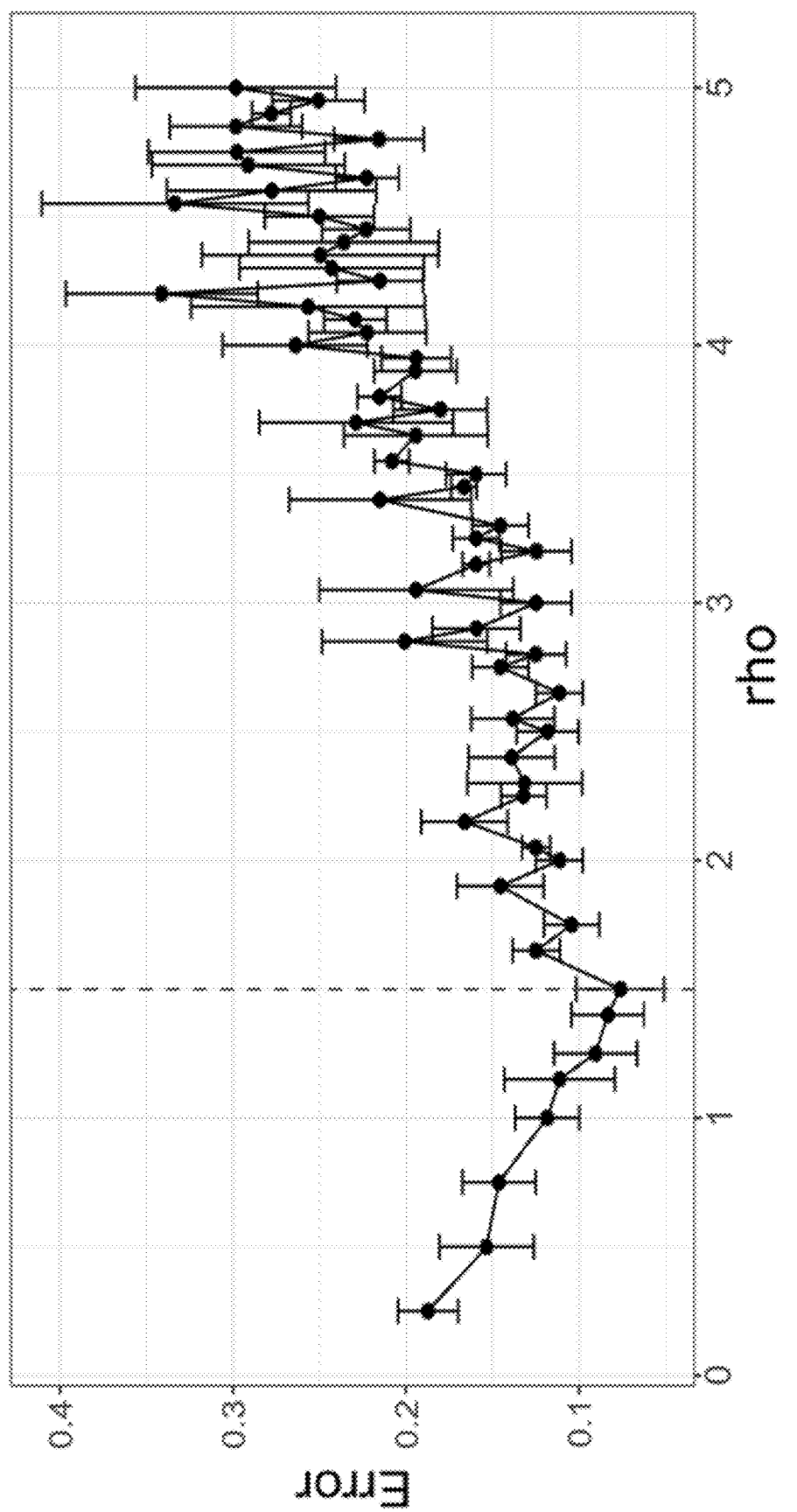
FIGS. 11A-11C. Variants of entropy on time course data also predict fitness with high performance. To test whether entropy was sensitive to regularization parameter rho, two extreme values of rho were used, as opposed to the optimal value of rho=1.5 determined based on crossvalidation error (FIG. 11A). For rho=0 (corresponding to no regularization, and a dense network of gene-to-gene interactions), and for rho=∞ (corresponding to no interactions, and an empty network), the resulting networks for wildtype T4 exposed to VNC are shown (FIG. 11B). These two extreme models were evaluated using ROC and PR curves and resulted in areas under the curve ≥0.85 for all cases in both PR and ROC, for training and test datasets (FIG. 11C). Full list of performance statistics can be found in Table 8.
Figure 11B:
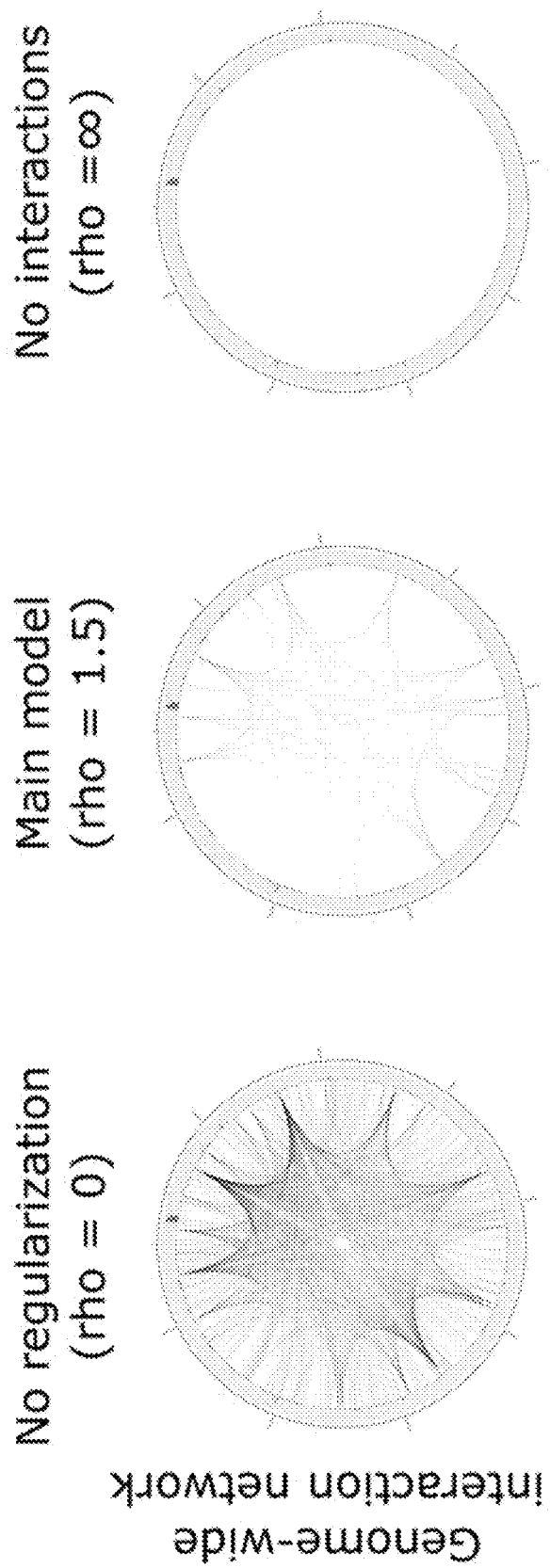
Figure 11C:
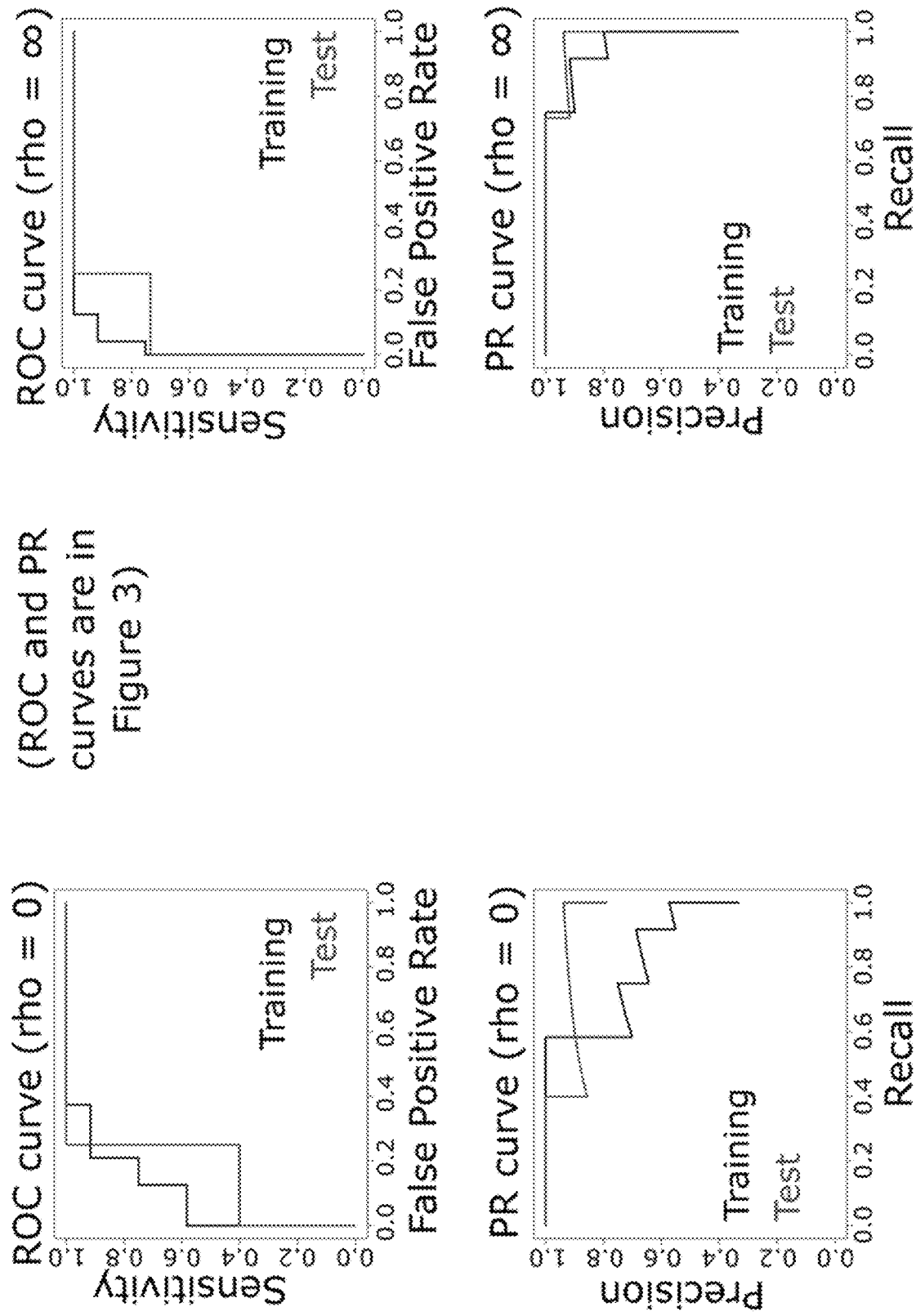

Training of this multi time-point entropy model includes the determination of two parameters: regularization strength $\rho$ and threshold t. This is accomplished by first determining $\rho$ by 5-fold crossvalidation (on the training set), and then determining t for this selected $\rho$. $\rho$ at 1.5 minimizes crossvalidation error (FIG. 3C) and using this value of $\rho$ on the full training set, results in a threshold t of 1066.25. This in turn yields an accuracy of 0.97 and 0.84 in the training and test sets respectively (FIG. 3F, Tables 7 & 8), which are both higher accuracies than the corresponding values obtained with the gene-panels (FIGS. 1A-1G, Table 8). Receiver-operator characteristic (ROC) curve analysis shows that entropy can effectively separate high and low fitness cases, with an area under the ROC curve of 0.99 and 0.91 for the training and test sets respectively (FIG. 3D). Precision-Recall (PR) curve analysis reveals that entropy can detect high-fitness cases, with an area under the PR curve of 0.99 and 0.98 for the training and test sets respectively (FIG. 3E). Both ROC and PR analyses thus show much better performance of entropy compared to the gene-panel on the test set (Table 8). Unlike the gene-panel based fitness prediction models, the entropy model is robust to the selection of regularization strength $\rho$. It is possible to set $\rho$ to be an extreme value and still get comparable performance to the model above (FIGS. 11A-11C). Here, two such extreme values are considered. For instance, if $\rho = \infty$ (i.e. the covariances among genes are ignored and genes' responses are assumed to be independent), entropy can be computed as the average of the logarithm of variances of all genes. In this case, the training and test set accuracies are 0.94 and 0.74 respectively (Table 8), which is comparable to the fitness gene-panel. If, on the other extreme, ρ=0, i.e. entropy is computed directly on the non-regularized covariance matrix, the model will over-correct for a dense network. In this case, the training and test set accuracies are 0.86 and 0.32 respectively (Table 8). In this case, the poor performance on the test set is likely due entropy being sensitive to the number of experimental timepoints used. The training set (which is used for determining t) contains mostly experiments with 7 timepoints or more, whereas the test set contains experiments with only 2 timepoints (Table 1). Using fewer timepoints changes entropy in the same direction for most experiments: for ρ=0 or ρ=∞ entropy in most experiments is increased when more timepoints are used, whereas for ρ=1.5 entropy in most experiments is decreased when more timepoints are used (FIGS. 12A-12C). For ρ=∞ or ρ=1.5 this effect does not negatively impact predictive performance drastically (FIG. 3 & FIGS. 11A-11C). However, for ρ=0 it appears that the value of t determined on the training set is inappropriate for the test set. Yet the low-fitness experiments in the test set still have higher entropy than high-fitness experiments (FIG. 11C). Thus, a lower threshold for entropy could perform better on experiments with fewer timepoints. While the model is sensitive to extreme changes in regularization, this sensitivity is not as severe as the gene-panels, since the extreme value of ρ=∞ also yields a test set accuracy of 0.74, which is comparable to the gene-panel method with a 0.79 test set accuracy. The entropy-based model thus operates with highest accuracy when biologically realistic assumptions are made.

Example 4

Figure 4A:
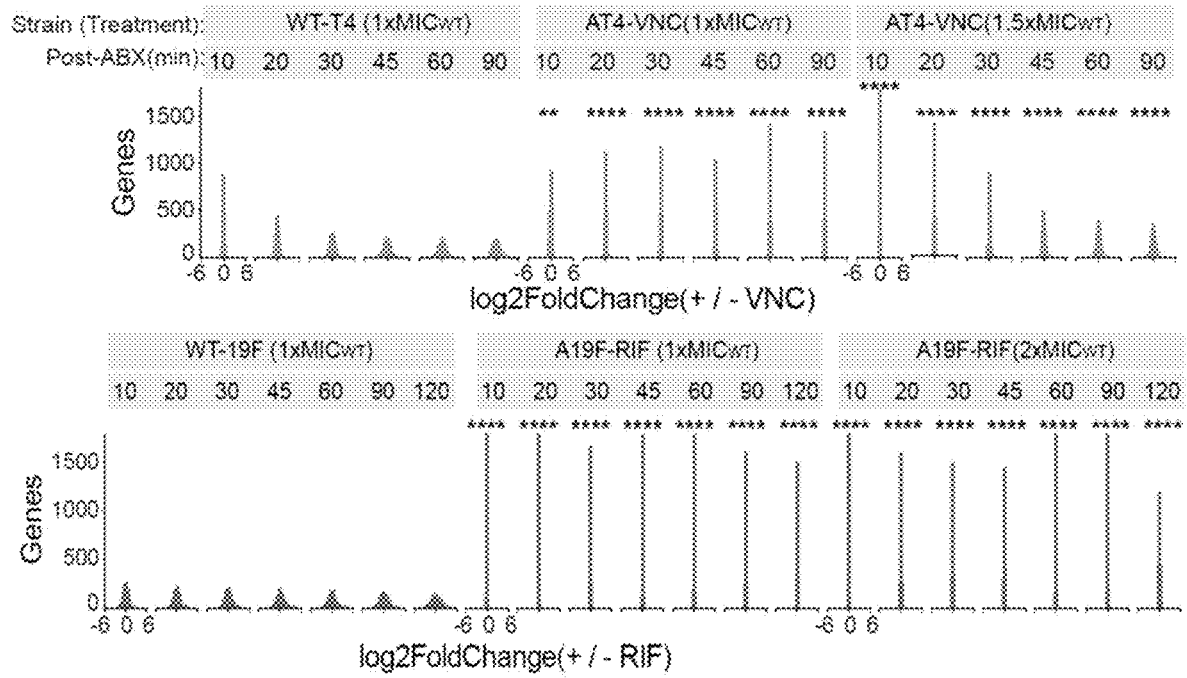
FIGS. 4A-4G. Fitness can be accurately predicted using a simpler, single time-point based definition of entropy.
Figure 4B:
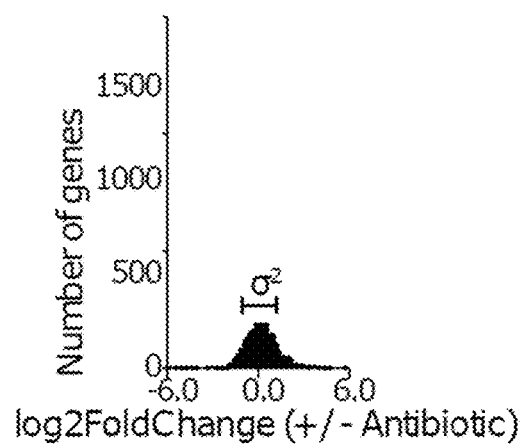
Figure 4C:
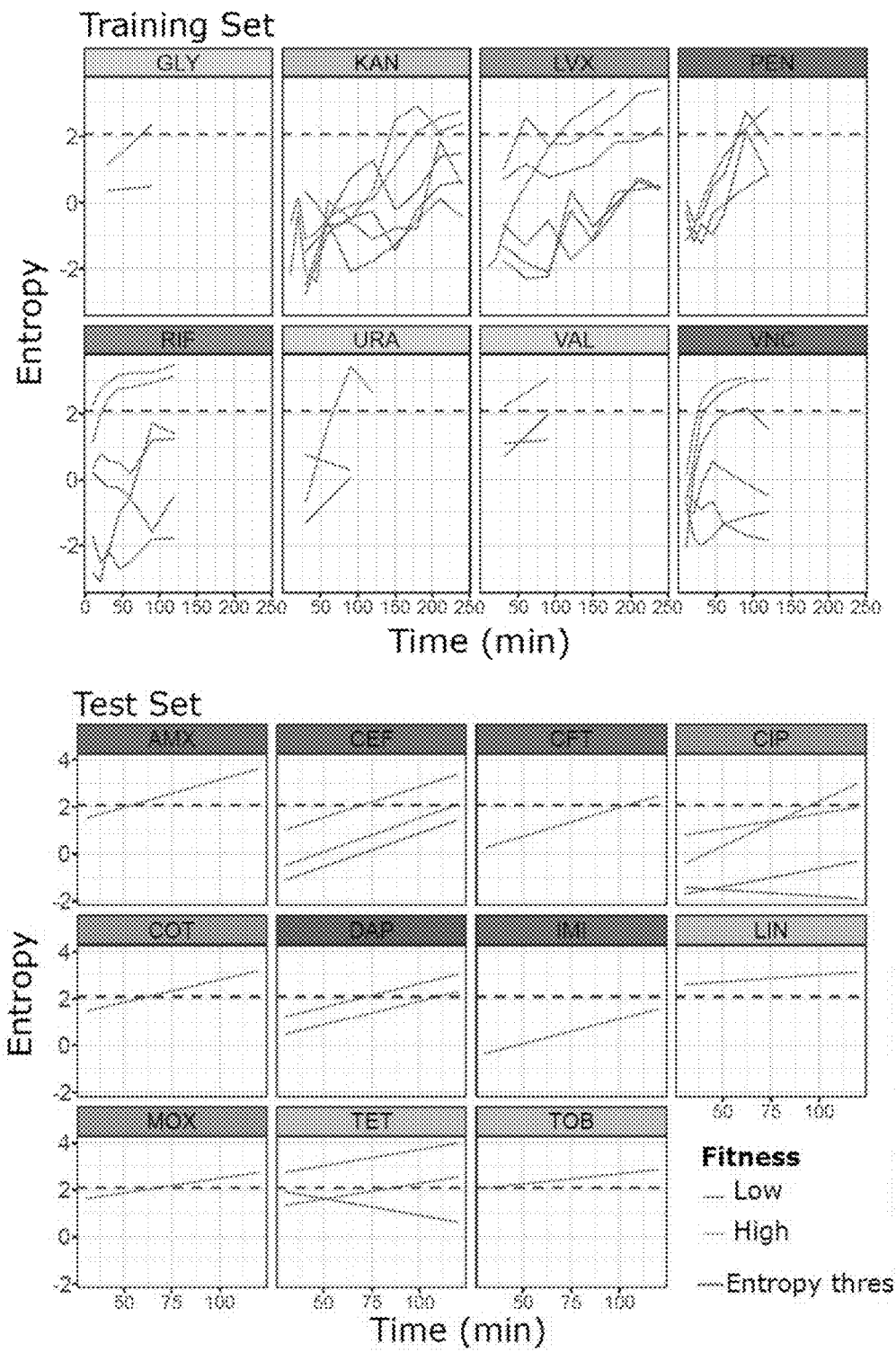
Figure 4D:
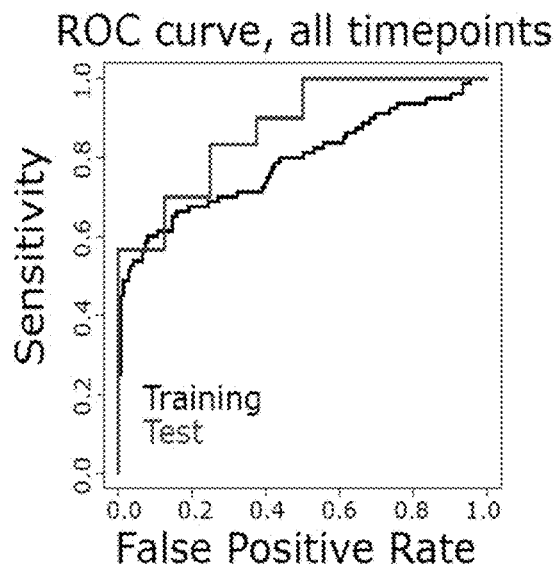
Figure 4E:
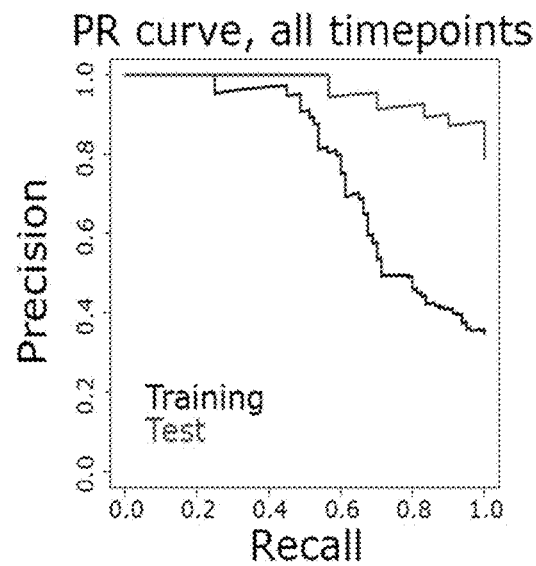
Figure 4F:
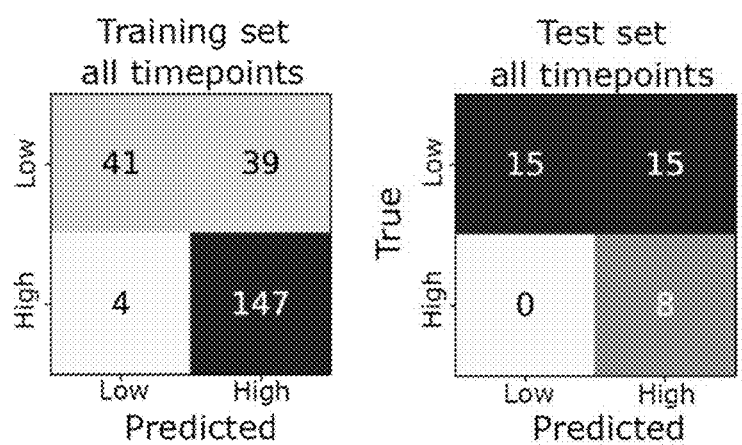
Figure 4G:
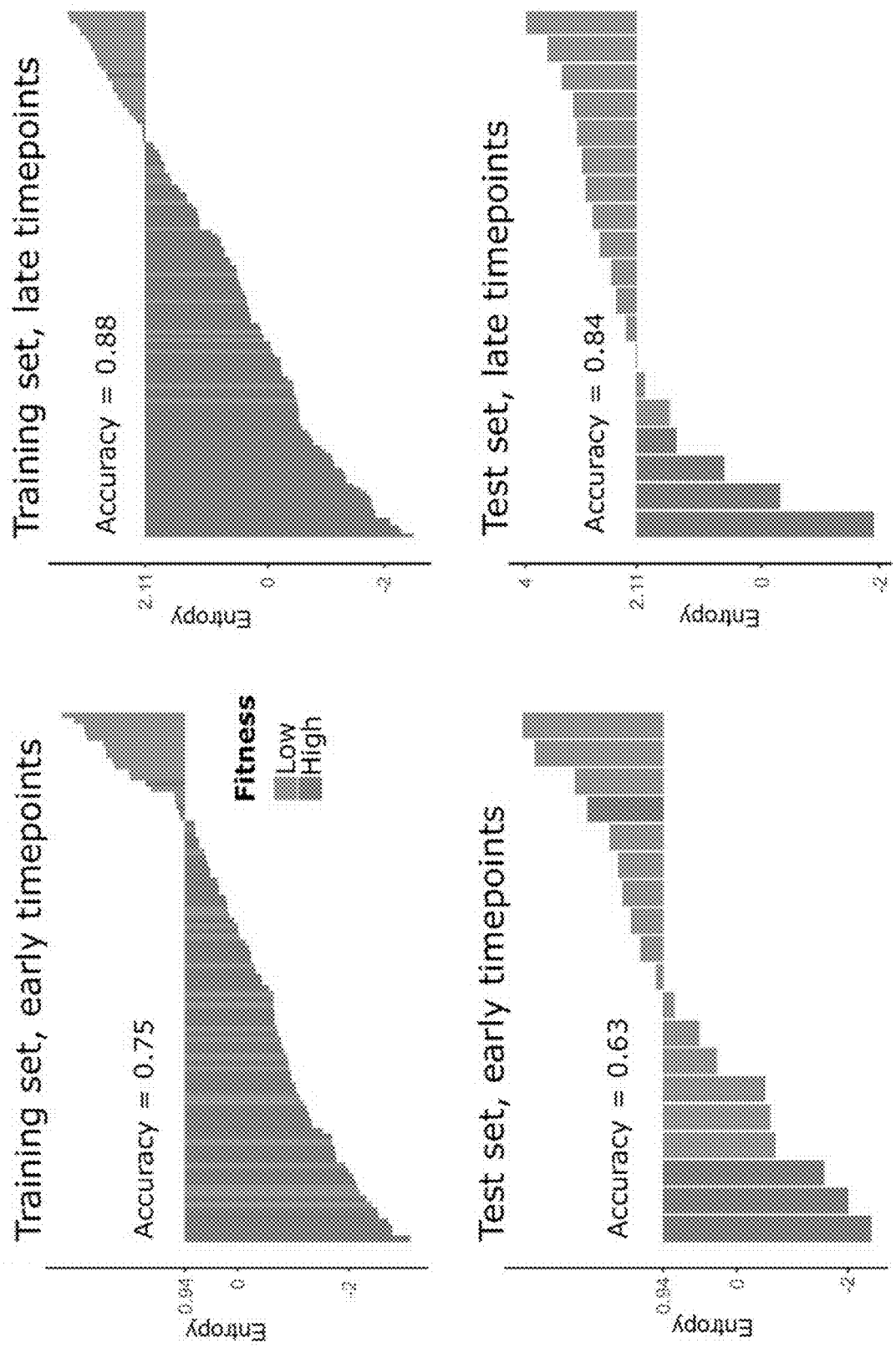

An even simpler model of entropy can predict fitness outcome from a single time-point The time course experiments accurately capture a bacterium's survival in a test environment, but they are labor intensive and potentially expensive. In cases where temporal information may not be available, computing covariance across genes is not possible. However, entropy can still be determined for a single-timepoint transcriptome profile as follows[38]:

$$H_{stp} = ln(\sigma^2) \quad (2)$$

Where $\sigma^2$ is the variance of the distribution of differential expression across genes for a single timepoint (FIGS. 4A & 4B). Similar to the temporal models, a threshold for entropy was determined automatically (in this case 2.08), which is the value that maximizes classification accuracy in the training set which contains data from multiple timepoints. Analogous to the temporal models, low fitness is associated with higher entropy compared to high fitness conditions (FIG. 4C). The single-timepoint variant of entropy outperforms gene-panels: on the test set, the area under ROC curve is 0.88 for entropy, and 0.75 for the gene-panel (FIG. 4D, Table 8). Similarly, for the test set, the area under the PR curve is 0.96 for entropy, whereas for the gene-panel, it is 0.32 (FIG. 4E, Table 8). Moreover, the single timepoint variant of entropy can classify low and high fitness cases with an accuracy of 0.81 and 0.61 in the training and previously unseen test sets respectively (FIG. 4F, Table 8). However, these data show that different antibiotics trigger responses in a time dependent manner, which may lead to ambiguities in the entropy-based prediction of fitness for early timepoints for antibiotics that cause a slower response (e.g. KAN, FIG. 4C). Therefore, predictions based on (slightly) later timepoints might result in improved accuracy. To test this, the training and test datasets were split into early (≤45 minutes of stress exposure) and late (≥60 minutes of exposure) timepoints. Two new thresholds for entropy were determined: $t_{early}$=0.94 on the early timepoints and $t_{late}$=2.11 on the late timepoints within the training data. On the early timepoints, $t_{early}$ achieves an accuracy of 0.75 and 0.63 on the training and test sets respectively. On the later timepoints, $t_{late}$ yields a high accuracy of 0.88 and 0.84 on the training and test datasets, only including 3 false positive predictions in the test data set (FIG. 4G). This shows that entropy computed on data from later time points results in a higher predictive accuracy of fitness outcome than earlier time points (FIG. 4G). Biologically this also makes sense, because while only some antibiotics trigger a clear response within 30-60 minutes after exposure, all antibiotics trigger an increasingly pronounced response as exposure times progress past 60 minutes. The time dependency of an antibiotic response thus makes it more difficult to accurately predict fitness using data from early timepoints. This time dependency would affect the gene-panel for fitness predictions as well. Even though the gene-panel is trained and tested on only the later timepoints and has far poorer performance compared to entropy trained and tested on the same (late) timepoints. Moreover, entropy trained on early timepoints does only slightly worse than gene-panels trained on late timepoints, with only 3 additional misclassifications (Table 8). This highlights that despite the time dependency of an antibiotic response, this new entropy-based approach can make predictions on at least two-time frames, unlike gene-panels.

Overall, the entropy model (and its variants) has several advantages. First, it is based on a simple, and intuitive principle: large and independent changes in the transcriptome are indicative of dysregulation, and beyond a threshold predictive of low fitness. Second, it is possible to simplify the entropy-based model to accommodate less data (i.e. single timepoint transcriptome). Third, an entropy-based model has few parameters (at most 2 parameters need to be determined) and is therefore less likely to be overfit to data. Fourth, the model does not depend on the identity of specific genes, who may or may not be present in different strains/species. Fifth, the model could be easily applied to other data types (e.g. proteomics, metabolomics). Therefore, an entropy-based model is more likely than a gene-panel based approach to be generalizable to previously unseen conditions and species.

Example 5

Figure 5A:
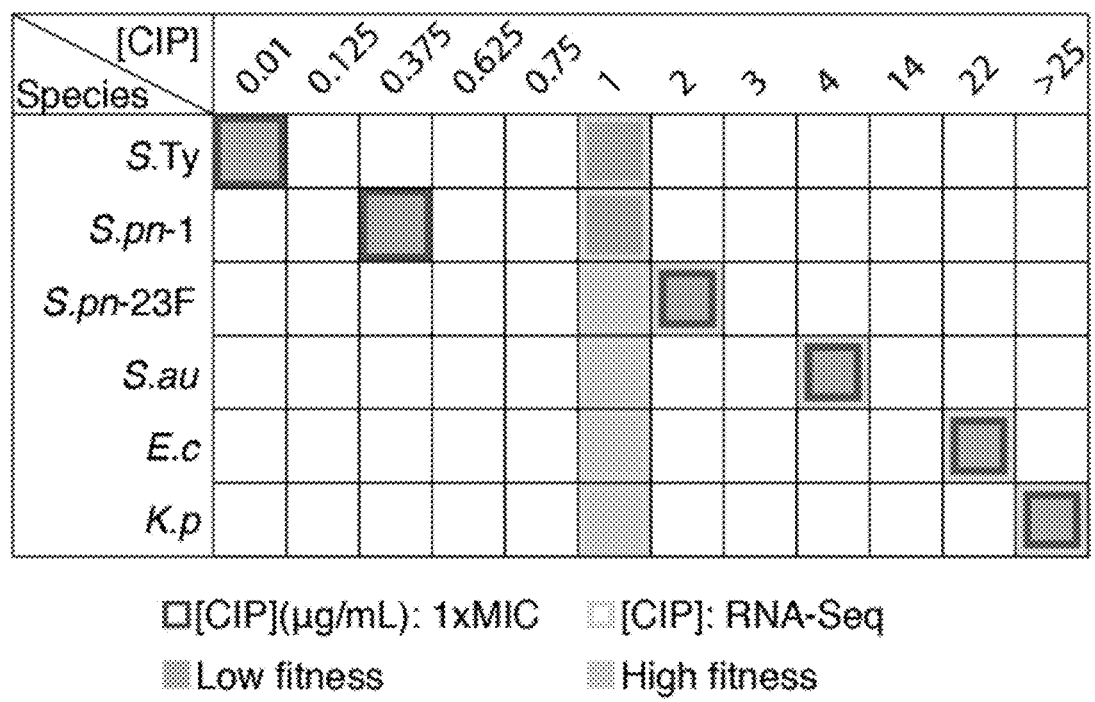
FIGS. 5A-5F. Entropy-based fitness predictions extend to multiple species under antibiotic and non-antibiotic stress.
Figure 5B:
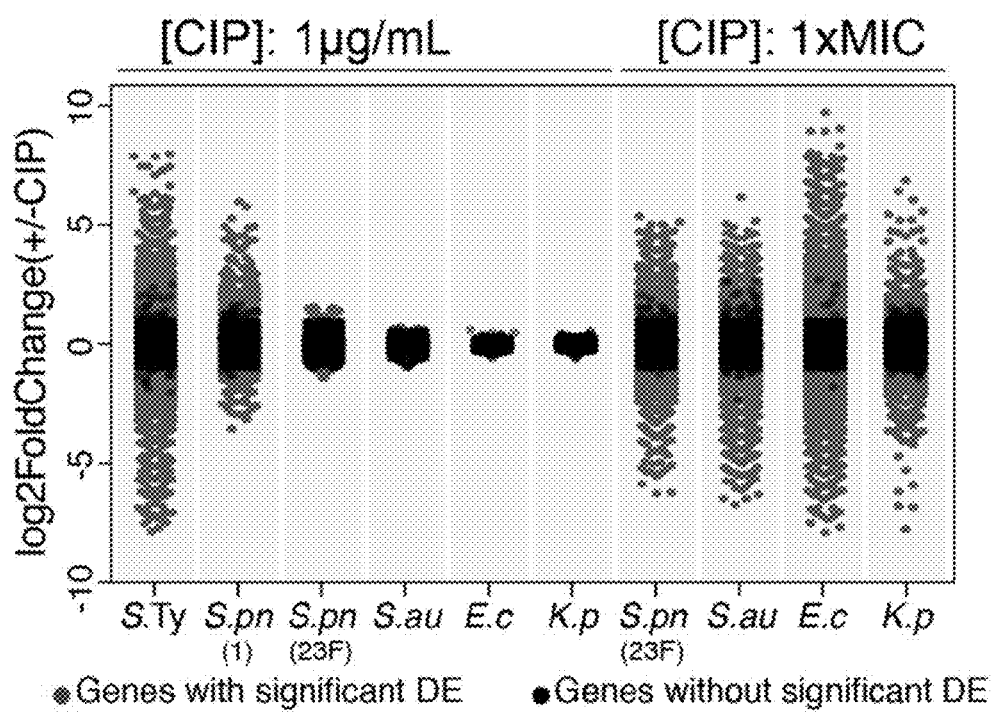

Entropy-based fitness predictions are strain, species and stress-type independent and can be used to infer the antibiotic minimum inhibitory concentration To test if the entropy-based approach is indeed generalizable and successfully predicts fitness for other S. pneumoniae strains and other species, a new RNA-Seq dataset was generated under ciprofloxacin exposure for Salmonella Typhimurium, Staphylococcus aureus, E. coli, Klebsiella pneumoniae and two additional S. pneumoniae strains representing serotypes 1 and 23F (Table 1). These five species represent both Gram-negative and Gram-positive bacteria and cover a wide range of ciprofloxacin MICs (FIG. 5A). Since the single-timepoint variant of entropy is the most practical (in terms of data collection and cost), the generalizability of entropy to previously unseen species was evaluated using this model. RNA-Seq was performed at 120 min post exposure to 1 μg/mL of CIP. The overall response characteristics are similar to what was observed for S. pneumoniae, with 120 minutes exposure to 1 μg/mL ciprofloxacin triggering expression changes with higher variance from bacterial cultures having low fitness (*S. Typhimurium* and *S. pneumoniae* serotype 1), compared to those with high fitness (*S. pneumoniae* serotype 23F, *E. coli* and *K. pneumoniae*) (FIG. 5B). Single-timepoint entropy was computed for the transcriptome of each of these previously unseen isolates. Importantly, with the original threshold of 2.08, which was determined during model training with data from *S. pneumoniae* in FIGS. 4A-4G, fitness outcomes could be predicted for the new organisms with 100% accuracy, indicating that the single-timepoint entropy measure, which uses the least amount of data compared to other variants of entropy, is a species-independent generalizable feature for fitness outcome.

Figure 5C:
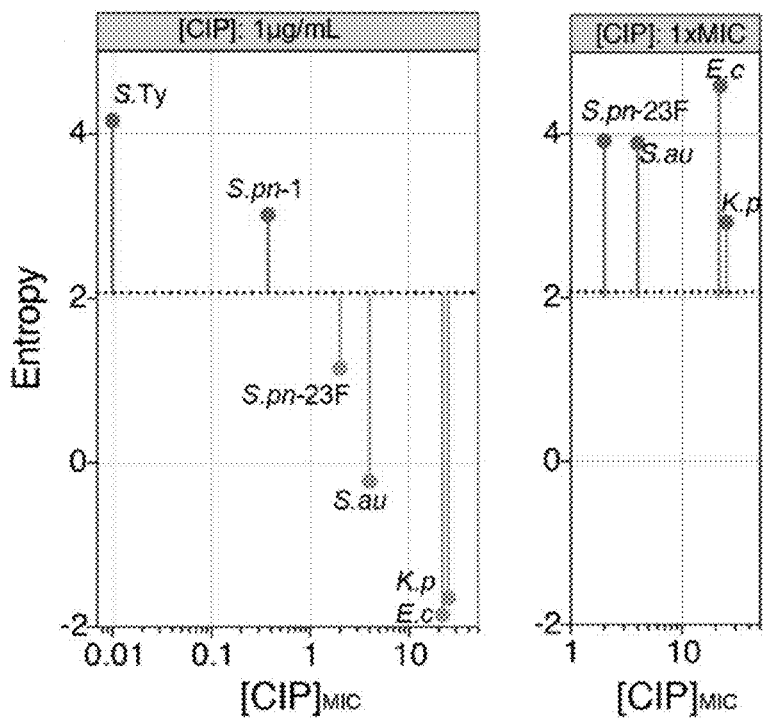
Figure 5D:
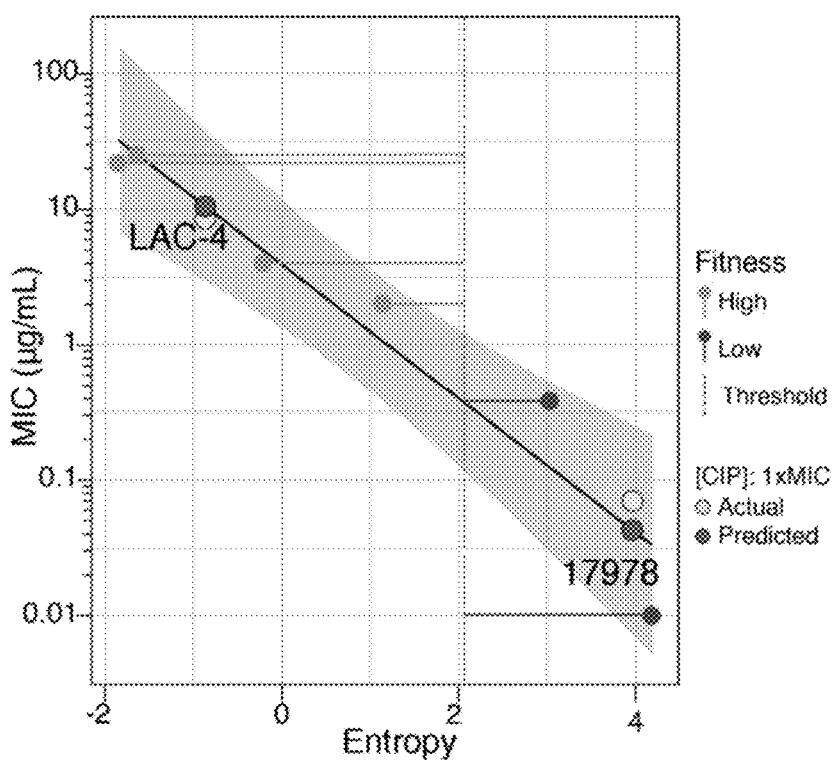
Figure 6A:
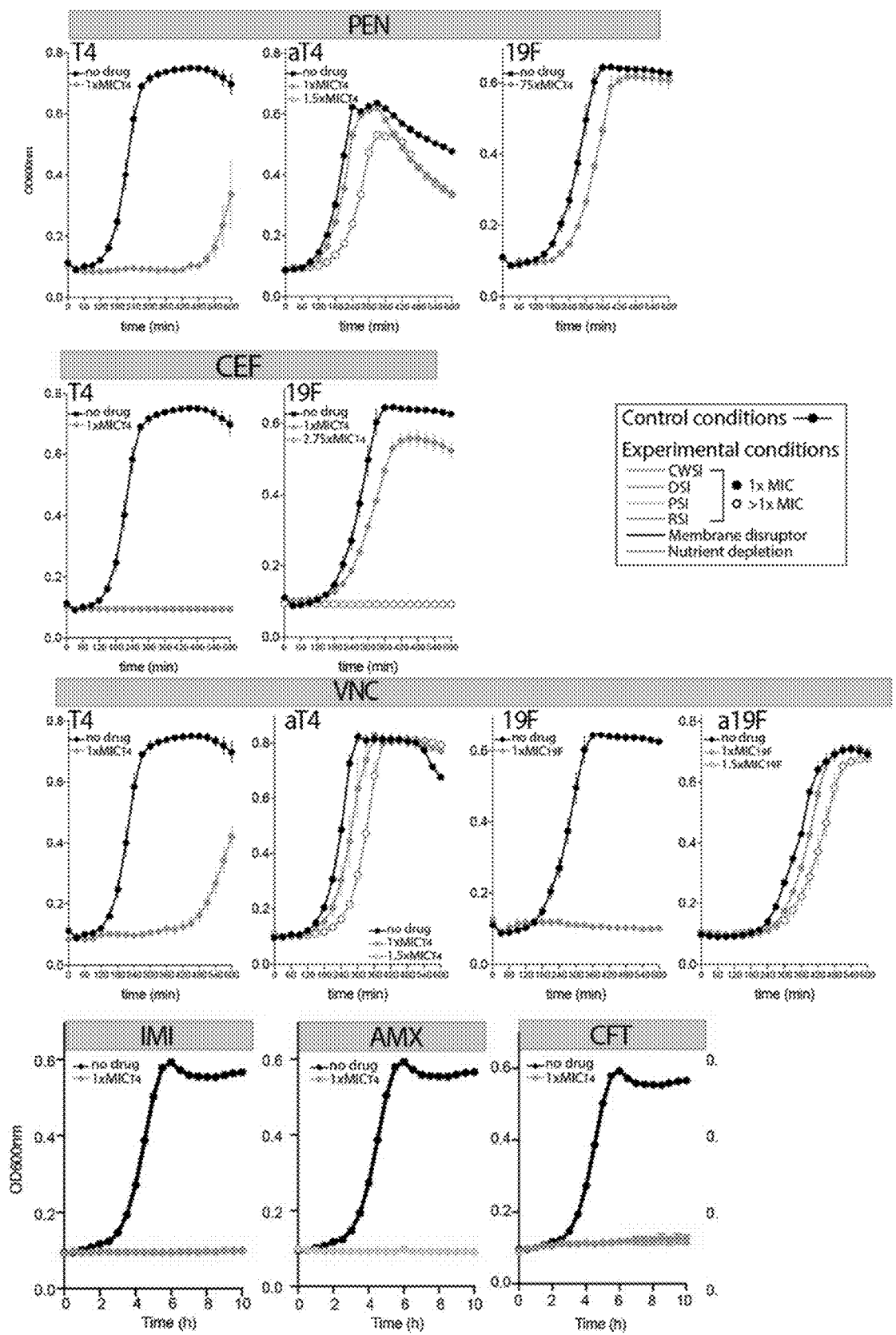
Figure 6B:
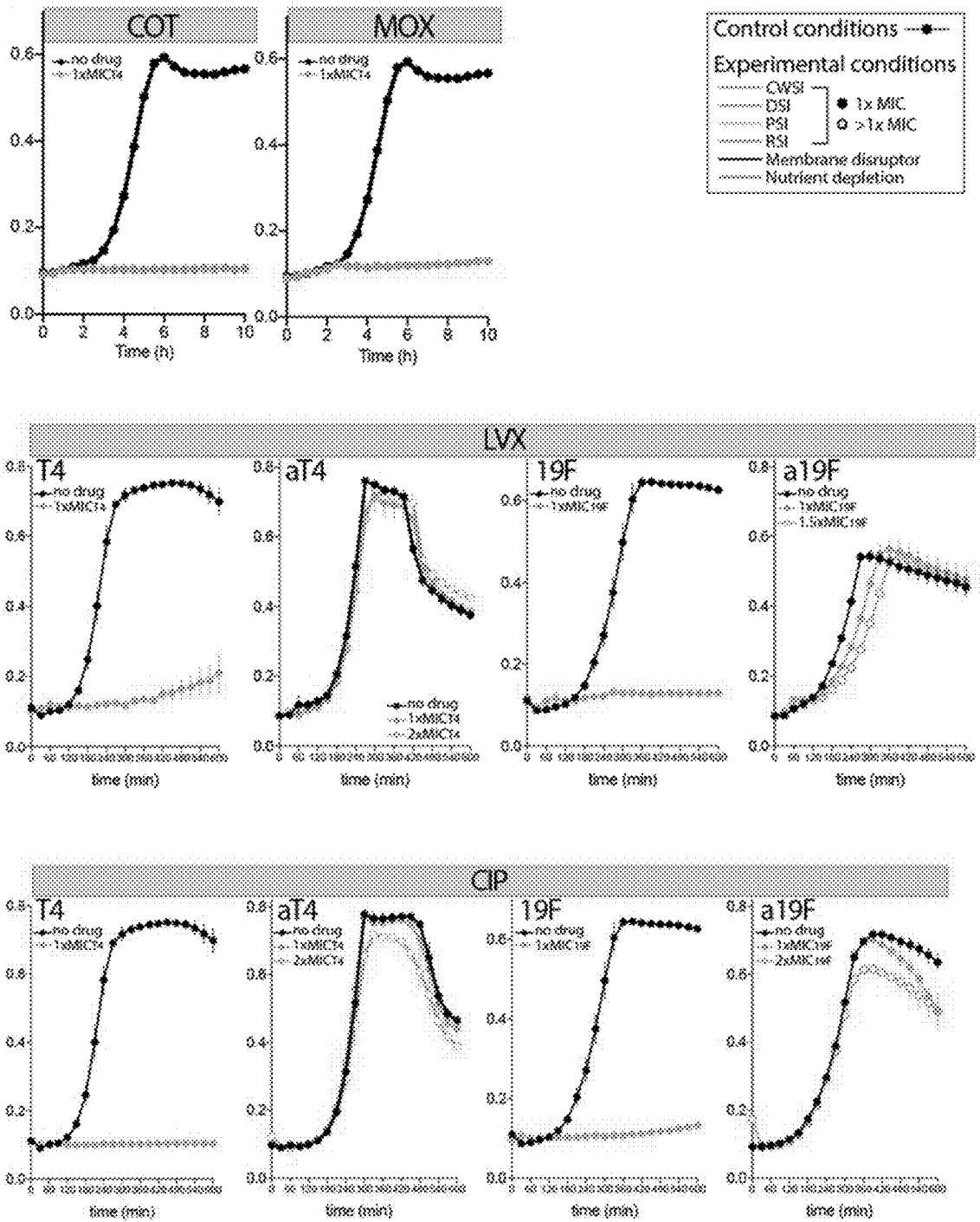
Figure 6C:
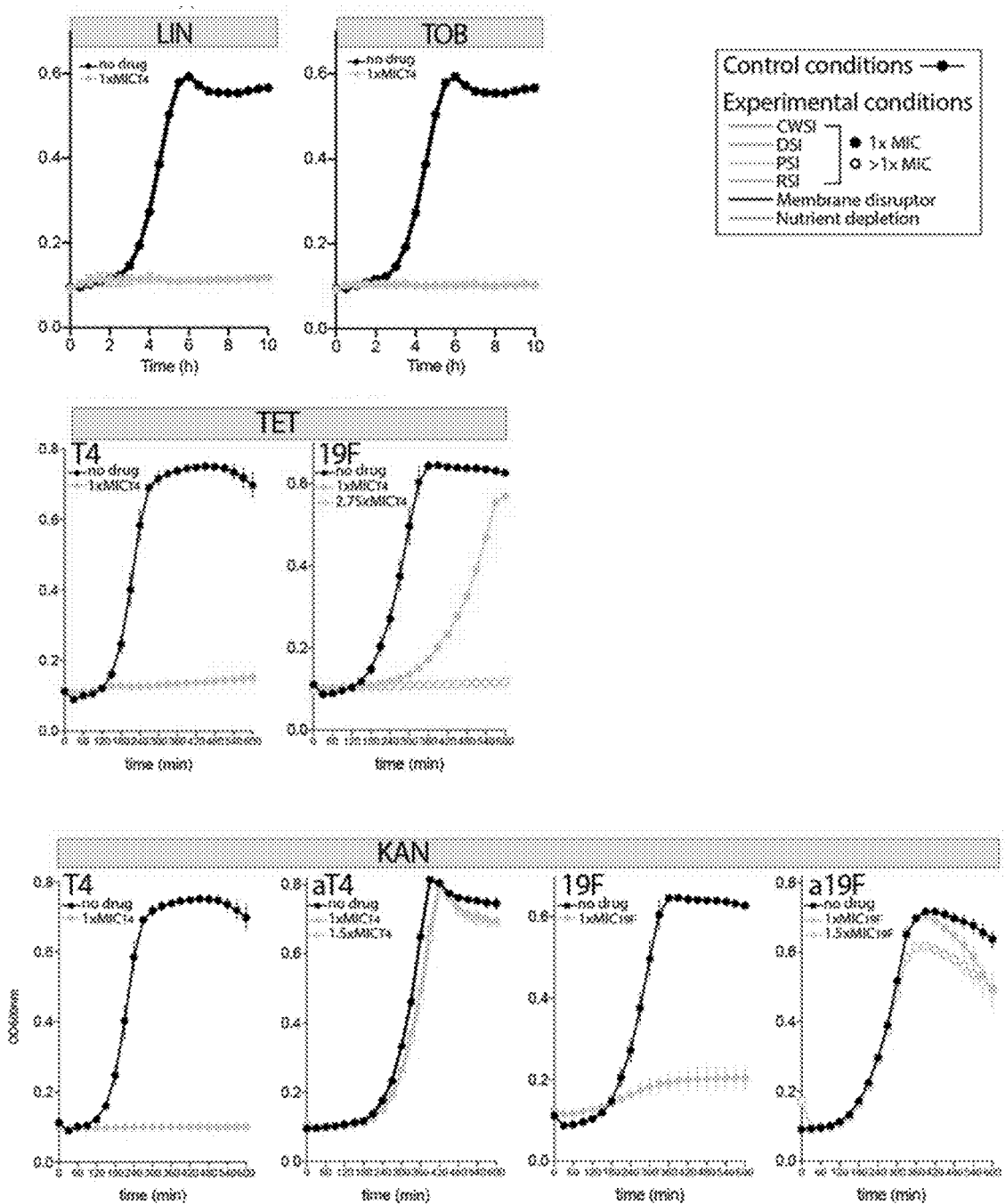
Figure 6D:
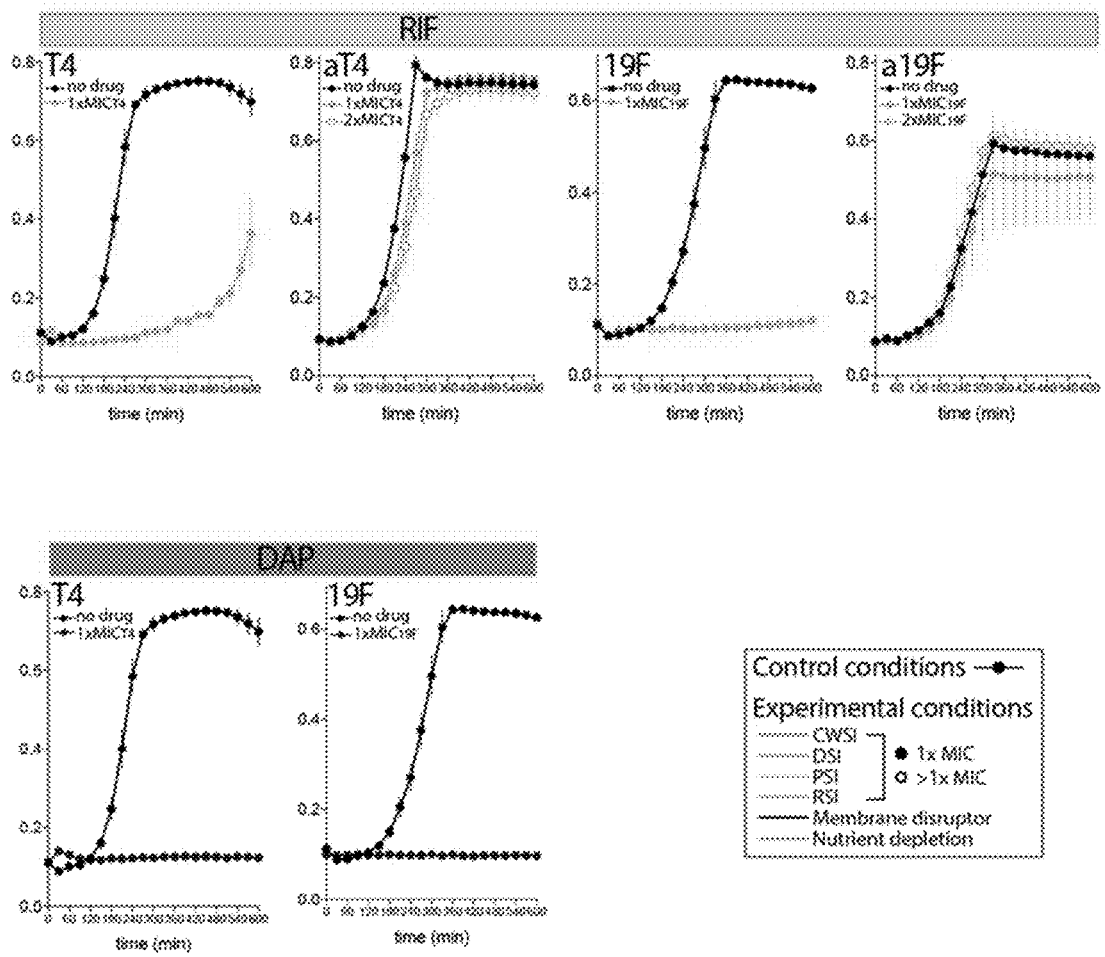
Figure 6E:
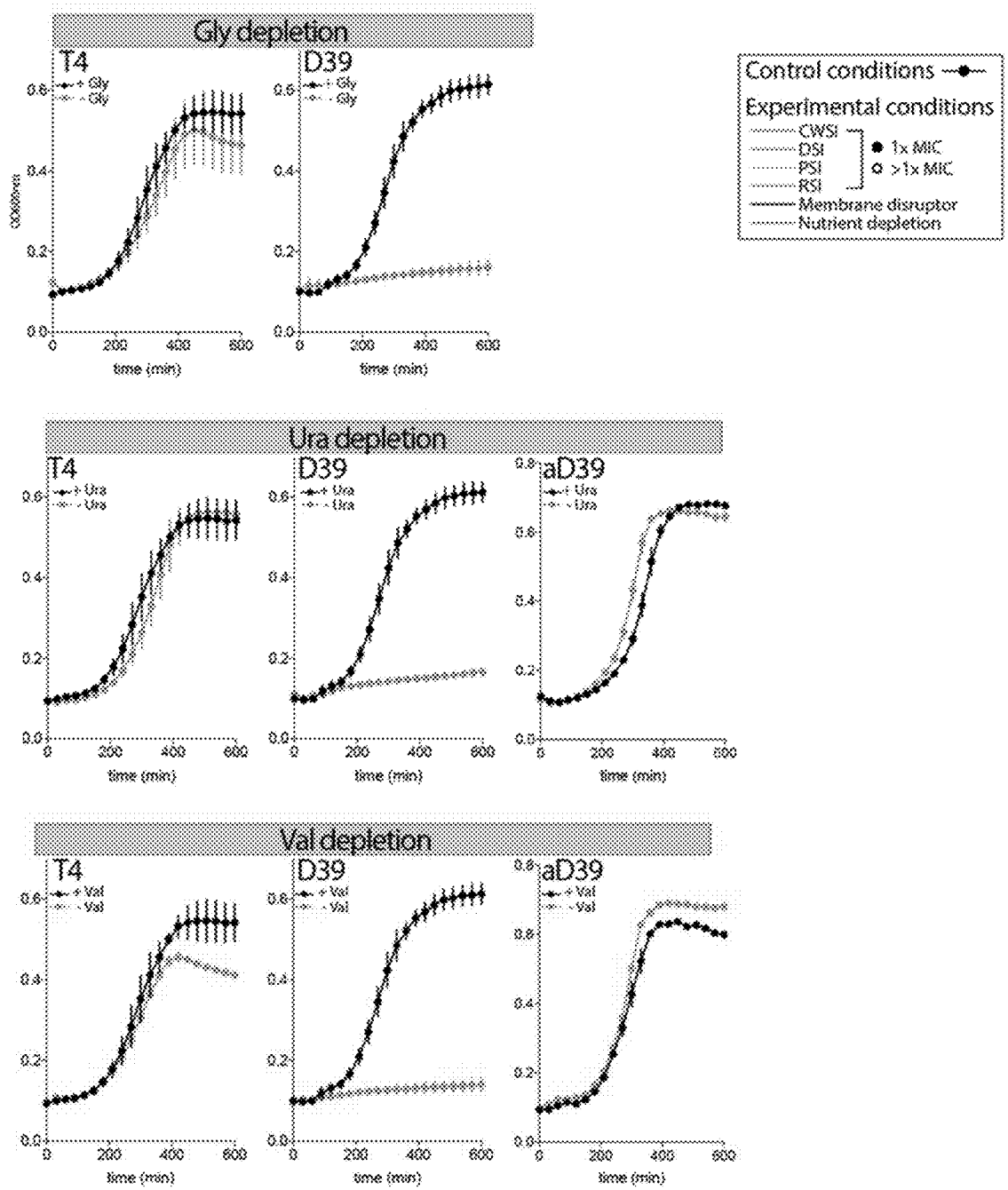
Figure 6F:
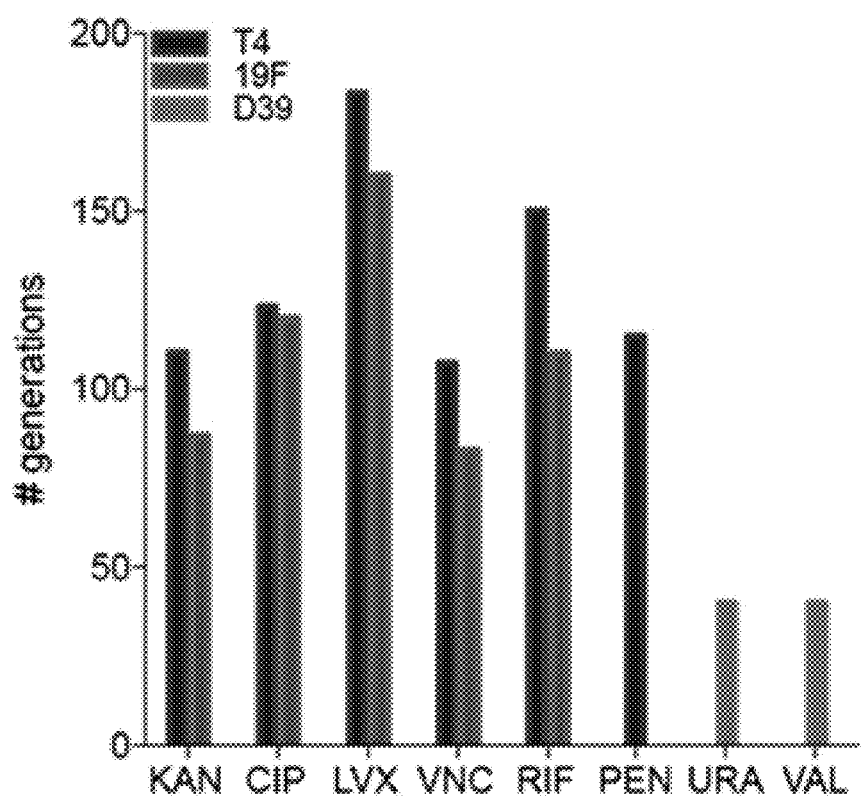

Furthermore, the entropy measurement of each strain was found to be inversely proportional to the $MIC_{CIP}$ (FIG. 5C), consistent with transcriptional disruption being proportional to stress sensitivity. The correlation between entropy and ciprofloxacin sensitivity in FIG. 5C (left panel) therefore implies that the antibiotic sensitivity of other species could be predicted from its transcriptomic entropy. To test this, entropy was calculated for *Acinetobacter baumannii* isolates that are either low (ATCC 17978) or high (LAC-4) virulence, by collecting RNA-Seq profiles after 120 min exposure to 1 μg/mL of ciprofloxacin. Using a linear regression model, the ciprofloxacin MICs of the *A. baumannii* strains were predicted to be 0.04 and 10.45 μg/mL, which are proximate to the measured MIC's of 0.07 and 8.5 μg/mL for ATCC 17978 and LAC-4, respectively (FIGS. 5D & 6D). This demonstrates that entropy is not simply a binary indicator of fitness outcomes but can even be applied to determine antibiotic sensitivity level for new unseen species that were not in any training data.

Figure 5E:
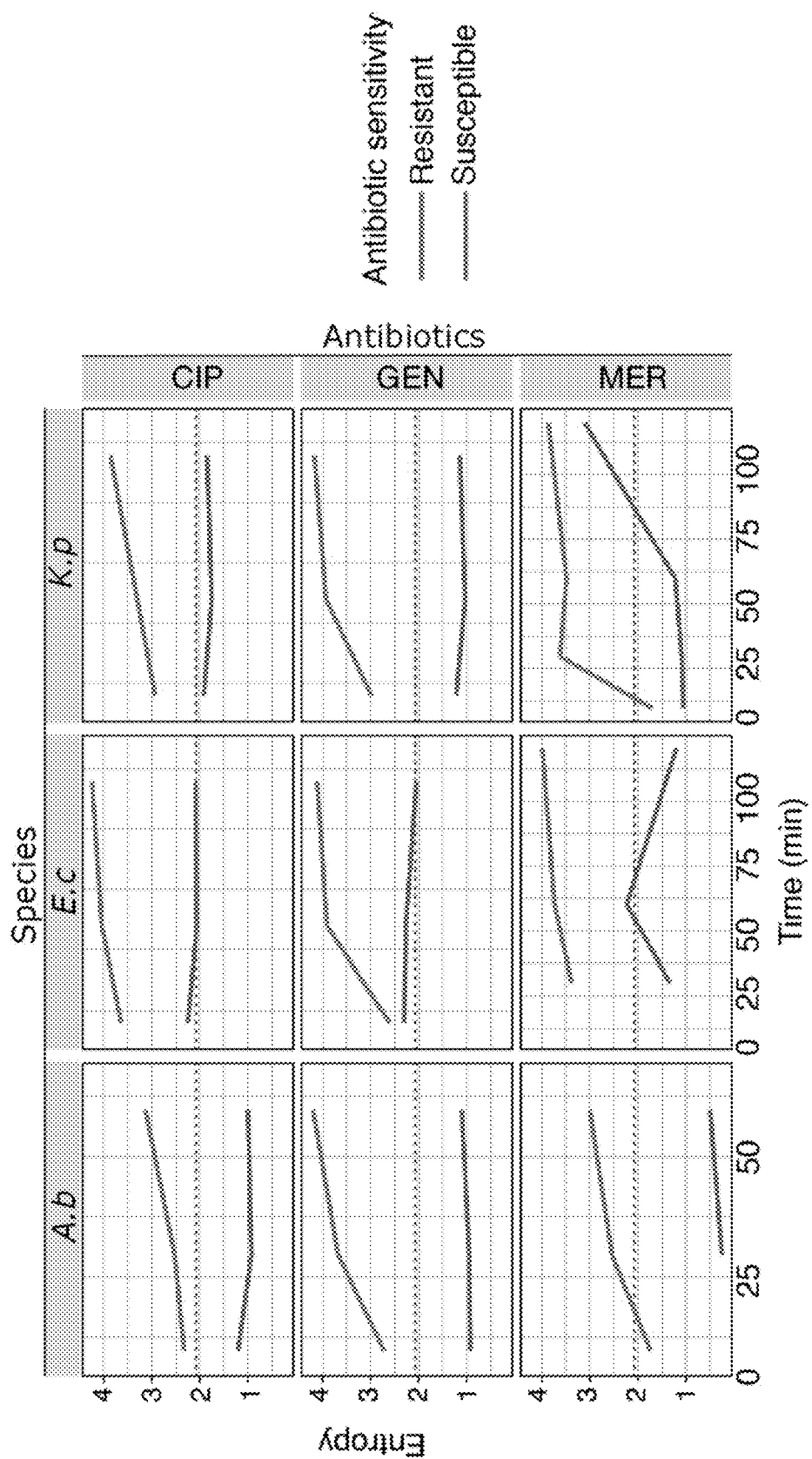

To further validate the approach, data from Bhattacharyya et al[11] was used. In this RNA-Seq dataset, susceptible and resistant strains from 3 species were exposed to 3 different antibiotics (2 of which were not present in our dataset). Again, by using the entropy threshold of 2.08 (obtained above through training on the *S. pneumoniae* data) susceptible strains with low fitness are successfully separated from resistant strains with high fitness (FIG. 5E).

Figure 5F:
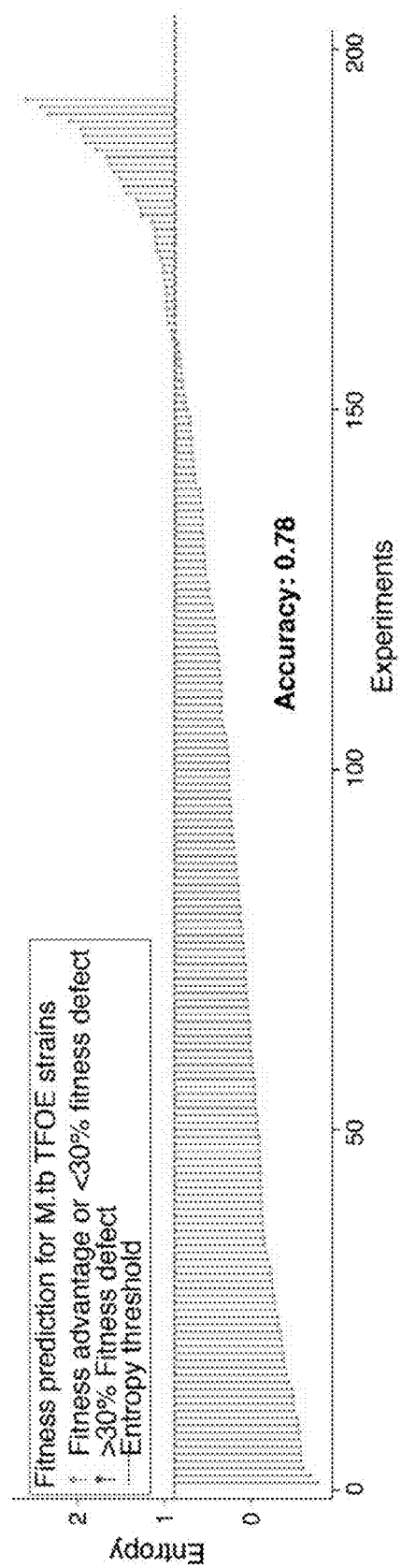

To explore the applicability of entropy beyond nutrient and antibiotic stress, entropy-based fitness classification was performed on a published collection of 193 *M. tuberculosis* transcription factor over-expression (TFOE) strains[39]. Upon TFOE, these strains exhibit fitness changes, ranging from severe growth defects to small growth advantages[40]. Overexpression of a single transcription factor can thereby exert stress on the bacterium that can result in different fitness outcomes. By calculating entropy from whole-genome microarray data collected from each TFOE strain, it is possible to distinguish strains based on their fitness levels at an accuracy of 0.78, using a newly trained entropy threshold for this dataset (FIG. 5F). This result compares favorably with a much more complicated approach involving the integration of each TFOE transcriptional profile into condition-specific metabolic models[39]. Overall, these data clearly highlight the strength of entropy, which has the potential to be utilized as a generalizable fitness prediction method for both antibiotic and non-antibiotic stress, and a large variety of bacterial strains and species.

Example 6

Methods

Bacterial strains, culture media and growth curve assays

*S. pneumoniae* strain TIGR4 (T4; NC_003028.3) is a serotype 4 strain originally isolated from a Norwegian patient[3,4], Taiwan-19F (19F; NC_012469.1) is a multi-drug resistant strain[5,6] and D39 (NC_008533) is a commonly used serotype 2 strain originally isolated from a patient about 90 years ago[7]. Strain PG1 and PG19 were isolated from adults with pneumococcal bacteremia infection and included in the Pneumococcal Bacteremia Collection Nijmegen (PBCN)[8]. All *S. pneumoniae* gene numbers refer to the T4 genome. Correspondence between homologous genes among *S. pneumoniae* strains and gene function annotations are described herewith. *Escherichia coli* strain AR538, *Klebsiella pneumoniae* strain AR497 and *Salmonella enterica subsp* Typhimurium strain AR635 were clinical isolates obtained from the Center of Disease Control (CDC). *Staphylococcus aureus* strain MN6 was kindly provided by George Sakoulas (Center of Immunity, Infection & Inflammation, UCSD School of Medicine). Unless otherwise specified, *S. pneumoniae* strains were cultivated in Todd Hewitt medium with 5% yeast extract (THY) with 5 μL/mL oxyrase (Oxyrase, Inc) or on sheep's blood agar plates (Northeastern Laboratories) at 37° C. with 5% CO2. *A. baumannii, E. coll. K. pneumoniae, S. aureus* and *S. Typhimurium* were cultured in Mueller Hinton broth II (Sigma) at 37° C. with 220 rpm constant shaking. Tn-Seq and RNA-Seq experiments of *S. pneumoniae* under nutrient-depletion and antibiotic conditions were performed in chemically defined medium (CDM)[9] and semi-defined minimal medium (SDMM)[10], respectively. RNA-Seq experiments for *A. baumannii, S. Typhimurium, E. coll. K. pneumoniae,* and *S. aureus* were performed in Mueller Hinton broth II. Single strain growth assays were performed at least three times using 96-well plates by taking $OD_{600}$ measurements on a Tecan Infinite 200 PRO plate reader.

Temporal RNA-Seq Sample Collection, Preparation and Analysis

In nutrient RNA-Seq experiments, T4, D39 and adapted D39 were collected at 30 and 90 min after depletion of D39-essential nutrients. In the training set antibiotic RNA-Seq experiments, wild-type and adapted T4 or 19F were collected at 10, 20, 30, 45, 60, 90, 120 min post-vancomycin, rifampicin or penicillin treatment. Additional time points at 150, 180, 210 and 240 min were collected in levofloxacin and kanamycin experiments due to the slower transcriptional response. In the test set antibiotic RNA-Seq experiments, wild-type T4 and 19F were collected at 30 and 120 min post-cefepime, ciprofloxacin, daptomycin or tetracycline treatment. Ciprofloxacin-adapted T4 and 19F were collected at 30 and 120 min post-ciprofloxacin treatment. T4 was collected at 30 and 120 min post-amoxicillin, ceftriaxone, imipenem, linezolid, moxifloxacin or tobramycin treatment. Wild-type strains were exposed to 1xMIC antibiotics; antibiotic-adapted strains were exposed to 1xMIC and 1.5-2xMIC of the respective antibiotic. Cell pellets were collected by centrifugation at 4000 rpm at 4° C. and snap frozen and stored at −80° C. until RNA isolation with the RNeasy Mini Kit (Qiagen). 400 ng of total RNA from each sample was used for generating cDNA libraries following the RNA-tag-Seq protocol[11] as previously described[9]. PCR amplified cDNA libraries were sequenced on an Illumina NextSeq500 generating a high sequencing depth of ~7.5 million reads per sample[12]. RNA-Seq data was analyzed using an in-house developed analysis pipeline. In brief, raw reads are demultiplexed by 5' and 3' indices[11], trimmed to 59 base pairs, and quality filtered (96% sequence quality>Q14). Filtered reads are mapped to the corresponding reference genomes using bowtie2 with the—very-sensitive option (-D 20 -R 3 -N 0 -L 20 -i S, 1, 0.50)[13]. Mapped reads are aggregated by feature-Count and differential expression is calculated with DESeq2[14,15]. In each pair-wise differential expression comparison, significant differential expression is filtered based on two criteria: |log2foldchange|>1 and adjusted p-value (padj) <0.05. All differential expression comparisons are made between the presence and absence of the antibiotic or nutrient at the same time point.

Experimental Evolution

D39 was used as the parental strain in nutrient-depletion evolution experiments; T4 and 19F were used as parental strains in antibiotic evolution experiments. Four replicate populations were grown in fresh CDM with a decreasing concentration of uracil or L-Val for nutrient adaptation populations, or an increasing concentration of ciprofloxacin, cefepime, levofloxacin, kanamycin, penicillin, rifampicin, or vancomycin for antibiotic adaptation populations. Four replicate populations were serial passaged in CDM or SDMM as controls to identify background adaptations in nutrient or antibiotic adaptation experiments, respectively. When populations were adapted to their nutrient or antibiotic environment, a single colony was picked from each experiment and checked for its adaptive phenotype by growth curve experiments.

Determination of Relative Minimal Inhibitory Concentration (MIC)

1 to 5×10$^5$ CFU of mid-exponential bacteria in 100 uL was diluted with 100 uL of fresh medium with a single antibiotic to achieve a final concentration gradient of cefepime (T4: 0.008-0.8 µg/mL; 19F: 0.6-2.4 µg/mL), ciprofloxacin (S. pneumoniae strains: 0.125-4.0 µg/mL; other species: 0.0125-25 µg/mL), daptomycin (15-55 µg/mL), levofloxacin (0.1-2 µg/mL), kanamycin (35-250 µg/mL), penicillin (T4: 0.02-0.055 µg/mL, 19F: 1-4 µg/mL), rifampicin (0.005-0.04 p82 g/mL), tetracycline (T4: 4-18 µg/mL, 19F: 19-22 µg/mL), amoxicillin (0.01-0.16 µg/mL), imipenem (0.0005-0.045 µg/mL), ceftriaxone (0.0005-0.009 µg/mL), linezolid (0.05-0.65 µg/mL), tobramycin (35-255 µg/mL), cotrimoxazole (0.5-7.5 µg/mL); moxifloxacin (0.05-0.70 µg/mL), and vancomycin (0.1-0.5 µg/mL) in 96-well plates. Each concentration was tested in triplicate. Growth was monitored on a Tecan Infinite 200 PRO plate reader at 37° C. for 16 hours. MIC is determined as the lowest concentration that abolishes bacterial growth (FIGS. 6A-6H).

Selection of Gene Panel For Fitness Prediction

Differential expression data from experiments from all experimental timepoints with time≥60 min were assembled in R (v3.4.3). The data were split into training and test sets as described in Supplementary Table 1, yielding a training set of 138 and a test set of 19 experiments. Genes with incomplete data (e.g. genes unique to one strain) were omitted. The differential expression data was then scaled such that the values for each gene had mean=0 and variance=1. A binomial logistic regression model was fit to the training set with glmnet v3.0-2. In order to determine the appropriate value of the regularization parameter lambda, 5-fold crossvalidation was performed on the training set and mean squared error (MSE) of the crossvalidation set for each of the 5 folds was computed as a measure of classification error. The value of lambda was selected to be the largest at which the MSE is within 1 standard deviation of the minimal MSE overall[16,17].

Evaluation of the gene panel's sensitivity to input data was done using another 5-fold crossvalidation strategy, where for each fold, the training portion includes 80% of the original training dataset. The model was fit with the same strategy as above, selecting the best lambda for each fold.

Evaluation of the gene panel's sensitivity to lambda was done using the standard output of the glmnet function.

For gene panels specific to a single MOA, the training and test sets were filtered to include only experiments from that MOA. Otherwise, all analyses were done as described above.

PCA and Trajectory Clustering

For principal component analysis (PCA), differential expression (log2fold change of +/− antibiotic comparisons) data from all 255 experimental conditions (per time point per antibiotic from all experiments excluding CIP-validation set with A. baumannii, E. coli, K. pneumoniae, S. Typhimurium, S. aureus, S. pneumoniae serotype 1 and 23F strains) were assembled in R (v3.4.3). The function "prcomp" was used for PCA. Timepoints of the same experiment were connected to form trajectories. Since not all experiments are on the exact same time scale (e.g. KAN experiments extend to 240 min whereas RIF experiments cover 120 min), equivalent timepoints for each experiment were determined to be $$\frac{i \times t_{max}}{6} \text{ for } i = 1, 2, \ldots, 6$$

and $t_{max}$ being the latest time point available for the corresponding experiment. If a timepoint did not correspond to an existing RNA-Seq data point, this time point was inferred by linear interpolation of the existing trajectories. To cluster these trajectories, a trajectory-distance metric between two trajectories X and Y is defined as the sum of Euclidean distances ('dist', on the principal component coordinates)

$$\sum_{i=1}^{6} dist(X_i, Y_i)$$

of all timepoints i. All pairwise distances are computed for all pairs of trajectories included in the analysis (WT strains with low fitness, for PSI, DSI, CWSI and RSI). Kmeans clustering in MATLAB with k=4 is used on the pairwise distances to cluster the trajectories.

Selection of Gene Panel for MOA Prediction

Differential expression (log2 fold change of drug/no drug comparison) data from all antibiotic experiments with low fitness outcome and time≥60 minutes were assembled in R (v3.4.3). The data were split into training and test sets as described in Supplemental Table 1, yielding a training set of 39 and a test set of 15 experiments. Similar to the fitness gene panel data preparation, genes with incomplete data were omitted. A multinomial logistic regression model was fit to the training set with glmnet v3.0-2. The appropriate value of lambda was selected using a similar crossvalidation scheme to the fitness gene panel: the largest lambda at which the crossvalidation error is within 1 standard deviation of the minimal error overall.

Evaluation of the model's sensitivity to input and lambda were done as described in the "Selection of gene panel for fitness prediction" section above

Gene Set Enrichment Analysis

Gene panels for *S. pneumoniae* were evaluated for enrichment of functional categories (the category annotation can be found in Supplemental File 1), using a hypergeometric test, and Benjamini-Hochberg correction for multiple comparisons. For gene panels in Bhattacharyya et al.[18], enrichment for GO terms was evaluated using the same procedure. The GO term annotation was acquired from Uniprot.

Quantifying Entropy of Single Timepoint and Temporal Transcriptional Data

Entropy of a single-time point experiment ($H_{stp}$) is calculated using the definition of entropy on normal distributions (equation 1)

$$H_{stp} = \frac{1}{2}\ln(2\pi e \sigma^2) \quad (1)$$

Where $\sigma^2$ is the variance of the differential expression distribution. Note that this is equivalent to Equation (2) in the main text, with some added constants. A threshold was selected by scanning a range of possible thresholds and selecting one that maximizes accuracy on the training set (same as gene panel training set). Performance is reported on this training set and test set (same as gene panel test set).

While this metric is informative, it does not take into account the temporal changes that occur in genes. For the temporal entropy models, all experiments have at least 2 timepoints at which RNA-Seq was performed. For each experiment, all available timepoints were used for temporal entropy analysis. The variance of differential expression is quantified using equation 2

$$H_{temporal1} = \sum_i \ln(2\pi\sigma_i^2) \quad (2)$$

Where $\sigma_i^2$ is the variance in differential expression of $gene_i$ over t time points. Thresholding is done similarly to $H_{stp}$.

An assumption in the previous model is that genes' variation over time are independent of one another. Genes in the same regulon are known to be co-expressed and are examples of highly covarying genes. This means there are potential correlations between pairs of genes. In order to account for this phenomenon, the expression changes in N genes over t timepoints are considered to come from a multivariate normal distribution, with N dimensions. This is in contrast to equation 2, where N independent univariate normal distributions are considered. The entropy of a multivariate normal distribution is defined as (equation 3)

$$H_{temporal2} = \ln(|\Sigma|) \quad (3)$$

Where $\Sigma \in \mathbb{R}^{N \times N}$ is the covariance matrix ($\Sigma_{ij}$ is the covariance of $gene_i$ and $gene_j$), and $|\Sigma|$ denotes the determinant of $\Sigma$. Thresholding is done similarly to $H_{stp}$.

It is likely that E takes into account indirect links between genes. To correct for this, regularization is applied using glasso (v.1.10), which eliminates spurious links that are potentially an artifact of such indirect covariances. Glasso applies an L1-penalty to estimate a sparse inverse covariance matrix (precision matrix)[19]. The inverse of this sparse precision matrix is used as the regularized covariance matrix $\Sigma^\rho$ where $\rho$ denotes the regularization strength. The higher the value of $\rho$, the sparser the matrix. Multiple values of $\rho$ are scanned between 0 and 5 ($\rho=0$ being equivalent to $H_{temporal2}$ and $\rho>5$ being equivalent to $H_{temporal1}$). For each $\rho$, the inverse-regularized-inverse covariance entropy is computed as (equation 4)

$$H_{temporal3} = \ln(|\Sigma^\rho|) \quad (4)$$

and the appropriate threshold is selected. Note that this is the main temporal model for entropy presented in this work. The accuracy of each of these models is reported (with varying $\rho$,) on the training set. The final model selected has a $\rho$, and threshold value that maximizes accuracy.

TABLE 1

Project setup

| | | | | Data Collection | Predictions | | |
|---|---|---|---|---|---|---|---|
| Experimental Setup | | | | RNA-Seq timepoints | Fitness (Gene- | MOA (Gene- | Entropy (single |
| Stress | Species | Strain | Fitness | (min) | panel) | panel) | Entropy | timepoint) |
| Amoxicillin | *Streptococcus pneumoniae* | T4 | Low | 30, 120 | Test | Test | Test | Test |
| Cefepime | *Streptococcus pneumoniae* | T4 | Low | 30, 120 | Test | Test | Test | Test |
| Cefepime | *Streptococcus pneumoniae* | 19F | Low, High | 30, 120 | Test | Test | Test | Test |
| Ceftriaxone | *Streptococcus pneumoniae* | T4 | Low | 30, 120 | Test | Test | Test | Test |
| Ciprofloxacin | *Streptococcus pneumoniae* | T4 | Low | 30, 120 | Test | Test | Test | Test |
| Ciprofloxacin | *Streptococcus pneumoniae* | 19F | Low | 30, 120 | Test | Test | Test | Test |
| Ciprofloxacin | *Streptococcus pneumoniae* | aT4 | High | 30, 120 | Test | | Test | Test |
| Ciprofloxacin | *Streptococcus pneumoniae* | a19F | High | 30, 120 | Test | | Test | Test |
| Ciprofloxacin | *Streptococcus pneumoniae* | 23F | Low, High | 120 | | | | Validation |
| Ciprofloxacin | *Streptococcus pneumoniae* | 1 AR635 | Low | 120 | | | | Validation |
| Ciprofloxacin | *Salmonella* Typhimurium | (CDC) | Low | 120 | | | | Validation |
| Ciprofloxacin | *Staphylococcus aureus* | MN6 (CDC) | Low, High | 120 | | | | Validation |

TABLE 1-continued

Project setup

| Experimental Setup | | | | Data Collection | Predictions | | | |
|---|---|---|---|---|---|---|---|---|
| | | | | RNA-Seq timepoints (min) | Fitness (Gene-panel) | MOA (Gene-panel) | Entropy | Entropy (single timepoint) |
| Stress | Species | Strain | Fitness | | | | | |
| Ciprofloxacin | Escherichia coli | AR538 (CDC) | Low, High | 120 | | | | Validation |
| Ciprofloxacin | Klebsiella pneumoniae | AR497 (CDC) | Low, High | 120 | | | | Validation |
| Ciprofloxacin | Acinetobacter baumannii | LAC-4 | High | 120 | | | | Validation |
| Ciprofloxacin | Acinetobacter baumannii | 17978 | Low | 120 | | | | Validation |
| Cotrimoxazol | Streptococcus pneumoniae | T4 | Low | 30, 120 | Test | Test | Test | Test |
| Daptomycin | Streptococcus pneumoniae | T4 | Low | 30, 120 | Test | | Test | Test |
| Daptomycin | Streptococcus pneumoniae | 19F | Low | 30, 120 | Test | | Test | Test |
| Imipenem | Streptococcus pneumoniae | T4 | Low | 30, 120 | Test | Test | Test | Test |
| Kanamycin | Streptococcus pneumoniae | T4 | Low | 10, 20, 30, 45, 60, 90, 120, 150, 180, 210, 240 | Training | Training | Training | Training |
| Kanamycin | Streptococcus pneumoniae | 19F | Low | 10, 20, 30, 45, 60, 90, 120, 150, 180, 210, 240 | Training | Training | Training | Training |
| Kanamycin | Streptococcus pneumoniae | aT4 | High | 30, 60, 90, 120, 150, 180, 210, 240 | Training | | Training | Training |
| Kanamycin | Streptococcus pneumoniae | a19F | High | 30, 60, 90, 120, 150, 180, 210, 240 | Training | | Training | Training |
| Levofloxacin | Streptococcus pneumoniae | T4 | Low | 10, 20, 30, 45, 60, 90, 120, 150, 180 | Training | Training | Training | Training |
| Levofloxacin | Streptococcus pneumoniae | 19F | Low | 30, 60, 90, 120, 150, 180, 210, 240 | Training | Training | Training | Training |
| Levofloxacin | Streptococcus pneumoniae | aT4 | High | 30, 60, 90, 120, 150, 180, 210, 240 | Training | | Training | Training |
| Levofloxacin | Streptococcus pneumoniae | a19F | High | 30, 60, 90, 120, 150, 180, 210, 240 | Training | | Training | Training |
| Linezolid | Streptococcus pneumoniae | T4 | Low | 30, 120 | Test | Test | Test | Test |
| Moxifloxacin | Streptococcus pneumoniae | T4 | Low | 30, 120 | Test | Test | Test | Test |
| No Glycine | Streptococcus pneumoniae | T4 | High | 30, 90 | Training | | Training | Training |
| No Glycine | Streptococcus pneumoniae | D39 | Low | 30, 90 | Training | | Training | Training |
| No Uracil | Streptococcus pneumoniae | T4 | High | 30, 90 | Training | | Training | Training |
| No Uracil | Streptococcus pneumoniae | D39 | Low | 30, 60, 90, 120 | Training | | Training | Training |
| No Uracil | Streptococcus pneumoniae | aD39 | High | 30, 90 | Training | | Training | Training |
| No Valine | Streptococcus pneumoniae | T4 | High | 30, 90 | Training | | Training | Training |
| No Valine | Streptococcus pneumoniae | D39 | Low | 30, 90 | Training | | Training | Training |
| No Valine | Streptococcus pneumoniae | aD39 | High | 30, 20 | Training | | Training | Training |
| Penicillin | Streptococcus pneumoniae | T4 | Low | 10, 20, 30, 45, 60, 90, 120 | Training | Training | Training | Training |
| Penicillin | Streptococcus pneumoniae | 19F | High | 10, 20, 30, 45, 60, 90, 120 | Training | | Training | Training |
| Penicillin | Streptococcus pneumoniae | a19F | High | 10, 20, 30, 45, 60, 90, 120 | Training | | Training | Training |
| Rifampicin | Streptococcus pneumoniae | T4 | Low | 10, 20, 30, 45, 60, 90, 120 | Training | Training | Training | Training |
| Rifampicin | Streptococcus pneumoniae | 19F | Low | 10, 20, 30, 45, 60, 90, 120 | Training | Training | Training | Training |

TABLE 1-continued

Project setup

| Experimental Setup | | | | Data Collection | Predictions | | | |
| --- | --- | --- | --- | --- | --- | --- | --- | --- |
| Stress | Species | Strain | Fitness | RNA-Seq timepoints (min) | Fitness (Gene-panel) | MOA (Gene-panel) | Entropy | Entropy (single timepoint) |
| Rifampicin | Streptococcus pneumoniae | aT4 | High | 10, 20, 30, 45, 60, 90, 120 | Training | | Training | Training |
| Rifampicin | Streptococcus pneumoniae | a19F | High | 10, 20, 30, 45, 60, 90, 120 | Training | | Training | Training |
| Tetracycline | Streptococcus pneumoniae | T4 | Low | 30, 120 | Test | Test | Test | Test |
| Tetracycline | Streptococcus pneumoniae | 19F | Low, High | 30, 120 | Test | Test | Test | Test |
| Tobramycin | Streptococcus pneumoniae | T4 | Low | 30, 120 | Test | Test | Test | Test |
| Vancomycin | Streptococcus pneumoniae | T4 | Low | 10, 20, 30, 45, 60, 90 | Training | Training | Training | Training |
| Vancomycin | Streptococcus pneumoniae | 19F | Low | 10, 20, 30, 45, 60, 90, 120 | Training | Training | Training | Training |
| Vancomycin | Streptococcus pneumoniae | aT4 | High | 10, 20, 30, 45, 60, 90, 120 | Training | | Training | Training |
| Vancomycin | Streptococcus pneumoniae | a19F | High | 10, 20, 30, 45, 60, 90, 120 | Training | | Training | Training |

TABLE 2

Antibiotic minimum inhibitory concentrations (MIC) used in this study

| Antibiotic | 1x MIC for T4 (µg/mL) | 1x MIC for 19F (µg/mL) |
| --- | --- | --- |
| Amoxicilin (AMX) | 0.12 | na |
| Cefepime (CEF) | 0.8 | 2.2 |
| Ceftriaxone (CFT) | 0.007 | na |
| Ciprofloxacin (CIP) | 1 | 1 |
| Cotrimoxazol (COT) | 6.5 | na |
| Daptomycin (DAP) | 35 | 35 |
| Imipenem (IMI) | 0.03 | na |
| Kanamycin (KAN) | 90 | 90 |
| Levofloxacin (LVX) | 1 | 1.1 |
| Linezolid (LIN) | 0.5 | na |
| Moxifloxacin (MOX) | 0.45 | na |
| Penicillin (PEN) | 0.03 | 2.25 |
| Rifampicin (RIF) | 0.035 | 0.035 |
| Tetracycline (TET) | 8 | 22 |
| Tobramycin (TOB) | 175 | na |
| Vancomycin (VNC) | 0.24 | 0.24 | na: not tested in this study.

TABLE 3

Features and their coefficients in the fitness gene panel. Feature: the TIGR4 locus tag of the selected feature. Coefficient: the coefficient of the feature. Tag: Functional tag, Category: Functional category of the gene.

| Feature | Coefficient | Tag | Category | Gene Name | Gene Description |
| --- | --- | --- | --- | --- | --- |
| SP_0161 | −0.010279271 | GENETIC INFORMATION PROCESSING | Transcription | | |
| SP_0568 | 0.025001143 | GENETIC INFORMATION PROCESSING | Translation | | valyl-tRNA synthetase |
| SP_1300 | −0.034269552 | HYPOTHETICAL/UNKNOWN | NA | | Hypothetical Protein |
| SP_1869 | −0.03957627 | ENVIRONMENTAL INFORMATION PROCESSING | Membrane transport | | |
| SP_2195 | −0.019990526 | GENETIC INFORMATION PROCESSING | Transcription | ctsR | Transcriptional regulator CtsR |

TABLE 3-continued

Features and their coefficients in the fitness gene panel. Feature: the TIGR4 locus tag of the selected feature. Coefficient: the coefficient of the feature. Tag: Functional tag, Category: Functional category of the gene.

| Feature | Coefficient | Tag | Category | Gene Name | Gene Description |
|---|---|---|---|---|---|
| SP_0929 | 0.032539524 | GENETIC INFORMATION PROCESSING | Translation | rluD | Ribosomal large subunit pseudouridin synthase D |
| SP_0141 | −0.00392369 | GENETIC INFORMATION PROCESSING | Transcription | | transcriptional regulator, MutR family |
| SP_0680 | −0.019730034 | GENETIC INFORMATION PROCESSING | Translation | rsuA-2 | Ribosomal small subunit pseudouridine synthase A |
| SP_0197 | −0.00602077 | METABOLISM | Cofactor and vitamin metabolism | | Dihydrofolate synthase (EC 6.3.2.12) |
| SP_0336 | 0.022187461 | METABOLISM | Cell wall metabolism | | Penicillin-binding protein 2x |
| SP_1438 | 0.009735969 | ENVIRONMENTAL INFORMATION PROCESSING | Membrane transport | | ABC transporter, ATPase component |
| SP_0434 | 0.024817121 | HYPOTHETICAL/ UNKNOWN | NA | | |
| SP_0520 | −0.023400459 | HYPOTHETICAL/ UNKNOWN | NA | | |
| SP_1041 | 0.019562441 | HYPOTHETICAL/ UNKNOWN | NA | | |
| SP_0589 | 0.126448171 | METABOLISM | Amino acid metabolism | cysE | serine acetyltransferase |
| SP_1686 | −0.017175824 | HYPOTHETICAL/ UNKNOWN | NA | | Hypothetical Protein |
| SP_1895 | −0.001292326 | ENVIRONMENTAL INFORMATION PROCESSING | Membrane transport | rafG | sugar ABC transporter substrate-binding protein |
| SP_2167 | −0.003983055 | METABOLISM | Carbohydrate metabolism | fucK | L-fuculose kinase fucK |
| SP_1798 | −0.017352287 | ENVIRONMENTAL INFORMATION PROCESSING | Membrane transport | | |
| SP_1800 | 0.093566147 | GENETIC INFORMATION PROCESSING | Transcription | | |
| SP_1856 | −0.08663485 | GENETIC INFORMATION PROCESSING | Transcription | | |
| SP_1857 | −0.008283306 | ENVIRONMENTAL INFORMATION PROCESSING | Membrane transport | | Cation efflux system protein |
| SP_1396 | 0.000580467 | ENVIRONMENTAL INFORMATION PROCESSING | Membrane transport | pstB1 | Phosphate ABC transporter, ATP-binding component 1 |
| SP_1478 | 0.029056712 | METABOLISM | Various metabolism | | Aldo/keto reductase |
| SP_1527 | 0.006450843 | ENVIRONMENTAL INFORMATION PROCESSING | Membrane transport | aliB | Oligopeptide ABC transporter, oligopeptide-binding protein |
| SP_1597 | −0.015615773 | HYPOTHETICAL/ UNKNOWN | NA | | Hypothetical Protein |
| SP_2201 | −0.040685009 | CELLULAR PROCESSES | Cellular community | cbpD | Late competence protein cbpD-murein hydrolase |
| SP_1974 | −0.016625727 | METABOLISM | Various metabolism | | Acylphosphatase |
| (Intercept) | 0.760173069 | NA | NA | NA | NA |

TABLE 4

Features and their coefficients in the MOA-specific fitness panels.

| Panel | Feature | Coefficient | Tag | Category | Gene Name | Gene Description |
|---|---|---|---|---|---|---|
| CWSI-specific fitness | (Intercept) | 0.802510556 | | | | |
| CWSI-specific fitness | SP_0091 | −0.076552298 | ENVIRONMENTAL INFORMATION PROCESSING | Membrane transport | ugpE | ABC transporter permease |
| CWSI-specific fitness | SP_0410 | −0.014990773 | ENVIRONMENTAL INFORMATION PROCESSING | Membrane transport | NA | exfoliative toxin |
| CWSI-specific fitness | SP_1974 | −0.091374816 | METABOLISM | Various metabolism | NA | Acylphosphatase |
| CWSI-specific fitness | SP_2051 | −0.021830947 | ENVIRONMENTAL INFORMATION PROCESSING | Membrane transport | cgIC | Late competence protein ComGC |
| DSI-specific fitness | (Intercept) | 0.852083322 | | | | |
| DSI-specific fitness | SP_0079 | −0.231416616 | ENVIRONMENTAL INFORMATION PROCESSING | Membrane transport | trkA | Trk family potassium uptake protein |
| DSI-specific fitness | SP_0106 | −0.068270673 | METABOLISM | Amino acid metabolism | sdaB | L-serine dehydratase, iron-sulfur-dependent, beta subunit (EC 4.3.1.17) |
| DSI-specific fitness | SP_0894 | 0.020592366 | METABOLISM | Amino acid metabolism | pepX | x-prolyl-dipeptidyl aminopeptidase |
| DSI-specific fitness | SP_1398 | 0.007518056 | ENVIRONMENTAL INFORMATION PROCESSING | Membrane transport | pstA | Phosphate ABC transporter, permease component |
| DSI-specific fitness | SP_1472 | 0.007183581 | METABOLISM | Various metabolism | NA | Oxidoreductase |
| DSI-specific fitness | SP_2103 | −0.00451615 | GENETIC INFORMATION PROCESSING | Translation | rrmA | 23S rRNA (guanine(745)-N(l))-methyltransferase |
| DSI-specific fitness | SP_2201 | −0.005319221 | CELLULAR PROCESSES | Cellular community | cbpD | Late competence protein cbpD - murein hydrolase |
| DSI-specific fitness | SP_2217 | −0.009811251 | CELLULAR PROCESSES | Cell division | mreD | rod shpae-determining protein |
| PSI-specific fitness | (Intercept) | 0.760960208 | | | | |
| PSI-specific fitness | SP_0434 | 0.0496811 | HYPOTHETICAL/UNKNOWN | | | |
| PSI-specific fitness | SP_0678 | 0.05860058 | HYPOTHETICAL/UNKNOWN | | | hypothetical protein |
| PSI-specific fitness | SP_0913 | −0.024961142 | ENVIRONMENTAL INFORMATION PROCESSING | Membrane transport | | ABC transporter permease |
| PSI-specific fitness | SP_0953 | −0.053737175 | METABOLISM | Various metabolism | | Acetyltransferase |
| PSI-specific fitness | SP_1118 | 0.019527231 | METABOLISM | Cell wall metabolism | | pullulanase; |
| PSI-specific fitness | SP_1857 | 0.094105937 | ENVIRONMENTAL INFORMATION PROCESSING | Membrane transport | | Cation efflux system protein |

Panel: which panel the feature belongs to.
Feature: the TIGR4 locus tag of the selected feature.
Coefficient: the coefficient of the feature.
Tag: Functional tag,
Category: Functional category of the gene.

TABLE 5

Homologs in 6 pathogenic species of genes in 2 gene-panels that predict fitness (corresponding to FIGS. 1F, 1G). Homology data was obtained from the PATRIC database[1]. When present, the homolog is represented by its locus tag. An empty cell indicates absence of the homolog in that species. The two fitness panels included are the condition-agnostic gene-panel presented in this work, and the *E. coli* specific CIP gene-panel in a previous study[2].

| Gene-panel | PATRIC cross-genus families (PGfams) | *Acinetobacter baumannii* ATCC 17978 | *Escherichia coli* str. K-12 substr. MG 1655 | *Klebsiella pneumoniae* HS11286 | *Salmonella enterica* serovar Typhimurium str. LT2 | *Staphylococcus aureus* subsp. aureus NCTC 8325 | *Streptococcus pneumoniae* TIGR4 |
|---|---|---|---|---|---|---|---|
| This work | PGF_00004652 |  | 64490 | KPHS_19230 |  | SAOUHSC_00327 | SP_1300 |
| This work | PGF_00013324 |  |  |  |  |  | SP_0520 |
| This work | PGF_00015320 |  |  |  |  |  | SP_1869 |
| This work | PGF_00018135 |  |  |  |  |  | SP_1800 |
| This work | PGF_00035026 |  |  |  |  |  | SP_1115 |
| This work | PGF_00057506 | A1S_1043 |  |  | STM0354 | SAOUHSC_02461 | SP_1856 |
| This work | PGF_00300574 |  |  |  |  |  | SP_1041 |
| This work | PGF_00402268 |  |  |  |  | SAOUHSC_01907 | SP_1478 |
| This work | PGF_00417739 |  |  |  |  |  | SP_2201 |
| This work | PGF_01264994 |  | 64280 |  | STM1133 |  | SP_1325 |
| This work | PGF_02147779 |  | b1243 | KPHS_30000 | STM1746.S | SAOUHSC_00927 | SP_1527 |
| This work | PGF_02640939 |  |  |  |  |  | SP_2167 |
| This work | PGF_03065340 |  |  |  |  | SAOUHSC_02645 | SP_0161 |
| This work | PGF_03285992 |  |  |  |  |  | SP_1438 |
| This work | PGF_03515040 |  |  |  |  |  | SP_1597 |
| This work | PGF_03520500 |  |  |  |  |  | SP_1798 |
| This work | PGF_03889881 |  |  |  |  | SAOUHSC_00502 | SP_2195 |
| This work | PGF_04485073 | A1S_2868 | b2315 | KPHS_37740 | STM2365 | SAOUHSC_01766 | SP_0197 |
| This work | PGF_04695681 | A1S_1407 | b3607 | KPHS_51110 | STM3699 | SAOUHSC_00510 | SP_0589 |
| This work | PGF_05500127 | A1S_2742 | 64258 | KPHS_05160 | STM4475 | SAOUHSC_01767 | SP_0568 |
| This work | PGF_06213055 | A1S_2445 | b3725 | KPHS_52970 | STM3854 | SAOUHSC_01385 | SP_1396 |
| This work | PGF_06874321 |  |  |  |  |  | SP_1895 |
| This work | PGF_07619772 | A1S_1045 |  |  |  |  | SP_1857 |
| This work | PGF_09626318 | A1S_2120 | b2183 | KPHS_36820 | STM2222 | SAOUHSC_01870 | SP_0280 |
| This work | PGF_10302926 | A1S_3204 | b0084 | KPHS_33530 | STM0122 | SAOUHSC_01145 | SP_1673 |
| This work | PGF_10367439 |  | b0968 | KPHS_18770 | STM1083 | SAOUHSC_01406 | SP_1974 |
| This work | PGF_10569727 | A1S_0841 | b2594 | KPHS_39870 | STM2662 | SAOUHSC_01163 | SP_0929 |
| This work | PGF_12783997 |  |  |  |  |  | SP_0434 |
| Barczak et al. | PGF_00026615 | A1S_0888 | b3959 | KPHS_01010 | STM4122 | SAOUHSC_00147 |  |
| Barczak et al. | PGF_00047078 | A1S_1962 | b2699 | KPHS_41020 | STM2829 | SAOUHSC_01262 | SP_1940 |
| Barczak et al. | PGF_00403095 | A1S_0765 | b2498 | KPHS_38940 | STM2498 | SAOUHSC_02353 | SP_0745 |
| Barczak et al. | PGF_00690318 |  | b3645 | KPHS_52620 |  |  |  |
| Barczak et al. | PGF_04041316 | A1S_3295 | 64058 | KPHS_02820 | STM4254 | SAOUHSC_00780 | SP_0186 |

TABLE 6

Features and their coefficients in the MOA gene panel.

| Feature | Coefficient CWSI | Coefficient DSI | Coefficient PSI | Coefficient RSI | Tag | Category | Gene Name | Gene Description |
|---|---|---|---|---|---|---|---|---|
| SP_0338 | −0.06118 | −0.08609 | 0.195218 | −0.04794 | GENETIC INFORMATION PROCESSING | Folding, sorting, degradation |  | ATP-dependent Clp protease ATP-binding subunit |
| SP_0781 | 0.021672 | −0.02267 | −0.00596 | 0.006963 | HYPOTHETICAL/ UNKNOWN | NA |  | hypothetical protein |
| SP_0837 | −0.09865 | −0.03419 | 0.022513 | 0.110322 | GENETIC INFORMATION PROCESSING | Transcription | flaR | Putative DNA topology modulation protein FlaR |
| SP_0959 | −0.23 | 0.103554 | 0.240421 | −0.11398 | GENETIC INFORMATION PROCESSING | Translation | infC | translation initiation factor IF-3 |
| SP_1072 | −0.09697 | −0.06232 | −0.04418 | 0.203463 | GENETIC INFORMATION PROCESSING | Replication | dnaG | DNA primase |
| SP_1073 | −0.31249 | −0.31154 | −0.20928 | 0.833316 | GENETIC INFORMATION PROCESSING | Transcription | rpoD | RNA polymerase sigma factor RpoD |

TABLE 6-continued

Features and their coefficients in the MOA gene panel.

| Feature | Coefficient CWSI | Coefficient DSI | Coefficient PSI | Coefficient RSI | Tag | Category | Gene Name | Gene Description |
|---|---|---|---|---|---|---|---|---|
| SP_1926 | −0.00215 | 0.000952 | 0.002799 | −0.0016 | HYPOTHETICAL/ UNKNOWN | NA | | |
| SP_2107 | 0.099959 | −0.02395 | −0.06983 | −0.00617 | METABOLISM | Carbohydrate metabolism | malM | 4-alpha-glucanotransferase |
| SP_0977 | −0.02788 | −0.04462 | 0.051361 | 0.021145 | METABOLISM | Various metabolism | tehB | tellurite resistance protein TehB |
| SP_1027 | 0.144475 | −0.08052 | −0.0076 | −0.05635 | HYPOTHETICAL/ UNKNOWN | NA | | |
| SP_0151 | −0.00295 | 0.016818 | −0.01176 | −0.00211 | ENVIRONMENTAL INFORMATION PROCESSING | Membrane transport | | ABC transporter ATP-binding protein |
| SP_0330 | 0.144194 | 0.064263 | −0.06385 | −0.1446 | GENETIC INFORMATION PROCESSING | Transcription | regR | Sugar binding transcriptional regulator RegR |
| SP_1438 | 0.286369 | −0.31169 | −0.11143 | 0.136752 | ENVIRONMENTAL INFORMATION PROCESSING | Membrane transport | | ABC transporter, ATPase component |
| SP_0452 | −0.07995 | 0.015807 | −0.11159 | 0.17573 | ENVIRONMENTAL INFORMATION PROCESSING | Membrane transport | | amino acid ABC transporter ATP-binding protein |
| SP_0961 | −0.12918 | 0.06233 | 0.106884 | −0.04003 | GENETIC INFORMATION PROCESSING | Translation | rpIT | 50S ribosomal protein L20 |
| SP_2066 | −0.11206 | 0.056273 | −0.02984 | 0.08562 | METABOLISM | Amino acid metabolism | thrC | threonine synthase |
| SP_1190 | −0.02423 | −0.12339 | 0.053684 | 0.093939 | METABOLISM | Carbohydrate metabolism | lacD | |
| SP_1219 | 0.035421 | −0.1574 | 0.31921 | −0.19723 | GENETIC INFORMATION PROCESSING | Replication | gyrA | DNA gyrase, subunit A |
| SP_1227 | 0.002386 | −0.0231 | 0.065068 | −0.04436 | ENVIRONMENTAL INFORMATION PROCESSING | Signal transduction | vicR | DNA binding response regulator |
| SP_1805 | 0.057825 | −0.13463 | 0.064938 | 0.011868 | HYPOTHETICAL/ UNKNOWN | NA | | |
| SP_1584 | −0.00664 | −0.0483 | 0.030221 | 0.024721 | GENETIC INFORMATION PROCESSING | Transcription | codY | GTP-sensing transcriptional pleiotropic repressor codY |
| SP_1588 | 0.284896 | −0.00575 | −0.14589 | −0.13325 | METABOLISM | Nucleotide metabolism | | Pyridine nucleotide-disulfide oxidoreductase |
| SP_1271 | 3.07E−05 | −0.05722 | 0.053564 | 0.003624 | METABOLISM | Carbohydrate metabolism | ispD | 2-C-methyl-D-erythritol 4-phosphate cytidylyltransferase |
| SP_2229 | −0.08279 | 0.249454 | −0.15575 | −0.01092 | GENETIC INFORMATION PROCESSING | Translation | trpS | tryptophanyl-tRNA synthetase II |
| SP_1630 | −0.01263 | −0.01856 | 0.15798 | −0.12679 | HYPOTHETICAL/ UNKNOWN | NA | | Hypothetical Protein |
| SP_2113 | −0.04844 | 0.222414 | −0.1673 | −0.00668 | HYPOTHETICAL/ UNKNOWN | NA | | |
| SP_1690 | 0.132823 | −0.08118 | −0.06945 | 0.017806 | ENVIRONMENTAL INFORMATION PROCESSING | Membrane transport | | Putative ABC transporter, substrate-binding component |
| SP_1691 | 0.106428 | −0.04025 | −0.07081 | 0.004635 | HYPOTHETICAL/ UNKNOWN | NA | | Hypothetical Protein |
| SP_2186 | 0.061442 | 0.085354 | −0.10325 | −0.04355 | METABOLISM | Lipid metabolism | glpK | glycerol kinase |
| SP_2238 | −0.05756 | 0.172883 | −0.08982 | −0.02551 | GENETIC INFORMATION PROCESSING | Translation | rlmH | 23S rRNA (pseudouridine (191S)-N(3))-methyltransferase |
| SP_2084 | 0.21789 | 0.049282 | −0.3045 | 0.037323 | ENVIRONMENTAL INFORMATION PROCESSING | Membrane transport | pstS | |
| SP_2100 | −0.09722 | 0.247676 | −0.24355 | 0.093085 | GENETIC INFORMATION PROCESSING | Translation | | |
| SP_2141 | 0.022763 | 0.037692 | −0.08685 | 0.026395 | METABOLISM | Cell wall metabolism | | |

TABLE 6-continued

Features and their coefficients in the MOA gene panel.

| Feature | Coefficient CWSI | Coefficient DSI | Coefficient PSI | Coefficient RSI | Tag | Gene Category | Name | Gene Description |
|---|---|---|---|---|---|---|---|---|
| SP_2145 | 0.001032 | 0.014399 | −0.0191 | 0.003666 | METABOLISM | Cell wall metabolism | | Alpha-1,2-mannosidase |
| (Intercept) | −0.98051 | 0.317393 | 1.643493 | −0.98037 | NA | NA | NA | NA |

Feature: the TIGR4 locus tag of the selected feature.
Coefficient: the coefficient of the feature.
Tag: Functional tag,
Category: Functional category of the gene.

TABLE 7

Temporal entropy model predictions.

| Experiment | | | | | Rho = 1.5 | | Rho = ∞ | | Rho = 0 | |
|---|---|---|---|---|---|---|---|---|---|---|
| Survive | Strain | Adapted | AB | Concentration | Group | Entropy | Prediction | Entropy | Prediction | Entropy | Prediction |
| TRUE | 19F | FALSE | CEF | L | Test | 975.3411 | TRUE | −4.2986 | TRUE | −82233.4 | TRUE |
| FALSE | 19F | FALSE | CEF | H | Test | 1054.675 | TRUE | −3.40738 | TRUE | −80373.9 | TRUE |
| FALSE | 19F | FALSE | CIP | L | Test | 1036.983 | TRUE | −3.49596 | TRUE | −80496.2 | TRUE |
| FALSE | 19F | FALSE | DAP | L | Test | 1082.904 | FALSE | −3.17811 | TRUE | −79772.5 | TRUE |
| FALSE | 19F | FALSE | KAN | L | Train | 1193.194 | FALSE | −1.7714 | FALSE | −75912.6 | FALSE |
| FALSE | 19F | FALSE | LVX | L | Train | 1287.214 | FALSE | −1.47674 | FALSE | −76695.9 | FALSE |
| TRUE | 19F | FALSE | PEN | L | Train | 923.4468 | TRUE | −4.11277 | TRUE | −82510.7 | TRUE |
| FALSE | 19F | FALSE | RIF | L | Train | 1306.995 | FALSE | −1.57052 | FALSE | −76930.1 | FALSE |
| FALSE | 19F | FALSE | TET | H | Test | 1086.258 | FALSE | −2.89806 | TRUE | −79282 | TRUE |
| TRUE | 19F | FALSE | TET | L | Test | 1117.299 | FALSE | −2.92531 | TRUE | −79344.8 | TRUE |
| FALSE | 19F | FALSE | VNC | L | Train | 1256.953 | FALSE | −1.62245 | FALSE | −76788.8 | FALSE |
| TRUE | 19F | TRUE | CIP | L | Test | 903.3138 | TRUE | −5.16339 | TRUE | −83965.8 | TRUE |
| TRUE | T4 | TRUE | CIP | L | Test | 914.6849 | TRUE | −5.97936 | TRUE | −88166.7 | TRUE |
| FALSE | D39 | FALSE | GLY | NA | Train | 1074.217 | FALSE | −2.84361 | TRUE | −76848.4 | FALSE |
| FALSE | D39 | FALSE | URA | NA | Train | 1296.135 | FALSE | −1.514 | FALSE | −73826 | FALSE |
| FALSE | D39 | FALSE | VAL | NA | Train | 1080.02 | FALSE | −2.71829 | FALSE | −76464 | FALSE |
| TRUE | 19F | TRUE | KAN | L | Train | 933.9229 | TRUE | −3.54389 | TRUE | −80165.2 | TRUE |
| TRUE | 19F | TRUE | KAN | H | Train | 1047.375 | TRUE | −2.42022 | FALSE | −78580.6 | TRUE |
| TRUE | T4 | TRUE | KAN | L | Train | 935.3213 | TRUE | −4.06503 | TRUE | −82044.5 | TRUE |
| TRUE | T4 | TRUE | KAN | H | Train | 1003.908 | TRUE | −3.12312 | TRUE | −79658.3 | TRUE |
| TRUE | 19F | TRUE | LVX | L | Train | 924.1036 | TRUE | −3.86135 | TRUE | −80932.6 | TRUE |
| TRUE | 19F | TRUE | LVX | H | Train | 975.5749 | TRUE | −3.15134 | TRUE | −80109.2 | TRUE |
| TRUE | T4 | TRUE | LVX | L | Train | 956.8751 | TRUE | −3.64705 | TRUE | −80767 | TRUE |
| TRUE | T4 | TRUE | LVX | H | Train | 957.6326 | TRUE | −3.60188 | TRUE | −80657.5 | TRUE |
| TRUE | T4 | TRUE | PEN | L | Train | 1029.411 | TRUE | −3.10914 | TRUE | −82619.2 | TRUE |
| TRUE | T4 | TRUE | PEN | H | Train | 1091.334 | FALSE | −2.74313 | TRUE | −81410.6 | TRUE |
| TRUE | 19F | TRUE | RIF | L | Train | 881.3857 | TRUE | −5.62567 | TRUE | −85750 | TRUE |
| TRUE | 19F | TRUE | RIF | H | Train | 888.8274 | TRUE | −4.94695 | TRUE | −84354.6 | TRUE |
| TRUE | T4 | TRUE | RIF | L | Train | 974.8755 | TRUE | −3.50127 | TRUE | −83054.6 | TRUE |
| TRUE | T4 | TRUE | RIF | H | Train | 956.5659 | TRUE | −3.67255 | TRUE | −83306.6 | TRUE |
| FALSE | T4 | FALSE | AMX | NA | Test2 | 1341.037 | FALSE | −1.46209 | FALSE | −77140.8 | FALSE |
| FALSE | T4 | FALSE | CEF | L | Test | 1345.329 | FALSE | −1.70141 | FALSE | −78701.4 | TRUE |
| FALSE | T4 | FALSE | CFT | NA | Test2 | 1166.756 | FALSE | −2.70692 | FALSE | −80896.4 | TRUE |
| FALSE | T4 | FALSE | CIP | L | Test | 1333.311 | FALSE | −2.04466 | FALSE | −79503.9 | TRUE |
| FALSE | T4 | FALSE | COT | NA | Test2 | 1329.673 | FALSE | −1.71242 | FALSE | −78776.7 | TRUE |
| FALSE | T4 | FALSE | DAP | L | Test | 1128.687 | FALSE | −2.45523 | FALSE | −80438.6 | TRUE |
| TRUE | T4 | FALSE | GLY | NA | Train | 1004.896 | TRUE | −4.07824 | TRUE | −84076.7 | TRUE |
| FALSE | T4 | FALSE | IMI | NA | Test2 | 1087.932 | FALSE | −3.26728 | TRUE | −82136.9 | TRUE |
| FALSE | T4 | FALSE | KAN | L | Train | 1119.428 | FALSE | −2.38138 | FALSE | −79686.8 | TRUE |
| FALSE | T4 | FALSE | LIN | NA | Test2 | 1204.522 | FALSE | −2.07443 | FALSE | −79638.5 | TRUE |
| FALSE | T4 | FALSE | LVX | L | Train | 1215.97 | FALSE | −2.09028 | FALSE | −79662.6 | TRUE |
| FALSE | T4 | FALSE | MOX | NA | Test2 | 1183.66 | FALSE | −2.62069 | FALSE | −80808.4 | TRUE |
| FALSE | T4 | FALSE | PEN | L | Train | 1091.652 | FALSE | −2.63357 | FALSE | −81456 | TRUE |
| FALSE | T4 | FALSE | RIF | L | Train | 1191.624 | FALSE | −2.03601 | FALSE | −80172.9 | TRUE |
| FALSE | T4 | FALSE | TET | L | Test | 1221.145 | FALSE | −1.52925 | FALSE | −78424.8 | TRUE |
| FALSE | T4 | FALSE | TOB | NA | Test2 | 1353.414 | FALSE | −1.64539 | FALSE | −77322.3 | FALSE |
| TRUE | T4 | FALSE | URA | NA | Train | 953.8118 | TRUE | −4.95241 | TRUE | −86005.9 | TRUE |
| TRUE | T4 | FALSE | VAL | NA | Train | 1058.581 | TRUE | −3.60328 | TRUE | −83025.3 | TRUE |
| FALSE | T4 | FALSE | VNC | L | Train | 1162.361 | FALSE | −2.24791 | FALSE | −80640.9 | TRUE |
| TRUE | D39 | TRUE | URA | NA | Train | 881.8132 | TRUE | −5.58159 | TRUE | −82611.2 | TRUE |
| TRUE | 19F | TRUE | VNC | L | Train | 888.2264 | TRUE | −5.07248 | TRUE | −84705.3 | TRUE |
| TRUE | 19F | TRUE | VNC | H | Train | 920.2137 | TRUE | −3.84356 | TRUE | −81456 | TRUE |
| TRUE | D39 | TRUE | VAL | NA | Train | 975.0714 | TRUE | −3.89497 | TRUE | −79046.8 | TRUE |

TABLE 7-continued

Temporal entropy model predictions.

| Experiment | | | | | Rho = 1.5 | | Rho = ∞ | | Rho = 0 | |
|---|---|---|---|---|---|---|---|---|---|---|
| Survive | Strain | Adapted | AB | Concentration | Group | Entropy | Prediction | Entropy | Prediction | Entropy | Prediction |
| TRUE | T4 | TRUE | VNC | L | Train | 920.4918 | TRUE | −4.61982 | TRUE | −86106.7 | TRUE |
| TRUE | T4 | TRUE | VNC | H | Train | 1061.581 | TRUE | −2.77797 | TRUE | −81905.2 | TRUE |

Survive: real survival outcome.

Strain: strain background used.

Adapted: whether the strain has been adapted to the condition.

AB: antibiotic (or nutrient) condition. Concentration: concentration of antibiotic used (L = low, H = high).

Group: whether the experiment is in the training set or test set. For each of the temporal models (Regularization value rho = 1.5, ∞, or 0), the entropy values and prediction are listed.

TABLE 8

Model performance for all finalized fitness prediction models.

| Model | Group | Number | NIR | TP | TN | FP | FN | Cohen's Kappa | AUROC |
|---|---|---|---|---|---|---|---|---|---|
| Gene Panel | Training | 138 | 0.6812 | 94 | 34 | 10 | 0 | 0.8224 | 0.993956 |
| Gene Panel | Test | 19 | 0.7895 | 4 | 11 | 4 | 0 | 0.5366 | 0.75 |
| Temporal entropy (rho = ∞) | Training | 36 | 0.6667 | 23 | 11 | 1 | 1 | 0.875 | 0.982639 |
| Temporal entropy (rho = ∞) | Test | 19 | 0.7895 | 4 | 10 | 5 | 0 | 0.4571 | 0.933333 |
| Temporal entropy (rho = 0) | Training | 36 | 0.6667 | 24 | 7 | 5 | 0 | 0.6512 | 0.913194 |
| Temporal entropy (rho = 0) | Test | 19 | 0.7895 | 4 | 2 | 13 | 0 | 0.0608 | 0.85 |
| Temporal entropy (rho = 1.5) | Training | 36 | 0.6667 | 23 | 12 | 0 | 1 | 0.9388 | 0.993056 |
| Temporal entropy (rho = 1.5) | Test | 19 | 0.75 | 3 | 13 | 2 | 1 | 0.5649 | 0.916667 |
| Entropy (single timepoint) | Training | 231 | 0.6537 | 147 | 41 | 39 | 4 | 0.5417 | 0.790149 |
| Entropy (single timepoint) | Test | 38 | 0.7895 | 8 | 15 | 15 | 0 | 0.2963 | 0.875 |
| Entropy (single timepoint; early) | Training | 93 | 0.6129 | 54 | 16 | 20 | 3 | 0.4291 | 0.705166 |
| Entropy (single timepoint; early) | Test | 19 | 0.7895 | 3 | 9 | 6 | 1 | 0.24 | 0.8 |
| Entropy (single timepoint; late) | Training | 138 | 0.6812 | 90 | 31 | 13 | 4 | 0.7001 | 0.897727 |
| Entropy (single timepoint; late) | Test | 19 | 0.7895 | 4 | 12 | 3 | 0 | 0.6275 | 1 |

TABLE 8-continued

Model performance for all finalized fitness prediction models.

| Model | AUPRC | Sensitivity | Specificity | PPV | NPV | Accuracy | Balanced Accuracy | F1 |
|---|---|---|---|---|---|---|---|---|
| Gene Panel | 0.997277 | 1 | 0.772727 | 0.903846 | 1 | 0.927536 | 0.886364 | 0.949495 |
| Gene Panel | 0.314235 | 1 | 0.733333 | 0.5 | 1 | 0.789474 | 0.866667 | 0.666667 |
| Temporal entropy (rho = ∞) | 0.967558 | 0.958333 | 0.916667 | 0.958333 | 0.916667 | 0.944444 | 0.9375 | 0.958333 |
| Temporal entropy (rho = ∞) | 0.980821 | 1 | 0.666667 | 0.444444 | 1 | 0.736842 | 0.833333 | 0.615385 |
| Temporal entropy (rho = 0) | 0.862189 | 1 | 0.583333 | 0.827586 | 1 | 0.861111 | 0.791667 | 0.90566 |
| Temporal entropy (rho = 0) | 0.944888 | 1 | 0.133333 | 0.235294 | 1 | 0.315789 | 0.566667 | 0.380952 |
| Temporal entropy (rho = 1.5) | 0.986079 | 0.958333 | 1 | 1 | 0.923077 | 0.972222 | 0.979167 | 0.978723 |
| Temporal entropy (rho = 1.5) | 0.97502 | 0.75 | 0.866667 | 0.6 | 0.928571 | 0.842105 | 0.808333 | 0.666667 |
| Entropy (single timepoint) | 0.771126 | 0.97351 | 0.5125 | 0.790323 | 0.911111 | 0.813853 | 0.743005 | 0.872404 |
| Entropy (single timepoint) | 0.963406 | 1 | 0.5 | 0.347826 | 1 | 0.605263 | 0.75 | 0.516129 |
| Entropy (single timepoint; early) | 0.709462 | 0.947368 | 0.444444 | 0.72973 | 0.842105 | 0.752688 | 0.695906 | 0.824427 |
| Entropy (single timepoint; early) | 0.90758 | 0.75 | 0.6 | 0.333333 | 0.9 | 0.631579 | 0.675 | 0.461538 |
| Entropy (single timepoint; late) | 0.861196 | 0.957447 | 0.704545 | 0.873786 | 0.885714 | 0.876812 | 0.830996 | 0.913706 |
| Entropy (single timepoint; late) | 1 | 1 | 0.8 | 0.571429 | 1 | 0.842105 | 0.9 | 0.727273 |

Model: name of the model.
Group: training or test set.
Number: number of data points in the group.
NIR: no information rate, which is the same as the prevalence of the majority outcome.
TP: number of true positives.
TN: number of true negatives.
FP: number of false positives.
FN: number of false negatives.
PPV: positive predictive value.
NPV: negative predictive value.

C. References

References are cited herein throughout using the format of reference number(s) enclosed by parentheses corresponding to one or more of the following numbered references. For example, citation of references numbers 1 and 2 immediately herein below would be indicated in the disclosure as (1, 2) or (1-2).

1. Battesti, A. & Bouveret, E. Acyl carrier protein/SpoT interaction, the switch linking SpoT-dependent stress response to fatty acid metabolism. Molecular Microbiology 62, 1048-1063 (2006).

2. Lopez, J. M., Dromerick, A. & Freese, E. Response of Guanosine 5'-Triphosphate Concentration to Nutritional Changes and Its Significance for Bacillus subtilis Sporulation. Journal of Bacteriology 146, 605-613 (1981).

3. Chatterjee, A., Saranath, D., Bhatter, P. & Misty, N. Global Transcriptional Profiling of Longitudinal Clinical Isolates of Mycobacterium tuberculosis Exhibiting Rapid Accumulation of Drug Resistance. PLOS ONE 8, e54717 (2013).

4. Erill, I., Campoy, S. & Barbé, J. Aeons of distress: an evolutionary perspective on the bacterial SOS response. FEMS Microbiol Rev 31, 637-656 (2007).

5. Au, N. et al. Genetic Composition of the Bacillus subtilis SOS System. Journal of Bacteriology 187, 7655-7666 (2005).

6. Little, J. W. & Mount, D. W. The SOS regulatory system of Escherichia coli. Cell 29, 11-22 (1982).

7. Yim, G., McClure, J., Surette, M. G. & Davies, J. E. Modulation of Salmonella gene expression by subinhibitory concentrations of quinolones. The Journal of Antibiotics 64, 73-78 (2011).

8. Barczak, A. K. et al. RNA signatures allow rapid identification of pathogens and antibiotic susceptibilities. Proc Natl Acad Sci U S A 109, 6217-6222 (2012).

9. Suzuki, S., Horinouchi, T. & Furusawa, C. Prediction of antibiotic resistance by gene expression profiles. Nature Communications 5, 5792 (2014).

10. Horinouchi, T. et al. Prediction of Cross-resistance and Collateral Sensitivity by Gene Expression profiles and Genomic Mutations. Sci Rep 7, (2017).

11. Bhattacharyya, R. P. et al. Simultaneous detection of genotype and phenotype enables rapid and accurate antibiotic susceptibility determination. Nature Medicine 1-7 (2019) doi:10.1038/s41591-019-0650-9.

12. Khazaei, T., Barlow, J. T., Schoepp, N. G. & Ismagilov, R. F. RNA markers enable phenotypic test of antibiotic susceptibility in Neisseria gonorrhoeae after 10 minutes of ciprofloxacin exposure. Sci Rep 8, (2018).

13. Zeitler, K. & Narayanan, N. The Present and Future State of Antimicrobial Stewardship and Rapid Diagnostic Testing: Can One Ideally Succeed Without the Other? Curr Treat Options Infect Dis 11, 177-187 (2019).

14. Boutte, C. C. & Crosson, S. Bacterial lifestyle shapes stringent response activation. Trends in Microbiology 21, 174-180 (2013).

15. Baharoglu, Z. & Mazel, D. SOS, the formidable strategy of bacteria against aggressions. FEMS Microbiol Rev 38, 1126-1145 (2014).

16. Gottesman, S. Trouble is coming: Signaling pathways that regulate general stress responses in bacteria. J. Biol. Chem. jbc.REV119.005593 (2019) doi:10.1074/jbc.REV119.005593.

17. Jensen, P. A., Zhu, Z. & van Opijnen, T. Antibiotics Disrupt Coordination between Transcriptional and Phenotypic Stress Responses in Pathogenic Bacteria. Cell Rep 20, 1705-1716 (2017).

18. van Opijnen, T., Bodi, K. L. & Camilli, A. Tn-seq: high-throughput parallel sequencing for fitness and genetic interaction studies in microorganisms. Nature Methods 6, 767-772 (2009).

19. van Opijnen, T. & Camilli, A. Transposon insertion sequencing: a new tool for systems-level analysis of microorganisms. Nature Reviews Microbiology 11, 435-442 (2013).

20. Opijnen, T. van & Camilli, A. A fine scale phenotype—genotype virulence map of a bacterial pathogen. Genome Res. 22, 2541-2551 (2012).

21. Opijnen, T. van & Camilli, A. Genome-Wide Fitness and Genetic Interactions Determined by Tn-seq, a High-Throughput Massively Parallel Sequencing Method for Microorganisms. Current Protocols in Microbiology 19, 1E.3.1-1E.3.16 (2010).

22. Opijnen, T. van, Dedrick, S. & Bento, J. Strain Dependent Genetic Networks for Antibiotic-Sensitivity in a Bacterial Pathogen with a Large Pan-Genome. PLOS Pathogens 12, e1005869 (2016).

23. Wadsworth, C. B., Sater, M. R. A., Bhattacharyya, R. P. & Grad, Y. H. Impact of Species Diversity on the Design of RNA-Based Diagnostics for Antibiotic Resistance in Neisseria gonorrhoeae. Antimicrobial Agents and Chemotherapy 63, (2019).

24. Surujon, D. & van Opijnen, T. ShinyOmics: collaborative exploration of omics-data. BMC Bioinformatics 21, 22 (2020).

25. Friedman, J., Hastie, T. & Tibshirani, R. Regularization Paths for Generalized Linear Models via Coordinate Descent. J Stat Softw 33, 1-22 (2010).

26. Krstajic, D., Buturovic, L. J., Leahy, D. E. & Thomas, S. Cross-validation pitfalls when selecting and assessing regression and classification models. Journal of Cheminformatics 6, 10 (2014).

27. Hutter, B. et al. Prediction of Mechanisms of Action of Antibacterial Compounds by Gene Expression Profiling. Antimicrobial Agents and Chemotherapy 48, 2838-2844 (2004).

28. Boshoff, H. I. M. et al. The Transcriptional Responses of Mycobacterium tuberculosis to Inhibitors of Metabolism NOVEL INSIGHTS INTO DRUG MECHANISMS OF ACTION. J. Biol. Chem. 279, 40174-40184 (2004).

29. Kaneko, K., Furusawa, C. & Yomo, T. Universal Relationship in Gene-Expression Changes for Cells in Steady-Growth State. Phys. Rev. X 5, 011014 (2015).

30. Ahmed, N. A. & Gokhale, D. V. Entropy expressions and their estimators for multivariate distributions. IEEE Transactions on Information Theory 35, 688-692 (1989).

31. Misra, N., Singh, H. & Demchuk, E. Estimation of the entropy of a multivariate normal distribution. Journal of Multivariate Analysis 92, 324-342 (2005).

32. Cai, T. T., Liang, T. & Zhou, H. H. Law of log determinant of sample covariance matrix and optimal estimation of differential entropy for high-dimensional Gaussian distributions. Journal of Multivariate Analysis 137, 161-172 (2015).

33. Srivastava, S. & Gupta, M. R. Bayesian estimation of the entropy of the multivariate Gaussian. in 2008 IEEE International Symposium on Information Theory 1103-1107 (2008). doi:10.1109/ISIT.2008.4595158.

34. Friedman, J., Hastie, T. & Tibshirani, R. Sparse inverse covariance estimation with the graphical lasso. Biostatistics 9, 432-441 (2008).

35. Thieffry, D., Huerta, A. M., Pérez-Rueda, E. & Collado-Vides, J. From specific gene regulation to genomic networks: a global analysis of transcriptional regulation in Escherichia coli. BioEssays 20, 433-440 (1998).

36. di Bernardo, D. et al. Chemogenomic profiling on a genome-wide scale using reverse-engineered gene networks. Nature Biotechnology 23, 377-383 (2005).

37. Galagan, J. E. et al. The Mycobacterium tuberculosis regulatory network and hypoxia. Nature 499, 178-183 (2013).

38. Lazo, A. V. & Rathie, P. On the entropy of continuous probability distributions (Corresp.). IEEE Transactions on Information Theory 24, 120-122 (1978).

39. Rustad, T. R. et al. Mapping and manipulating the Mycobacterium tuberculosis transcriptome using a transcription factor overexpression-derived regulatory network. Genome Biology 15, 502 (2014).

40. Ma, S. et al. Network stress test reveals novel drug potentiators in Mycobacterium tuberculosis. bioRxiv 429373 (2018) doi:10.1101/429373.

41. Zhang, B. & Horvath, S. A General Framework for Weighted Gene Co-Expression Network Analysis. Statistical Applications in Genetics and Molecular Biology 4, (2005).

42. Jenkins, S. G. & Schuetz, A. N. Current Concepts in Laboratory Testing to Guide Antimicrobial Therapy. Mayo Clinic Proceedings 87, 290-308 (2012).

43. Westermann, A. J., Gorski, S. A. & Vogel, J. Dual RNA-seq of pathogen and host. Nature Reviews Microbiology 10, 618-630 (2012).

44. Aprianto, R., Slager, J., Holsappel, S. & Veening, J.-W. Time-resolved dual RNA-seq reveals extensive rewiring of lung epithelial and pneumococcal transcriptomes during early infection. Genome Biology 17, 198 (2016).

45. Geiss, G. K. et al. Direct multiplexed measurement of gene expression with color-coded probe pairs. Nature Biotechnology 26, 317-325 (2008).46. Dunbar, S. A. Applications of Luminex® xMAPTM technology for rapid, high-throughput multiplexed nucleic acid detection. Clinica Chimica Acta 363, 71-82 (2006).

46. Wattam, A. R. et al. PATRIC, the bacterial bioinformatics database and analysis resource. Nucleic Acids Res 42, D581-D591 (2014).

47. Barczak, A. K. et al. RNA signatures allow rapid identification of pathogens and antibiotic susceptibilities. Proc Natl Acad Sci U S A 109, 6217-6222 (2012).

48. Aaberge, I. S., Eng, J., Lermark, G. & Lvik, M. Virulence of Streptococcus pneumoniae in mice: a standardized method for preparation and frozen storage of the experimental bacterial inoculum. Microbial Pathogenesis 18, 141-152 (1995).

49. Tettelin, H. et al. Complete Genome Sequence of a Virulent Isolate of Streptococcus pneumoniae. Science 293, 498-506 (2001).

50. Shi, Z.-Y., Enright, M. C., Wilkinson, P., Griffiths, D. & Spratt, B. G. Identification of Three Major Clones of Multiply Antibiotic-Resistant Streptococcus pneumoniae in Taiwanese Hospitals by Multilocus Sequence Typing. J Clin Microbiol 36, 3514-3519 (1998).

51. McGee, L. et al. Nomenclature of Major Antimicrobial-Resistant Clones of Streptococcus pneumoniae Defined by the Pneumococcal Molecular Epidemiology Network. Journal of Clinical Microbiology 39, 2565-2571 (2001).

52. Lanie, J. A. et al. Genome Sequence of Avery's Virulent Serotype 2 Strain D39 of Streptococcus pneumoniae and Comparison with That of Unencapsulated Laboratory Strain R6. Journal of Bacteriology 189, 38-51 (2007).

53. Cremers, A. J. H. et al. The post-vaccine microevolution of invasive Streptococcus pneumoniae. Scientific Reports 5, 14952 (2015).

54. Jensen, P. A., Zhu, Z. & van Opijnen, T. Antibiotics Disrupt Coordination between Transcriptional and Phenotypic Stress Responses in Pathogenic Bacteria. Cell Rep 20, 1705-1716 (2017).

55. Opijnen, T. van & Camilli, A. A fine scale phenotype—genotype virulence map of a bacterial pathogen. Genome Res. 22, 2541-2551 (2012).

56. Opijnen, T. van & Camilli, A. A fine scale phenotype—genotype virulence map of a bacterial pathogen. Genome Res. 22, 2541-2551 (2012).

57. Shishkin, A. A. et al. Simultaneous generation of many RNA-seq libraries in a single reaction. Nature Methods 12, 323-325 (2015).

58. Haas, B. J., Chin, M., Nusbaum, C., Birren, B. W. & Livny, J. How deep is deep enough for RNA-Seq profiling of bacterial transcriptomes? BMC Genomics 13, 734 (2012).

59. Langmead, B. & Salzberg, S. L. Fast gapped-read alignment with Bowtie 2. Nature Methods 9, 357-359 (2012).

60. Liao, Y., Smyth, G. K. & Shi, W. featureCounts: an efficient general purpose program for assigning sequence reads to genomic features. Bioinformatics 30, 923-930 (2014).

61. Love, M. I., Huber, W. & Anders, S. Moderated estimation of fold change and dispersion for RNA-seq data with DESeq2. Genome Biology 15, 550 (2014).

62. Friedman, J., Hastie, T. & Tibshirani, R. Regularization Paths for Generalized Linear Models via Coordinate Descent. J Stat Softw 33, 1-22 (2010).

63. Krstajic, D., Buturovic, L. J., Leahy, D. E. & Thomas, S. Cross-validation pitfalls when selecting and assessing regression and classification models. Journal of Cheminformatics 6, 10 (2014).

64. Bhattacharyya, R. P. et al. Simultaneous detection of genotype and phenotype enables rapid and accurate antibiotic susceptibility determination. Nature Medicine 1-7 (2019) doi:10.1038/s41591-019-0650-9.

65. Friedman, J., Hastie, T. & Tibshirani, R. Sparse inverse covariance estimation with the graphical lasso. Biostatistics 9, 432-441 (2008).

It will be apparent to those skilled in the art that various modifications and variations can be made in the present disclosure without departing from the scope or spirit of the disclosure. Other embodiments of the disclosure will be apparent to those skilled in the art from consideration of the specification and practice of the disclosure disclosed herein. It is intended that the specification and examples be considered as exemplary only, with a true scope and spirit of the disclosure being indicated by the following claims.

What is claimed is:

1. An entropy method for predicting a diagnostic or prognostic outcome, comprising:
    a) generating and analyzing a substantial dataset for a pathogen of interest,
    b) calculating entropy using time-series RNA-Seq data and dependencies amongst genes of the pathogen of interest, and
    c) providing a fitness prediction using a simple decision rule, where if entropy is either above or below a threshold, fitness is respectively low or high,
    wherein the fitness prediction corresponds to the diagnostic or prognostic outcome.

2. The entropy method of claim 1, wherein entropy is transcriptional entropy.

3. The entropy method of claim 2, wherein entropy is calculated on a transcriptomic dataset with multiple time-points, wherein entropy (H) is as follows:

$$H = ln(|\Sigma_\rho|) \quad (1)$$

Where $\Sigma$ is the empirical covariance matrix ($\Sigma_{ij}$ is the empirical covariance of $gene_i$ and $gene_j$ computed from the time series data), and $|\Sigma|$ denotes the determinant of $\Sigma$, and wherein $\Sigma_\rho$ is a graphical-lasso regularized $\Sigma$, where $\rho$ denotes the regularization strength.

4. The entropy method of claim 3, wherein entropy is computed with multiple timepoints, wherein a) a temporal differential expression (DE) data is used to compute a gene-gene empirical covariance matrix $\Sigma$, b) Graphical lasso is applied to $\Sigma$ to obtain a regularized inverse of this covariance matrix ($\Sigma\rho^{-1}$), wherein the matrix $\rho\rho^{-1}$ represents a network of dependencies of regulatory interactions of the genes, and c) the inverse of this matrix ($\Sigma\rho$) is used in Equation 1 of claim 3 to compute entropy.

5. The entropy method of claim 2, wherein entropy is calculated for a single-timepoint transcriptome profile, wherein entropy ($H_{stp}$) as follows:

$$H_{stp} = ln(\sigma^2) \quad (2)$$

Wherein $\sigma^2$ is the variance of the distribution of differential expression across genes for a single timepoint.

6. The entropy method of claim 1, wherein the pathogen is bacterium.

7. The entropy method of claim 6, wherein the bacterium is explored to at least one antibiotic.

8. The entropy method of claim 7, wherein the fitness predictions indicate the antibiotic sensitivity.

9. An entropy-based method for predictions on infection progression in a patient, comprising: a) collecting a sample from the patient, b) directly performing RNA expression analyses on the sample and on the patient's response to a therapeutic agent, simultaneously, c) combining entropy level of the sample and the patient-response to the therapeutic agent, wherein the entropy fitness indicates whether the therapeutic agent works.

10. The entropy-based method of claim 9, wherein the sample is bacterium.

11. The entropy-based method of claim 9, wherein the therapeutic agent is an antibiotic.

12. An entropy-based method for Antibiotic Susceptibility Test (AST), comprising:
   a) collecting a bacterium from a patient or any bacterium of interest,
   b) exposing the bacterium to a tested antibiotic in an effective amount,
   c) collecting RNA from the bacterium that exposed to the tested antibiotic and performing RNA expression analyses,
   d) performing entropy calculation for survival probability and actual level of antibiotic sensitivity, and
   e) providing a recommendation on optimal treatment with the tested antibiotics in view of the entropy information.

13. The entropy-based method of claim 12, wherein the entropy calculation is performed on a transcriptomic dataset with multiple timepoints, wherein entropy (H) is as follows:

$$H = ln(|\Sigma_\rho|) \qquad (1)$$

Where is the empirical covariance matrix ($\Sigma_{ij}$ is the empirical covariance of gene$_i$ and gene$_j$ computed from the time series data), and $|\Sigma|$ denotes the determinant of $\Sigma$, and wherein $\Sigma_\rho$ is a graphical-lasso regularized $\Sigma$, where $\rho$ denotes the regularization strength.

14. The entropy-based method of claim 12, wherein entropy is calculated for a single-timepoint transcriptome profile, wherein entropy ($H_{stp}$) as follows:

$$H_{stp} = ln(\sigma^2) \qquad (2)$$

Wherein $\sigma^2$ is the variance of the distribution of differential expression across genes for a single timepoint.

15. A transcriptional entropy method for predicting a diagnostic or prognostic outcome, comprising:
   d) generating and analyzing a substantial dataset for a pathogen of interest,
   e) calculating entropy using time-series RNA-Seq data and dependencies amongst genes of the pathogen of interest, and
   f) providing a fitness prediction using a simple decision rule, where if entropy is either above or below a threshold, fitness is respectively low or high,
   wherein the fitness prediction corresponds to the diagnostic or prognostic outcome, and
   wherein entropy is calculated on a transcriptomic dataset with multiple timepoints, wherein entropy (H) is as follows:

$$H = ln(|\Sigma_\rho|) \qquad (1)$$

Where is the empirical covariance matrix ($\Sigma_{ij}$ is the empirical covariance of gene$_i$ and gene$_j$ computed from the time series data), and $|\Sigma|$ denotes the determinant of $\Sigma$, and wherein $\Sigma_\rho$ is a graphical-lasso regularized $\Sigma$, where $\rho$ denotes the regularization strength.

16. The transcriptional entropy method of claim 15, wherein entropy is computed with multiple timepoints, wherein a) a temporal differential expression (DE) data is used to compute a gene-gene empirical covariance matrix $\Sigma$, b) Graphical lasso is applied to $\Sigma$ to obtain a regularized inverse of this covariance matrix ($\Sigma\rho^{-1}$), wherein the matrix $\Sigma\rho^{-1}$ represents a network of dependencies of regulatory interactions of the genes, and c) the inverse of this matrix ($\Sigma\rho$) is used in Equation 1 of claim 3 to compute entropy.

17. The transcriptional entropy method of claim 15, wherein entropy is calculated for a single-timepoint transcriptome profile, wherein entropy ($H_{stp}$) as follows:

$$H_{stp} = ln(\sigma^2) \qquad (2)$$

Wherein $\sigma^2$ is the variance of the distribution of differential expression across genes for a single timepoint.

18. The transcriptional entropy method of claim 15, wherein the pathogen is bacterium.

19. The transcriptional entropy method of claim 18, wherein the bacterium is explored to at least one antibiotic.

20. The transcriptional entropy method of claim 19, wherein the fitness predictions indicate the antibiotic sensitivity.

* * * * *